(12) United States Patent
Nash et al.

(10) Patent No.: US 8,613,925 B2
(45) Date of Patent: Dec. 24, 2013

(54) ANTI-IL-13Rα1 ANTIBODIES AND THEIR USES THEREOF

(75) Inventors: Andrew Donald Nash, Kew (AU); Manuel Baca, Gaithersburg, MD (US); Louis Jerry Fabri, Diamond Creek (AU); Dennis Zaller, Scotch Plains, NJ (US); William R. Strohl, Bridgewater, NJ (US); Zhiqiang An, Ambler, PA (US)

(73) Assignee: CSL Limited, Parkville, Victoria (AU)

( * ) Notice: Subject to any disclaimer, the term of this patent is extended or adjusted under 35 U.S.C. 154(b) by 723 days.

(21) Appl. No.: 12/445,753

(22) PCT Filed: Oct. 19, 2007

(86) PCT No.: PCT/US2007/081884
§ 371 (c)(1),
(2), (4) Date: Nov. 1, 2010

(87) PCT Pub. No.: WO2008/060814
PCT Pub. Date: May 22, 2008

(65) Prior Publication Data
US 2011/0052597 A1    Mar. 3, 2011

Related U.S. Application Data

(60) Provisional application No. 60/852,780, filed on Oct. 19, 2006.

(51) Int. Cl.
*A61K 39/395* (2006.01)

(52) U.S. Cl.
USPC ..................................................... 424/144.1

(58) Field of Classification Search
None
See application file for complete search history.

(56) References Cited

U.S. PATENT DOCUMENTS 5,859,205 A * 1/1999 Adair et al. ................ 530/387.3
2005/0058645 A1   3/2005 Dunlop et al. .............. 424/145.1

FOREIGN PATENT DOCUMENTS

| EP | 1449851 A1 | 8/2004 |
|---|---|---|
| EP | 07868510.4 | 6/2010 |
| WO | WO 97/15663 | 5/1997 |
| WO | WO 03/046009 | 6/2003 |
| WO | WO 03/080675 | 10/2003 |
| WO | WO 2006/055178 A2 | 5/2006 |
| WO | WO 2006/072564 | 7/2006 |

OTHER PUBLICATIONS

Eduardo Padlan, Mol Immunol. Feb. 1994;31(3):169-217.*
Portolano et al., J Immunol. Feb. 1, 1993;150(3):880-7.*
Boutten et al., Thorax 59:850-854, 2004.*
Lentsch et al. Respiration Physiology 128 (2001) 17-22.*
Webb et al., J. Immunol. 2000;165;108-113.*
Matsukawa et al., J. Immunol. 2000;164;2738-2744.*
Brightling et al., Clinical & Experimental Allergy, 40, 42-49 (2009).*
GENBANK accession No. NP_001551, publication date Aug. 20, 2006, pp. 1-5.*
Heller et al., Immunity, vol. 17, 629-638, Nov. 2002.*
Akiho et al., Am J Physiol Gastrointest Liver Physiol. Apr. 2005;288(4):G609-15. Epub Nov. 4, 2004.*
Neurath et al., Intern. Rev. Immunol., vol. 19, pp. 51-62, 2000.*
Niessner et al., Clin Exp Immunol. Sep. 1995;101(3):428-35.*
Camoglio et al., Inflamm Bowel Dis. Nov. 1998;4(4):285-90.*
GENOVAC "Product Data Sheet Anti-Human IL13 Receptor (IL13-R) Monoclonal Antibody" Catalog No. GM-0104 http://liferesearch.com/media/pdf/genovac/GM-0104.pdf> Retrieved May 11, 2010.
Aman et al., "cDNA cloning and characterization of the human interleukin 13 receptor α chain", The Journal of Biological Chemistry 1996 271(46):29265-29270.
Arima et al., "Characterization of the interaction between interleukin-13 and interleukin-13 receptors", The Journal of Biological Chemistry, 2005 280(26):24915-24922.
Akaiwa et al., "Localization of human interleukin 13 receptor in non-haematopoietic cells", Cytokine 2001 13(2):75-84.
Cancino-Diaz et al., "Interleukin-13 receptor in psoriatic keratinocytes:overexpression of the mRNA and underexpression of the protein", J Invest Dermatol 2002 119:1114-1120.
Clement et al., "Monoclonal antibodies against the interleukin-13 receptor α 1 and α 2", Cytokine 1997 9(11):959 Meeting Abstract.
Graber et al., "The distribution of IL-13 receptor α1 expression on B cells, T cells and monocytes and its regulation by IL-13 and IL-4", Eur. J. Immunol. 1998 28:4286-4298.
Hage et al., "Crystal structure of the interleukin-4/receptor α chain complex reveals α mosaic binding interface", Cell 1999 97(2):271-281.
Hilton et al., "Cloning and characterization of a binding subunit of the interleukin 13 receptor that is also a component of the interleukin 4 receptor", Proc Natl Acad Sci USA 1996 93:497-501.
Krause et al., "Blockade of interleukin-13-mediated cell activation by a novel inhibitory antibody to human IL-13 receptor α1", Molecular Immunology 2006 43:1799-1807.
Miloux et al., "Cloning of the human IL-13Rα1 chain and reconstitution with the IL-4Rα of a functional IL-4/IL-13 receptor complex", FEBS Letter 1997 401:163-166.
Ogata et al., "Regulation of interleukin-13 receptor constituents on mature human B lymphocytes", The Journal of Biological Chemistry 1998 273(16):9864-9871.
Poudrier et al., "A novel monoclonal antibody, C41, reveals IL-13Rα1 expression by murine germinal center B cells and follicular dendritic cells", Eur. J. Immunol. 2000 30:3157-31634.

(Continued)

*Primary Examiner* — Zachary Skelding
(74) *Attorney, Agent, or Firm* — Licata & Tyrrell, P.C.

(57) ABSTRACT

Antibody antagonists of human interleukin-13 receptor alpha 1 which bind to hIL-13Rα1 through domain 3 of the extracellular region of the receptor and inhibit IL-13 receptor-mediated signaling by IL-13 are disclosed herein. These antibodies have uses inter alia in the treatment or prevention of IL-13-related disorders and diseases. The present invention also discloses nucleic acid encoding said antibody molecules, vectors, host cells, and compositions comprising the antibody molecules. Methods of using the antibody molecules for inhibiting or antagonizing hIL-13Rα1-mediated activities are also disclosed.

9 Claims, 6 Drawing Sheets

(56) References Cited

OTHER PUBLICATIONS

Wells et al., Hematopoietic receptor complexes, Ann Rev Biochem 1996 65:609-634.

C. Vermont-Desroches et al., "Identification and characterization of Abs anti-IL-13Rα1 and IL-13Rα2", Tissue Antigents 2000 5(suppl):52-53 Meeting Abstract.

NCBI Accession No. NP_001551 [gi:4504647] with revision history—Mar. 19, 1999-Nov. 17, 2006.

NCBI Accession No. O09030 [gi:2494719] with revision history Feb. 1, 1997-Nov. 28, 2006.

NCBI Accession No. U62858 [gi:1695875] with revision history Dec. 1, 1996-Mar. 9, 2000.

NCBI Accession No. AAP78901 [gi:32264958] with revision history—Jul. 1, 2003.

NCBI Accession No. CAA78508 [gi:7345] with revision history Dec. 3, 1992-Apr. 18, 2005.

* cited by examiner

```
     TEvQPPVTNLSVSVENLCTiIWTWsPPEGASpNCtLrYFSHFdDgQDKKI
 51  APEThRkeElPLdEkICLQVGSQCSaNESEKPSpLVkKCISPPEGDPESA
101  VTELkCIWHNLSYMKCSWLPGRNTSPDThYTLYYWysSLEKsrQCENIyR
151  EGQhiaCSFkLTKVepSFEhqnVQIMVKDNAGKIrPSckIVsLTSyVKPD
201  PPHIKhLllkNgaLlVQWkNPQNFrSRCLtYEVEVNNtQTdrHNileVeE
                       HM3                HM4         HM5
251  dkCqNsEsdRNmEgTSCFglPGVLaDavyTVRvRVKTNKLCfdDnKLWSd
            HM7  HM8                                HM10
301  WSea CAGGTTCAGCTGGTGGAGTCTGGGGGAGGCGTGGTCCAGCCTGGGAGGTCCCTGAGACTCTCCTGT
Q  V  Q  L  V  E  S  G  G  G  V  V  Q  P  G  R  S  L  R  L  S  C
GCAGCCTCTGGATTCATCTTCAGTAGCTATGCACTGGTCCGCCAGGCTCCAGGCAAGGGG
A  A  S  G  F  I  F  S  S  Y  A  M  H  W  V  R  Q  A  P  G  K  G
                      <u>CDR1</u>
CTGGAGTGGTTGACAATTATATCAGATGATGGAAGCGATAAATACTACGCAGACTCCTTGAAGGGC
L  E  W  L  T  I  I  S  D  D  G  S  D  K  Y  Y  A  D  S  L  K  G
           <u>                        CDR2</u>
CGATTCACCATCTCCAGAGACAATTCCAAGAAGACGCTGTATCTGCAAATGAACAGCCTGAGAGTT
R  F  T  I  S  R  D  N  S  K  K  T  L  Y  L  Q  M  N  S  L  R  V
GAGGACACGGCTCTATATTACTGTGCGAGAGAGGGGGGACACTACTATTATAACGGTATGGACGTT
E  D  T  A  L  Y  Y  C  A  R  E  G  G  H  Y  Y  Y  N  G  M  D  V
                           <u>                                    CDR3</u>
GGGGCCAAGGGACCACGGTCACCGTCTCCTCAG (SEQ ID NO:21)
W  G  Q  G  T  T  V  T  V  S  S     (SEQ ID NO:4)

FIG. 2

CAAATACAGCTGGTGGAGTCTGGGGGAGGCCTGGTGGTCCCTGAGACTCTCCTGT
Q  I  Q  L  V  E  S  G  G  G  V  Q  P  G  R  S  L  R  L  S  C
GCAGCCTCTGGATTCACCTTCAGTAGCTATGCTATGCACTGGGTCCGCCAGGCTCCAGGCAAGGGG
A  A  S  G  F  T  F  S  S  Y  A  M  H  W  V  R  Q  A  P  G  K  G
                  CDR1
CTGGAGTGGGTGGCAGTTATATCAGATGATGGAAGCAATAAATACTACGCAGCCTCCGTGCAGGGC
L  E  W  V  T  I  I  S  D  D  G  S  N  K  Y  Y  A  A  S  V  Q  G
          CDR2
CGATTCACCATCTCCAGAGACAATTCCAAGAAGACGCTCTATCTGCAAATGAACAGCCTGAGAGCT
R  F  T  I  S  R  D  N  S  K  K  T  L  Y  L  Q  M  N  S  L  R  A
GAGGACACGGCCGTGTATTACTGTGCGAGAGAGGGGGATACTACTATTATAACGGTATGGACGTC
E  D  T  A  V  Y  Y  C  A  R  E  G  G  Y  Y  Y  Y  N  G  M  D  V
               CDR3
TGGGGCCAAGGGACCACGGTCACCGTCTCCTCA (SEQ ID NO:25)
W  G  Q  G  T  T  V  T  V  S  S    (SEQ ID NO:8)

FIG. 3

CAGGTGCAGCTGGTGGAGTCTGGGGGAGGCGTGGTCCAGCCTGGGAGGTCCCTGAGACTCTCCTGT
Q   V   Q   L   V   E   S   G   G   G   V   V   Q   P   G   R   S   L   R   L   S   C
GCAGCGTCTGGATTCACCTTCAGCAGTTATGGCATGCACTGGGTCCGCCAGGCTCCAGGCAAGGGG
A   A   S   G   F   T   F   S   S   Y   G   M   H   W   V   R   Q   A   P   G   K   G
                        CDR1
CTGGAGTGGGTGGCAGTTATATGGGATGATGGAAGTAATAAATACTATGAAGTCTCCGTGAAGGGC
L   E   W   V   A   V   I   W   D   D   G   S   N   K   Y   Y   E   V   S   V   K   G
                CDR2
CGATTCACCATCTCCAGAGACAATTCCAAGAACACGCTGTATCTTCAAATGAACAGCCTGAGAGTT
R   F   T   I   S   R   D   N   S   K   N   T   L   Y   L   Q   M   N   S   L   R   V
GAGGACACGGCTGTGTATTACTGTGCGAGAGATAGCAACAACTGGTACGTCGGTGTTTTTGATATC
E   D   T   A   V   Y   Y   C   A   R   D   S   N   N   W   Y   V   G   V   F   D   I
                                        CDR3
TGGGGCCAAGGGACAATGGTCACCGTCTCTTCA (SEQ ID NO:29)
W   G   Q   G   T   M   V   T   V   S   S    (SEQ ID NO:12)

FIG. 4

```
GAAATTGTGTTGACGCAGTCTCCAGGCACCCTGTCTTTGTCTCCAGGGGAAAGAGCCACCCTCTCC
 E  I  V  L  T  Q  S  P  G  T  L  S  L  S  P  G  E  R  A  T  L  S
TGCAGGGCCAGTCAGAGTGTTAGCAGCACCTACTTAGCCTGGTACCAGCAGAAACCTGGCCAGGCT
 C  R  A  S  Q  S  V  S  S  T  Y  L  A  W  Y  Q  Q  K  P  G  Q  A
                        ‾‾‾‾‾‾‾‾‾‾‾‾‾‾‾‾‾‾
                              CDR1
CCCAGGCTCCTCATCTATGGTGCATCCAGCAGGGCCACTGGCATCCCAGACACAGGTTCAGTGGCAGT
 P  R  L  L  I  Y  G  A  S  S  R  A  T  G  I  P  D  R  F  S  G  S
              ‾‾‾‾‾‾‾‾‾‾‾‾‾‾‾‾‾‾‾‾‾
                      CDR2
GGGTCTGGGACAGACTTCACTCTCACCATCAGCAGACTGGAGCCTGAAGATTTTGCAGTGTATTAC
 G  S  G  T  D  F  T  L  T  I  S  R  L  E  P  E  D  F  A  V  Y  Y
TGTCAGCAGTATGGTAGCTCACCATTCACTTTCGGCCCTGGGACCAAAGTGGATATCAAA  (SEQ ID NO:33)
 C  Q  Q  Y  G  S  S  P  F  T  F  G  P  G  T  K  V  D  I  K    (SEQ ID NO:16)
 ‾‾‾‾‾‾‾‾‾‾‾‾‾‾‾‾‾‾‾‾‾‾‾‾‾
          CDR3
```

FIG. 5

```
                |--- CH1 STARTS HERE
IgG1    LVTVSSASTK  GPSVFPLAPS  SKSTSGGTAA  LGCLVKDYFP  EPVTVSWNSG
IgG2    LVTVSSASTK  GPSVFPLAPC  SRSTSESTAA  LGCLVKDYFP  EPVTVSWNSG
IgG4    LVTVSSASTK  GPSVFPLAPC  SRSTSESTAA  LGCLVKDYFP  EPVTVSWNSG
IgG2M4  LVTVSSASTK  GPSVFPLAPC  SRSTSESTAA  LGCLVKDYFP  EPVTVSWNSG
        (VH-C1 LINKER)
                                                    C200
IgG1    ALTSGVHTFP  AVLQSSGLYS  LSSVVTVPSS  SLGTQTYICN  VNHKPSNTKV
IgG2    ALTSGVHTFP  AVLQSSGLYS  LSSVVTVTSS  NFGTQTYTCN  VDHKPSNTKV
IgG4    ALTSGVHTFP  AVLQSSGLYS  LSSVVTVPSS  SLGTKTYTCN  VDHKPSNTKV
IgG2M4  ALTSGVHTFP  AVLQSSGLYS  LSSVVTVTSS  NFGTQTYTCN  VDHKPSNTKV

-HINGE REGION--||----CH2-> P238         M252      C261
IgG1    DKKAEPKSCD  KTHTCPPCPA  PELLGGPSVF  LFPPKPKDTL  |MISRTP|EVTC
IgG2    DKTVERKCC-  --VECPPCPA  PP-VAGPSVF  LFPPKPKDTL  |MISRTP|EVTC
IgG4    DKRVESKYGP  ---PCPSCPA  PEFLGGPSVF  LFPPKPKDTL  |MISRTP|EVTC
IgG2M4  DKTVERKCC-  --VECPPCPA  PP-VAGPSVF  LFPPKPKDTL  |MISRTP|EVTC
                    (LOWER HINGE)                        FcRn-BIND

D265 D270                            N297*      T307
IgG1    VVV|DVSHED|P  EVKFNWYVDG  VEVHNAKTKP  REEQY|NST|YR  VVSVL|TVLHQ|
IgG2    VVV|DVSHED|P  EVQFNWYVDG  VEVHNAKTKP  REEQF|NST|FR  VVSVL|TVVHQ|
IgG4    VVV|DVSQED|P  EVQFNWYVDG  VEVHNAKTKP  REEQF|NST|YR  VVSVL|TVLHQ|
IgG2M4  VVV|DVSQED|P  EVQFNWYVDG  VEVHNAKTKP  REEQF|NST|FR  VVSVL|TVLHQ|
        B/C LOOP                              C'E LOOP    FcRn-BIND

C321       P329               |----CH3->
IgG1    DWLNGKEYKC  KVSNK|ALPAPI|  EKTISKAKG  QPREPQVYTL  PPSRDELTKN
IgG2    DWLNGKEYKC  KVSNK|GLPAPI|  EKTISKTKG  QPREPQVYTL  PPSREEMTKN
IgG4    DWLNGKEYKC  KVSNK|GLPSSI|  EKTISKAKG  QPREPQVYTL  PPSQEEMTKN
IgG2M4  DWLNGKEYKC  KVSNK|GLPSSI|  EKTISKTKG  QPREPQVYTL  PPSREEMTKN
              F/G LOOP

IgG1    QVSLTCLVKG  FYPSDIAVEW  ESNGQPENNY  KTTPPVLDSD  GSFFLYSKLT
IgG2    QVSLTCLVKG  FYPSDIAVEW  ESNGQPENNY  KTTPPMLDSD  GSFFLYSKLT
IgG4    QVSLTCLVKG  FYPSDIAVEW  ESNGQPENNY  KTTPPVLDSD  GSFFLYSRLT
IgG2M4  QVSLTCLVKG  FYPSDIAVEW  ESNGQPENNY  KTTPPMLDSD  GSFFLYSKLT

H433
IgG1    VDKSRWQQGN  VFSCSVMHEA  L|HNHY|TQKSL  SLSPGK*  (SEQ ID NO:38)
IgG2    VDKSRWQQGN  VFSCSVMHEA  L|HNHY|TQKSL  SLSPGK*  (SEQ ID NO:39)
IgG4    VDKSRWQEGN  VFSCSVMHEA  L|HNHY|TQKSL  SLSLGK*  (SEQ ID NO:40)
IgG2M4  VDKSRWQQGN  VFSCSVMHEA  L|HNHY|TQKSL  SLSPGK*  (SEQ ID NO:41)
                              FcRn-BIND
```

FIG. 6

ANTI-IL-13Rα1 ANTIBODIES AND THEIR USES THEREOF

This application claims benefit of PCT/US2007/081884, filed Oct. 19, 2007, which claims benefit of U.S. provisional patent application Ser. No. 60/852,780 filed Oct. 19, 2006, the contents of which are incorporated herein by reference in their entireties.

BACKGROUND OF THE INVENTION

Interleukin-13 (IL-13) is involved in the induction of IgE and IgG4 production, as well as the differentiation of T-helper (Th) cells into a secretory (Th2) phenotype. These immunostimulatory steps are critical in the development of atopic diseases which are a major threat to human health, such as anaphylaxis (Howard et al, *Am J Hum Genet* 70(1):230-236, 2002; Noguchi et al, *Hum Immunol* 62(11):1251-1257, 2001), as well as milder conditions such as hay fever, allergic rhinitis and chronic sinusitis which, although not life-threatening, are responsible for considerable morbidity worldwide.

IL-13 is a mediator in the pathology of the acute and chronic stages of asthma. During an asthma attack, its expression increases and its effects include reduction of the capacity of lung epithelial cells to maintain a tight barrier against inhaled particles and pathogens (Ahdieh et al, *Am J. Physiol. Cell Physiol.* 281(6):C2029-2038, 2000) and promotion of allergen-induced airway hyper-responsiveness (Morse et al, *Am. J. Physiol. Lung Cell Mol. Physiol.* 282(1):L44-49, 2002). In the longer term, IL-13 promotes non-inflammatory structural changes to asthmatic airways, such as enhanced expression of mucin genes, airway damage and obstruction of the small airways (Howard et al, 2002, supra; Danahay et al, *Am. J. Physiol. Lung Cell Mol. Physiol.* 282(2):L226-236, 2002).

The biological effects of IL-13 are mediated by a dimeric receptor complex including the subunits IL-13Rα1 and IL-4Rα. It is postulated that IL-13 binding to IL-13Rα1 triggers dimerization with IL-4Rα and activation of intracellular mediators that include the Janus Kinases JAK1 and JAK2, as well as STAT6, ERK and p38 (David et al, *Oncogene* 20(46): 6660-6668, 2001; Perez et al, *J. Immunol.* 168(3):1428-1434, 2002).

IL-13 shows many overlapping biological effects with those of IL-4. IL-13 and IL-4 are related by sequence and are involved in many related processes, such as myelopoiesis and the regulation of monocyte/macrophage pro-inflammatory functions. For example, both IL-13 and IL-4 have been shown to effect B cells in a similar fashion, up-regulating surface molecules such as MHC class II and CD23 molecules, and promoting the secretion of IgG4 and IgE.

The overlapping activities of IL-13 and IL-4 can be explained in part by their shared dimeric receptor complex. The IL-13 receptor complex is composed of an IL-13Rα1 and an IL-4Rα; this same receptor complex is also the Type II IL-4 receptor complex (Callard et al, *Immunology Today* 17(3):108, 1996). As such, in looking to achieve therapeutic control of the IL-13 receptor complex by blocking cytokine-mediated signaling, it may be useful to have not only a molecule that inhibits signaling mediated by IL-13, but a molecule that inhibits signaling mediated by both IL-13 and IL-4.

Gauchat et al (*Eur. J. Immunol.* 28:4286-4298, 1998) reported murine antibodies to human IL-13Rα1 which blocked interaction of a tagged IL-13 with a tagged and immobilized soluble IL-13Rα1. These antibodies also inhibited IL-13 binding to IL-13Rα1 in transfected HEK-293 cells. However, all of these antibodies failed to neutralize IL-13-induced biological activity, suggesting that they were not antagonists of the complete IL-13Rα1/IL-4Rα receptor complex. In a later paper, Gauchat et al (*Eur. J. Immunol.* 30:3157-3164, 2000) reported a rat antibody, designated as C41, to murine IL-13Rα1 which bound to HEK-293 cells transfected with murine IL-13Rα1. However, C41 did not neutralize IL-13-induced biological activities. Further, C41 did not react with the soluble form of human IL-13Rα1. Akaiwa et al (*Cytokine* 13:75-84, 2001) reported an antibody that recognized soluble IL-13Rα1 by enzyme immunoassay and a tagged full-length IL-13Rα1 transfected into COS7 cells. The antibody was used for immunohistochemistry but there is no indication that it was a neutralizing antibody.

WO 03/46009 teaches murine antibodies to human IL-13Rα1 which inhibited TF-1 cell response to IL-13 but not to IL-4, and Krause et al (*Mol Immunol.* 43(11):1799-807, 2006) describe murine antibodies to human IL-13Rα1 which inhibit IL-13-dependant TF-1 cell proliferation. Antibodies to hIL-13Rα1 are also known from WO 97/15663, WO 03/080675, WO 06/072564 and Vermot-Desroches et al., 2000 *Tissue Antigens* 5(Supp. 1):52-53 (Meeting Abstract).

Despite these reports, there remains a need for antibodies to human IL-13Rα1 that are suitable for administration to humans and that block IL-13 activity.

SUMMARY OF THE INVENTION

The present invention is generally directed to isolated antibodies, in particular human, humanized, deimmunized, chimeric or primatized monoclonal antibodies, that bind to hIL-13Rα1 through domain 3 of the extracellular region of the receptor. Specifically, an antibody of the present invention binds through one or more of amino acid residues 248-252 of hIL-13Rα1.

In one embodiment, the present invention provides an isolated monoclonal antibody which binds to hIL-13Rα1 through domain 3 of the extracellular region of the receptor and inhibits IL-13 signaling. In another embodiment of the present invention, the monoclonal antibody exhibits at least one of the following functional properties: (i) inhibits IL-13-induced eotaxin release in NHDF cells; (ii) inhibits IL-4-induced eotaxin release in NHDF cells; (iii) inhibits IL-13-induced STAT6 phosphorylation in NHDF cells; or (iv) inhibits IL-4-induced STAT6 phosphorylation in NHDF cells.

In a specific embodiment, a substitution mutation in a peptide of domain 3 of hIL-13Rα1 of the residues Val-Phe-Tyr-Val-Gln (SEQ ID NO:44) that correspond to positions 248-252 of SEQ ID NO:1 with the residues Ile-Leu-Glu-Val-Glu (SEQ ID NO:45) leads to a loss of binding between the antibody and the resultant mutant hIL-13Rα1 peptide compared to the binding between the antibody and the hIL-13Rα1 peptide without the substitution mutation.

In another embodiment, a substitution mutation in a peptide including domain 3 of hIL-13Rα1 of any one of: the phenylalanine residue that corresponds to position 249 of SEQ ID NO:1 with an alanine residue; the tyrosine residue that corresponds to position 250 of SEQ ID NO:1 with an alanine residue; the glutamine residue that corresponds to position 252 of SEQ ID NO:1 with an alanine residue; wherein said mutation leads to a loss of binding between the antibody and the resultant mutant hIL-13Rα1 peptide compared to the binding between the antibody and the hIL-13Rα1 peptide without the substitutions.

One group of antibodies of the present invention is the human monoclonal antibodies 4B5, 8B11 and 15F4. In particular, such antibodies contain a heavy chain variable region having an amino acid sequence as set forth in SEQ ID NO:4, SEQ ID NO:8 and SEQ ID NO:12.

Other antibodies of the invention include CDR3 sequences of 4B5, 8B11 and 15F4 or conservative sequence modifications thereof or homologs thereof. Heavy chain variable region CDR1, CDR2, and CDR3 amino acid sequences particularly embraced by the present invention are set forth in: (i) SEQ ID NOS:5, 6 and 7, respectively; (ii) SEQ ID NOS:9, 10 and 11, respectively; or (iii) SEQ ID NOS:13, 14 and 15, respectively. Light chain variable region CDR1, CDR2 and CDR3 sequences particularly embraced by the present invention are set forth in: SEQ ID NOS:17, 18 and 19, respectively. Other antibodies of the subject invention include sets of heavy and/or light chain CDR sequences of 4B5, 8B11 and 15F4 or conservative sequence modifications thereof or homologs thereof. Other antibodies of the present invention encompass heavy and/or light chain variable region sequences of 4B5, 8B11 and 15F4 or conservative sequence modifications thereof or homologs thereof. Antibodies specifically embraced by the invention include those produced by hybridoma cell lines such as ATCC Deposit PTA6931, ATCC Deposit PTA6936 and ATCC Deposit PTA6935.

In another aspect, the subject invention provides antibodies that compete for binding to hIL-13Rα1 with any of 4B5, 8B11 or 15F4.

The antibodies of the subject invention include, for example, full-length antibodies, such as an IgG1 or IgG4 isotype. Alternatively, the antibodies are antibody fragments, such as Fab or Fab'2 fragments, or single chain antibodies.

In specific embodiments, antibodies of the present invention are human antibodies. Alternatively, the antibodies are humanized, primatized, deimmunized, or chimeric antibodies.

The present invention also provides an immunoconjugate including an antibody of the subject invention linked to a therapeutic agent, such as a cytotoxin or a radioactive isotope. The present invention also provides a bispecific molecule including an antibody of the instant invention, linked to a second functional moiety having a different binding specificity than the antibody.

Compositions including an antibody or immunoconjugate or bispecific molecule of the present invention and a pharmaceutically acceptable carrier are also provided.

Nucleic acid molecules encoding the antibodies of the instant invention are also encompassed herein, as well as expression vectors contains such nucleic acids and host cells harboring such expression vectors.

In another aspect the invention provides methods of identifying antibodies capable of binding to hIL-13Rα1 through domain 3 of the extracellular region of the receptor.

Another aspect of the invention provides a method for inhibiting IL-13 receptor-mediated signaling by contacting a cell expressing IL-13Rα1 with an antibody of the present invention under conditions that allow said antibody to bind to IL-13Rα1.

In yet another aspect, the invention provides a method of treating an IL-13-related disease or disorder in a subject in need of treatment by administering to the subject the antibody of the present invention, such that the IL-13-associated disease or disorder in the subject is treated. The disease or disorder includes, for example, asthma, COPD, atopic dermatitis, allergic rhinitis, esophagal eosinophilia, Hodgkin's lymphoma, inflammatory bowel disease, psoriasis, psoriatic arthritis and fibrosis.

Other features and advantages of the instant invention will be apparent from the following detailed description and examples which should not be construed as limiting.

BRIEF DESCRIPTION OF THE DRAWINGS

FIG. 1 is a representation of the extracellular region of mouse IL-13Rα1 with amino acids that differ from those of the human sequence shown in lower case. A panel of human/mouse chimeric IL-13Rα1 proteins, displayed on phage, were prepared by systematically replacing single identified segments of the human IL-13Rα1 extracellular region with the corresponding underlined segment of mouse-derived sequence (i.e., HM1 through HM11).

FIG. 2 is a representation of the nucleotide and derived amino acid sequence of the heavy chain variable region of antibody 4B5. CDRs and nucleic acid encoding CDRs are underlined.

FIG. 3 is a representation of the nucleotide and derived amino acid sequence of the heavy chain variable region of antibody 8B11. CDRs and nucleic acid encoding CDRs are underlined.

FIG. 4 is a representation of the nucleotide and derived amino acid sequence of the heavy chain variable region of antibody 15F4. CDRs and nucleic acid encoding CDRs are underlined.

FIG. 5 is a representation of the nucleotide and derived amino acid sequence of the light chain variable region of antibody 15F4. CDRs and nucleic acid encoding CDRs are underlined.

FIG. 6 is a sequence comparison of the Fc domains of IgG1 (SEQ ID NO:38), IgG2 (SEQ ID NO:39), IgG4 (SEQ ID NO:40) and the IgG2 m4 (SEQ ID NO:41) isotypes.

DETAILED DESCRIPTION OF THE INVENTION

The present invention relates to isolated antibodies, particularly human monoclonal antibodies, that bind to human IL-13Rα1 through domain 3 of the extracellular region of the receptor, and which inhibit certain functional properties of IL-13Rα1. Reference to the instant "monoclonal antibodies" includes humanized, deimmunized and chimeric forms thereof as well as primatized forms. In certain embodiments, the antibodies of the present invention include particular structural features such as CDR regions having particular amino acid sequences. The present invention provides isolated antibodies, methods of making such antibodies, immunoconjugates and bispecific molecules including such antibodies and pharmaceutical compositions containing the antibodies, immunconjugates or bispecific molecules of the invention. The subject invention also relates to methods of using the antibodies to inhibit IL-13 responses, for example in the treatment of various IL-13 related disorders and diseases including asthma, COPD, atopic dermatitis, allergic rhinitis, esophagal eosinophilia, Hodgkin's lymphoma, inflammatory bowel disease, psoriasis, psoriatic arthritis and fibrosis.

The extracellular region of hIL-13Rα is predicted to consist of 3 fibronectin type III globular domains, each approximately 100 amino acids in length (Arima et al, *J. Biol. Chem.* 280(26):24915-22, 2005). The amino terminal fibronectin type III domain (referred to here as domain 1 or D1) is followed by two other fibronectin type III domains (referred to here as domain 2 and domain 3, or D2 and D3, respectively) which have a cytokine receptor homology module (Wells and de Vos, *Ann. Rev. Biochem.* 65:609-34, 1996). To predict the sequence boundaries of each of these fibronectin type III domains, the mature sequences of the extracellular regions of hIL-13Rα1 and hIL-4Rα were aligned. The approximately 200 residue extracellular region of hIL-4Rα consists of a cytokine receptor homology module, corresponding to D2 and D3 of IL-13Rα1, but does not contain any upstream domain corresponding to D1. Accordingly, the first residue of mature hIL-4Rα was taken to define the boundary between D1 and D2 on the aligned hIL-13Rα1 sequence. The boundary between the two fibronectin type III domains in IL-4Rα, as deduced from the crystal structure (Hage et al, *Cell*, 97(2): 271-81, 1999), was then used to define the boundary between D2 and D3 in the aligned IL-13Rα1 sequence. Accordingly, domain 1 of extracellular region of hIL-13Rα1 corresponds to amino acids 1 to 100 of SEQ ID NO:1, domain 2 to amino acids 101 to 200 of SEQ ID NO:1, and domain 3 to amino acids 201 to 317 of SEQ ID NO:1. Domain 3 is also set forth herein as SEQ ID NO:37.

In accordance with the present invention, antibodies are generated which bind to hIL-13Rα1 through domain 3 of the extracellular region of the receptor chain and which inhibit IL-13 signaling through the IL-13Rα1/IL-4Rα complex. Such antibodies inhibit IL-13-mediated biological activity. In a specific embodiment, some antibodies of the present invention inhibit signaling by both IL-13 and IL-4 through the IL-13Rα1/IL-4Rα complex.

For the purposes of the present invention, the terms "interleukin 13 receptor alpha 1" and "IL-13Rα1" are used interchangeably, and may include variants, isoforms and species homologs of human IL-13Rα1. Accordingly, human antibodies of the present invention may, in certain cases, cross-react with IL-13Rα1 from species other than human. In other cases, the antibodies may be specific for human IL-13Rα1 and may not exhibit species or other types of cross-reactivity. The amino acid sequence of human IL-13Rα1 (also referred to as hIL-13Rα1) has GENBANK accession number NP_001551 and the mature form of the protein, i.e., without the signal sequence, is set forth herein as SEQ ID NO:1. The amino acid sequence of cynomolgus monkey IL-13Rα1 has GENBANK accession number AAP78901 and the mature form of the protein is set forth herein as SEQ ID NO:2. The amino acid sequence of mouse IL-13Rα1 (also referred to as mL-13Rα1) has GENBANK accession number O09030 and the mature form of the protein is set forth herein as SEQ ID NO:3.

Other sequences embraced by the present invention are provided in Table 1.

TABLE 1

| SEQ ID NO: | Description |
| --- | --- |
| 1 | Mature human IL-13Rα1 |
| 2 | Mature cynomolgus monkey IL-13Rα1 |
| 3 | Mature mouse IL-13Rα1 |
| 4 | 4B5 VH |
| 5 | 4B5 VH CDR1 |
| 6 | 4B5 VH CDR2 |
| 7 | 4B5 VH CDR3 |
| 8 | 8B11 VH |
| 9 | 8B11 VH CDR1 |
| 10 | 8B11 VH CDR2 |
| 11 | 8B11 VH CDR3 |
| 12 | 15F4 VH |
| 13 | 15F4 VH CDR1 |
| 14 | 15F4 VH CDR2 |
| 15 | 15F4 VH CDR3 |
| 16 | 15F4 VL |
| 17 | 15F4 VL CDR1 |
| 18 | 15F4 VL CDR2 |
| 19 | 15F4 VL CDR3 |
| 20 | N-terminal FLAG ®-tagged hIL-13Rα1.ECR |
| 21 | 4B5 VH nucleic acid |
| 22 | 4B5 VH CDR1 nucleic acid |
| 23 | 4B5 VH CDR2 nucleic acid |
| 24 | 4B5 VH CDR3 nucleic acid |

TABLE 1-continued

| SEQ ID NO: | Description |
| --- | --- |
| 25 | 8B11 VH nucleic acid |
| 26 | 8B11 VH CDR1 nucleic acid |
| 27 | 8B11 VH CDR2 nucleic acid |
| 28 | 8B11 VH CDR3 nucleic acid |
| 29 | 15F4 VH nucleic acid |
| 30 | 15F4 VH CDR1 nucleic acid |
| 31 | 15F4 VH CDR2 nucleic acid |
| 32 | 15F4 VH CDR3 nucleic acid |
| 33 | 15F4 VL nucleic acid |
| 34 | 15F4 VL CDR1 nucleic acid |
| 35 | 15F4 VL CDR2 nucleic acid |
| 36 | 15F4 VL CDR3 nucleic acid |
| 37 | D3 of the extracellular region of hIL-13Rα1 |
| 38 | Contains Fc domain of IgG1 |
| 39 | Contains Fc domain of IgG2 |
| 40 | Contains Fc domain of IgG4 |
| 41 | Contains Fc domain of IgG2m4 |
| 42 | Fc domain of IgG2m4 |
| 43 | Fc domain of IgG2m4 nucleic acid |
| 44 | Domain 3 peptide of wild-type hIL-13Rα1 |
| 45 | Mutant domain 3 peptide of wild-type hIL-13Rα1 |
| 46 | Extracellular region of mIL-13Rα1 |

The term "antibody", as referred to herein, includes whole antibodies (also known as full-length antibodies) and any antigen binding fragment (i.e., "antigen-binding portion") thereof. A "whole antibody" refers to a protein comprising two heavy (H) chains and two light (L) chains inter-connected by disulfide bonds. Each heavy chain is composed of a heavy chain variable region (abbreviated herein as $V_H$) and a heavy chain constant region. The heavy chain constant region is composed of three domains, $C_{H1}$, $C_{H2}$ and $C_{H3}$. Each light chain is composed of a light chain variable region (abbreviated herein as $V_L$) and a light chain constant region. The light chain constant region is composed of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody, as used herein, refers to one or more fragments of an antibody that retain the ability to bind to hIL-13Rα1. It has been shown that the antigen-binding function of an antibody can be performed by fragments of a full-length antibody. Examples of binding fragments encompassed within the term "antigen-binding portion" of an antibody include (i) a Fab fragment, a monovalent fragment composed of the $V_L$, $V_H$, $C_L$ and $C_{H1}$ domains; (ii) a F(ab')$_2$ fragment, a bivalent fragment composed of two Fab fragments linked by a disulfide bridge at the hinge region; (iii) a Fd fragment composed of the $V_H$ and $C_{H1}$ domains; (iv) a Fv fragment composed of the $V_L$ and $V_H$ domains of a single arm of an antibody, (v) a dAb fragment (Ward et al, *Nature* 341:544-546, 1989), which is composed of either a $V_H$ or a $V_L$ domain (Holt et al, *Trends in Biotechnology*, 21:484-489, 2003); and (vi) an isolated complementarity determining region (CDR), in particular CDR3 of a $V_H$. As will be appreciated by those skilled in the art fragments of an antibody that retain the ability to bind to hIL-13Rα1 may be inserted into various frameworks, see for example U.S. Pat. No. 6,818,418, and references contained therein, which discuss various scaffolds which may be used to display antibody loops previously selected on the basis of antigen binding. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al, *Science* 242:423-426, 1988 and Huston et al, *Proc. Natl. Acad. Sci. USA* 85:5879-5883, 1988). Such single chain antibodies are also intended to be encompassed within the term "antigen-binding portion" of an antibody. These antibody fragments may be obtained using conventional techniques known to those with skill in the art, and may be produced without having first produced a full-length antibody. Fragments may be screened for relevant properties in the same manner as are full-length antibodies.

An "isolated antibody", as used herein, is intended to refer to an antibody that is substantially free of other antibodies having different antigenic specificities (e.g., an isolated antibody that binds hIL-13Rα1 is substantially free of antibodies that bind antigens other than IL-13Rα1). An isolated antibody that binds hIL-13Rα1 may, however, have cross-reactivity to other antigens, such as IL-13Rα1 molecules from other species. Moreover, an isolated antibody may be substantially free of other cellular material and/or chemicals.

The term "monoclonal antibody" or "mAb" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. A monoclonal antibody that is also an isolated antibody may be referred to as an isolated monoclonal antibody.

The term "human antibody", as used herein, is intended to include antibodies having variable regions derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and, in particular, CDR3 and thus the amino acid sequences of the $V_L$ and/or $V_H$ regions of the antibodies are sequences that, while derived from and related to human germline $V_L$ and $V_H$ sequences, may not naturally exist within the human antibody germline repertoire in vivo. However, the term "human antibody", as used herein, is not intended to include antibodies in which CDR sequences derived from another mammalian species, such as a mouse, have been grafted onto human framework sequences, i.e., a humanized antibody.

As used herein, domain 3 of the extracellular region of hIL-13Rα1 corresponds to amino acids 201 to 317 of SEQ ID NO:1 and is set forth herein as SEQ ID NO:37. Accordingly, an antibody that binds to hIL-13Rα1 through domain 3 of the extracellular region of the receptor is one that shows binding to a peptide consisting essentially of the domain 3 amino acid residues noted above; for example the domain 3 constructs displayed on phage in Example 3, where binding was determined by ELISA. Those skilled in the art will realize there are other methods of determining binding to domain 3 of the extracellular region of hIL-13Rα1, for example by BIA-CORE™ (PHARMACIA AB Corporation) analysis. An antibody that binds to hIL-13Rα1 through domain 3 of the extracellular region of the receptor will also bind to the full-length receptor and other receptor-derived peptides including SEQ ID NO:37; for example the hIL-13Rα1.ECR peptide of Example 1 which includes domains 1, 2 and 3 of the extracellular region of the receptor.

As used herein, an antibody that "binds to human IL-13Rα1" is intended to refer to an antibody that binds to human IL-13Rα1 with a $K_D$ of $5 \times 10^{-9}$ M or less, more preferably $2 \times 10^{-9}$ M or less, and even more preferably $1 \times 10^{-9}$ M or less. Related phrases such as "the antibodies bind to human IL-13Rα1" have the same meaning. An antibody that "cross-reacts with cynomolgus monkey IL-13Rα1" is intended to refer to an antibody that binds to cynomolgus monkey IL-13Rα1 with a $K_D$ of $5 \times 10^{-9}$ M or less, and even more preferably $2 \times 10^{-9}$ M or less. An antibody that "does not cross-react with mouse IL-13Rα1" is intended to refer to an antibody that binds to mouse IL-13Rα1 with a $K_D$ of $1 \times 10^{-7}$ M or greater. In certain embodiments, antibodies that do not cross-react with mouse IL-13Rα1 exhibit essentially undetectable binding against this protein in standard binding assays.

The term "$K_a$", as used herein, is intended to refer to the association rate of a particular antibody-antigen interaction, whereas the term "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well-established in the art. A preferred method for determining the $K_D$ of an antibody is by using surface plasmon resonance, preferably using a biosensor system such as a BIACORE™ system.

Various aspects of the present invention are described in further detail in the following subsections.

Anti-hIL-13Rα1 Antibodies.

The antibodies of the present invention are characterized by particular functional features or properties of the antibodies. For example, the antibodies bind to human IL-13Rα1 through domain 3 of the extracellular region of the receptor.

Additionally, the antibodies of the present invention may or may not cross-react with IL-13Rα1 from one or more non-human primates, such as cynomolgus monkey. Accordingly, in one embodiment, the antibodies of the subject invention cross-react with cynomolgus IL-13Rα1.

In another embodiment, the antibodies of the present invention do not cross-react with mouse IL-13Rα1.

In specific embodiments, an antibody of the present invention binds to IL-13Rα1 with high affinity, for example with a $K_D$ of $5 \times 10^{-9}$ M or less, more preferably $2 \times 10^{-9}$ M or less, and even more preferably $1 \times 10^{-9}$ M or less.

Furthermore, the antibodies of the present invention are capable of inhibiting one or more functional activities of hIL-13Rα1. For example, in one embodiment, the antibodies may inhibit IL-13-induced eotaxin release in NHDF cells. In yet another embodiment, the antibodies may inhibit IL-13- induced STAT6 phosphorylation in NHDF cells. In yet another embodiment, the antibodies may inhibit IL-4-induced eotaxin release in NHDF cells. In yet another embodiment, the antibodies may inhibit IL-4-induced STAT6 phosphorylation in NHDF cells. In specific embodiments, the antibodies inhibit all of the above functional activities of hIL-13Rα1.

Antibodies of the instant invention may or may not inhibit the binding of IL-13 to isolated IL-13Rα1 (i.e., IL-13Rα1 that is not part of a dimeric receptor with IL-4Rα). Some antibodies of the invention may not inhibit binding of IL-13 to isolated IL-13Rα1 but nevertheless may inhibit IL-13-induced responses in NHDF cells mediated through the Type I IL-13 receptor complex.

One group of antibodies of the subject invention include those that inhibit the binding of hIL-13 to isolated hIL-13Rα1.

Another group of antibodies of the present invention are full-length antibodies.

In specific embodiments, the antibodies of the present invention are human antibodies. In another embodiment said antibodies are humanized, deimmunized, primatized or chimeric antibodies.

Antibodies of the subject invention may be of any antibody isotype, e.g., IgG, IgA, IgE and IgM and any of the isotype sub-classes, particularly IgG1 and IgG4. IgG4 is typically preferred because it does not bind complement and does not create effector functions. Any synthetic or other constant region variant that has these or other desirable properties is also preferred for use in embodiments of the present invention.

Standard assays to evaluate the binding ability of the antibodies toward IL-13Rα1 of various species are known in the art, including for example, ELISAs, western blots and RIAs. Examples of suitable assays are also described in the Examples. The binding kinetics (e.g., binding affinity) of the antibodies also can be assessed by standard assays known in the art, such as by BIACORE™ analysis. Examples of assays to evaluate the effects of the antibodies on functional properties of IL-13Rα1 (e.g., ligand binding, inhibition of IL-13-induced activity in cells) are described in the Examples.

Accordingly, an antibody that "inhibits" one or more of these IL-13Rα1 functional properties as determined according to methodologies known to the art and described herein, will be understood to relate to a decrease in the particular activity relative to that seen in the absence of the antibody (e.g., or when a control antibody of irrelevant specificity is present). Preferably an antibody that inhibits an IL-13 and/or an IL-4 activity effects such a decrease by at least 10% of the measured parameter, more preferably by at least 20%, 30%, 40%, 50%, 60%, 70%, 80%, 90% or 95%.

In one embodiment, the present invention provides an isolated monoclonal antibody which binds to IL-13Rα1 through domain 3 of the extracellular region of the receptor and inhibits IL-13 signaling. In specific embodiments, the instant invention also exhibits at least one of the following functional properties: (i) inhibits IL-13-induced eotaxin release in NHDF cells; (ii) inhibits IL-4-induced eotaxin release in NHDF cells; (iii) inhibits IL-13-induced STAT6 phosphorylation in NHDF cells; or (iv) inhibits IL-4-induced STAT6 phosphorylation in NHDF cells.

In a specific embodiment, a substitution mutation in a peptide including domain 3 of hIL-13Rα1 of the residues Val-Phe-Tyr-Val-Gln (SEQ ID NO:44), which correspond to positions 248-252 of SEQ ID NO:1, with the residues Ile-Leu-Glu-Val-Glu (SEQ ID NO:45) leads to a loss of binding between an antibody of the invention and the resultant mutant hIL-13Rα1 peptide compared to the binding between said antibody and the hIL-13Rα1 peptide without said substitutions.

In another embodiment, a substitution mutation in a peptide including domain 3 of hIL-13Rα1 of any one of: the phenylalanine residue that corresponds to position 249 of SEQ ID NO:1 with an alanine residue; the tyrosine residue that corresponds to position 250 of SEQ ID NO:1 with an alanine residue; or the glutamine residue that corresponds to position 252 of SEQ ID NO:1 with an alanine residue; leads to a loss of binding between an antibody of the present invention and the resultant mutant hIL-13Rα1 peptide compared to the binding between said antibody and the hIL-13Rα1 peptide without said substitutions.

Monoclonal Antibodies 4B5, 8B11 and 15F4.

A group of anti-hIL-13Rα1 antibodies of the present invention are the human monoclonal antibodies 4B5, 8311 and 15F4, isolated and structurally characterized as described in the Examples. The heavy chain variable region amino acid sequences of 4B5, 8B11 and 15F4, and the corresponding CDR1, CDR2, and CDR3 sequences are as tabulated below in Table 2. Similarly, the light chain variable region amino acid sequence of 15F4, and the corresponding CDR1, CDR2, and CDR3 sequences are as tabulated below. The CDR regions are delineated using the Kabat system (Kabat et al, *Sequences of Proteins of Immunological Interest*, Fifth Edition, U.S. Department of Health and Human Services, NIH Publication No. 91:3242, 1991), except for $V_H$ CDR1, which is extended to encompass both sequence and structural (Chothia and Lesk, *J. Mol. Biol.* 196:901-917, 1987) definitions, viz. $V_H$ residues 26-35.

TABLE 2

| Sequence | SEQ ID NO: |
| --- | --- |
| 4B5 VH | 4 |
| 4B5 VH CDR1 | 5 |
| 4B5 VH CDR2 | 6 |
| 4B5 VH CDR3 | 7 |
| 8B11 VH | 8 |
| 8B11 VH CDR1 | 9 |
| 8B11 VH CDR2 | 10 |
| 8B11 VH CDR3 | 11 |
| 15F4 VH | 12 |
| 15F4 VH CDR1 | 13 |
| 15F4 VH CDR2 | 14 |
| 15F4 VH CDR3 | 15 |
| 15F4 VL | 16 |
| 15F4 VL CDR1 | 17 |
| 15F4 VL CDR2 | 18 |
| 15F4 VL CDR3 | 19 |

The CDR regions of antibodies are known to determine antigen recognition, and CDR3 is of particular importance. Thus in another aspect, the subject invention provides an isolated monoclonal antibody including a CDR3 sequence selected from the group consisting of SEQ ID NOs:7, 11, 15 and a conservative sequence modification thereof, which: a) binds to hIL-13Rα1 through domain 3 of the extracellular region of the receptor, and b) exhibits at least one of the following functional properties: (i) inhibits IL-13-induced eotaxin release in NHDF cells; (ii) inhibits IL-4-induced eotaxin release in NHDF cells; (iii) inhibits IL-13-induced STAT6 phosphorylation in NHDF cells; or (iv) inhibits IL-4-induced STAT6 phosphorylation in NHDF cells.

In a specific embodiment, such antibodies include a heavy chain variable region wherein CDR1, CDR2, and CDR3 sequences are: (a) SEQ ID NOs:5, 6 and 7, respectively; (b) SEQ ID NOs:9, 10 and 11, respectively; (c) SEQ ID NOs:13, 14 and 15, respectively; or (d) a set of such CDR sequences as set out in (a), (b) or (c) with conservative sequence modifications in any one or more of said CDR sequences.

In a further embodiment, the heavy chain variable region CDR1, CDR2, and CDR3 sequences are as set forth in SEQ ID NOs:5, 6 and 7, respectively.

In another further embodiment, the heavy chain variable region CDR1, CDR2, and CDR3 sequences are as set forth in SEQ ID NOs:9, 10 and 11, respectively.

In another further embodiment, the heavy chain variable region CDR1, CDR2, and CDR3 sequences are as set forth in SEQ ID NOs:13, 14 and 15, respectively.

In another aspect, the present invention provides an isolated monoclonal antibody including a light chain variable region comprising a CDR3 sequence selected from the group consisting of SEQ ID NO:19 and a conservative sequence modification thereof, which: (a) binds to hIL-13Rα1 through domain 3 of the extracellular region of the receptor, and (b) exhibits at least one of the functional properties (i) through (iv) noted above.

In specific embodiments, such antibodies include a light chain variable region wherein CDR1, CDR2, and CDR3 sequences are as set forth in SEQ ID NOs:17, 18 and 19, respectively or a set of such CDR sequences with conservative sequence modifications in any one or more of said CDR sequences.

In a further embodiment, the light chain variable region CDR1, CDR2, and CDR3 sequences are as set forth in SEQ ID NOs:17, 18 and 19, respectively.

In another aspect, the subject invention provides an isolated monoclonal antibody including a heavy chain variable region CDR3 sequence and a light chain variable region CDR3 sequence as set forth in SEQ ID NOs:15 and 19, respectively, or conservative sequence modifications in any one or more of said CDR3 sequences, which: (a) binds to hIL-13Rα1 through domain 3 of the extracellular region of the receptor, and (b) exhibits at least one of the functional properties (i) through (iv) noted above.

In a specific embodiment, such antibodies include heavy chain variable region CDR1, CDR2, and CDR3 sequences and light chain variable region CDR1, CDR2, and CDR3 sequences as set forth in SEQ ID NOs:13, 14, 15, 17, 18 and 19 respectively or a set of such CDR sequences with conservative sequence modifications in any one or more of said CDR sequences.

In a further embodiment, the heavy chain variable region CDR1, CDR2, and CDR3 sequences and the light chain variable region CDR1, CDR2, and CDR3 sequences are as set forth in SEQ ID NOs:13, 14, 15, 17, 18 and 19, respectively.

In another aspect, the subject invention provides an isolated monoclonal antibody including a heavy chain variable region comprising a sequence selected from the group consisting of SEQ ID NOs:4, 8 and 12, which: (a) binds to hIL-13Rα1 through domain 3 of the extracellular region of the receptor, and (b) exhibits at least one of the functional properties (i) through (iv) noted above.

In another aspect, the subject invention provides an isolated monoclonal antibody including a light chain variable region comprising an amino acid sequence selected from the group consisting of SEQ ID NO:16, which: (a) binds to hIL-13Rα1 through domain 3 of the extracellular region of the receptor, and (b) exhibits at least one of the functional properties (i) through (iv) noted above.

In another aspect, such isolated monoclonal antibodies include a heavy chain variable region and a light chain variable region comprising SEQ ID NOs:12 and 16, respectively.

Homologous Antibodies.

In yet another embodiment, an antibody of the subject invention includes heavy and/or light chain variable regions with amino acid sequences that are homologous to the amino acid sequences of specific antibodies described herein, and wherein the antibodies retain the desired functional properties of the anti-IL-13Rα1 antibodies of the instant invention.

For example, the present invention provides an isolated monoclonal antibody including a heavy chain variable region sequence that is at least 90% homologous in variable regions to a sequence selected from the group consisting of SEQ ID NOs:4, 8 and 12, which: (a) binds to hIL-13Rα1 through domain 3 of the extracellular region of the receptor, and (b) exhibits at least one of the functional properties (i) through (iv) noted above.

Reference to "at least 90% homologous" includes at least 90, 91, 92, 93, 94, 95, 96, 97, 98, 99 and 100% homologous sequences.

In another embodiment, the present invention provides an isolated monoclonal antibody including a light chain variable region sequence that is at least 90% homologous to SEQ ID NO:16, which: (a) binds to hIL-13Rα1 through domain 3 of the extracellular region of the receptor, and (b) exhibits at least one of the functional properties (i) through (iv) noted above.

In a specific embodiment, such isolated monoclonal antibodies include heavy chain and light chain variable regions that are at least 90% homologous to SEQ ID NOs:12 and 16, respectively.

In other embodiments, the $V_H$ and/or $V_L$ amino acid sequences may be 95%, 96%, 97%, 98% or 99% homologous to the sequences set forth above. An antibody having $V_H$ and/or $V_L$ sequences having high (i.e., 90% or greater) homology to the $V_H$ sequences of SEQ ID NOs:4, 8 and 12 and/or the $V_L$ sequences of SEQ ID NO:16, respectively, can be obtained by mutagenesis (e.g., site-directed or random mutagenesis) of nucleic acid molecules encoding SEQ ID NOs:4, 8 and 12 and/or SEQ ID NO:16, followed by testing of the encoded altered antibody for retained function (i.e., the functions set forth in (i) through (iv) above) using the functional assays described herein.

In yet another embodiment, an antibody of the invention includes heavy and/or light chain variable regions with sets of CDR1, CDR2 and CDR3 sequences that are homologous to the sets of CDR1, CDR2 and CDR3 sequences of the specific antibodies described herein, and wherein the antibodies retain the desired functional properties of the anti-hIL-13Rα1 antibodies of the invention.

For example, the subject invention provides an isolated monoclonal antibody including a heavy chain variable region with a set of CDR1, CDR2 and CDR3 sequences that are at least 90% homologous to a set of CDR1, CDR2 and CDR3 sequence selected from the group consisting of: (a) SEQ ID NOs:5, 6 and 7, respectively; (b) SEQ ID NOs:9, 10 and 11, respectively; or (c) SEQ ID NOs:13, 14 and 15, respectively; wherein the antibody binds to hIL-13Rα1 through domain 3 of the extracellular region of the receptor and exhibits at least one of the functional properties (i) through (iv) noted above.

In another embodiment, the instant invention provides an isolated monoclonal antibody including a light chain variable region with a set of CDR1, CDR2 and CDR3 sequences that are at least 90% homologous to a set of CDR1, CDR2 and CDR3 sequence selected from the group consisting of SEQ ID NOs:17, 18 and 19, respectively; wherein the antibody binds to hIL-13Rα1 through domain 3 of the extracellular region of the receptor and exhibits at least one of the functional properties (i) through (iv) noted above.

In another embodiment, the present invention provides an isolated monoclonal antibody including a heavy chain variable region with a set of CDR1, CDR2 and CDR3 sequences and a light chain variable region with a set of CDR1, CDR2 and CDR3 sequences that are at least 90% homologous to a set of heavy and light chain variable region CDR1, CDR2 and CDR3 sequence selected from the group consisting of SEQ ID NOs:13, 14, 15, 17, 18 and 19, respectively; wherein the antibody binds to hIL-13Rα1 through domain 3 of the extracellular region of the receptor and exhibits at least one of the functional properties (i) through (iv) noted above.

As used herein, the percent homology between two amino acid sequences, or between two sets of CDR sequences, or between two nucleotide sequences, is equivalent to the percent identity between the two sequences, or two sets of CDR sequences. The percent identity between the two sequences, or two sets of CDR sequences, is a function of the number of identical positions shared by the sequences (i.e., % homology=# of identical positions/total # of positions×100), taking into account the number of gaps, and the length of each gap, which need to be introduced for optimal alignment of the two sequences, or two sets of corresponding CDR sequences (i.e., comparing relevant heavy and/or light chain CDR sequences against each other). The comparison of sequences and determination of percent identity between sequences can be accomplished using a mathematical algorithm, as described in the non-limiting examples below.

The percent identity between amino acid sequences and/or nucleotide sequences can be determined using methods generally known to those in the art, for example the algorithm of Meyers and Miller, *Comput. Appl. Biosci.*, 4:11-17, 1988, which has been incorporated into the ALIGN program (version 2.0). In addition, the percent identity between amino acid sequences or nucleotide sequences can be determined using the GAP program in the GCG software package using its default parameters.

Antibodies with Conservative Modifications.

As used herein, the terms "conservative sequence modifications" and "conservative modifications" are used interchangeably and are intended to refer to amino acid modifications that do not significantly reduce or alter the binding characteristics of the antibody containing the amino acid sequence but may improve such properties. Such conservative modifications include amino acid substitutions, additions and deletions, and preferably are conservative amino acid substitutions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein.

Antibodies that Compete with 4B5, 8B11 or 15F4.

In another embodiment, the present invention provides anti-hIL-13Rα1 antibodies that compete for binding to hIL-13Rα1 with antibodies 4B5, 8B11 or 15F4 described herein. Such competing antibodies can be identified based on their ability to cross-compete (e.g., to competitively inhibit the binding of, in a statistically significant manner) with antibodies 4B5, 8B11 or 15F4 in standard IL-13Rα1 binding assays. The ability of a test antibody to inhibit the binding of 4B5, 8B11 or 15F4 to human IL-13Rα1 demonstrates that the test antibody can compete with that antibody for binding to human IL-13Rα1; such an antibody may, according to non-limiting theory, bind to the same or a related (e.g., a structurally similar or spatially proximal) epitope on human IL-13Rα1 as the antibody with which it competes. Antibodies that compete for binding with at least one of 4B5, 8B11 or 15F4 may then be assessed for (a) binding to hIL-13Rα1 through domain 3 of the extracellular region of the receptor, and (b) having at least one of the functional properties (i) through (iv) noted above.

Specific competing antibodies are those wherein a substitution mutation in a peptide comprising domain 3 of hIL-13Rα1 of the residues Val-Phe-Tyr-Val-Gln (SEQ ID NO:44), that correspond to positions 248-252 of SEQ ID NO:1, with the residues Ile-Leu-Glu-Val-Glu (SEQ ID NO:45) leads to a loss of binding between said antibody and the resultant mutant hIL-13Rα1 peptide compared to the binding between said antibody and the hIL-13Rα1 peptide without said substitutions.

Other competing antibodies are those wherein a substitution mutation in a peptide including domain 3 of hIL-13Rα1 of any one of: the phenylalanine residue that corresponds to position 249 of SEQ ID NO:1 with an alanine residue; the tyrosine residue that corresponds to position 250 of SEQ ID NO:1 with an alanine residue; or the glutamine residue that corresponds to position 252 of SEQ ID NO:1 with an alanine residue; leads to a loss of binding between said antibody and the resultant mutant hIL-13Rα1 peptide compared to the binding between said antibody and the hIL-13Rα1 peptide without said substitutions.

Competing antibodies may be prepared by any methods in the art, followed by screening in an appropriate competition assay. Relevant functional activity may be determined using the assays described herein or by other methods readily determined by those skilled in the art.

In a specific embodiment competing antibodies are human antibodies. In another embodiment competing antibodies are humanized, primatized or are chimeric antibodies.

In another embodiment competing antibodies are full-length antibodies.

Specific competing antibodies bind to human IL-13Rα1 with a $K_D$ of $5\times10^{-9}$ M or less, more preferably $2\times10^{-9}$ M or less, and even more preferably $1\times10^{-9}$ M or less.

Engineered and Modified Antibodies.

An antibody of the invention can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region modification is to mutate amino acid residues within the $V_H$ and/or $V_L$ CDR1, CDR2 and/or CDR3 regions to thereby improve one or more properties (e.g., binding affinity) of the antibody of interest. Site-directed mutagenesis or random mutagenesis can be performed to introduce the mutation(s) and the effect on antibody binding, or other functional property of interest, can be evaluated in in vitro or in vivo assays as described herein and provided in the Examples. The mutations may be amino acid substitutions, additions or deletions, but are preferably substitutions. Moreover, typically no more than one, two, three, four or five residues within a CDR region are altered, preferably only one or two residues within the $V_H$ and/or $V_L$ CDR1, CDR2 and/or CDR3 regions are altered.

Antibodies of the invention include those in which modifications have been made to framework residues within $V_H$ and/or $V_L$, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Application No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat et al, 1991 supra.

In one embodiment, the hinge region of $C_{H1}$ is modified such that the number of cysteine residues in the hinge region is altered, e.g., increased or decreased, to, for example, facilitate assembly of the light and heavy chains or to increase or decrease the stability of the antibody. This approach is described further in U.S. Pat. No. 5,677,425 by Bodmer et al.

In another embodiment, the Fc hinge region of an antibody is mutated to decrease the biological half-life of the antibody. This approach is described in further detail in U.S. Pat. No. 6,165,745 by Ward et al.

In another embodiment, the antibody is modified to increase its biological half-life. Various approaches are possible. For example, one or more of the following mutations can be introduced: Thr252Leu, Thr254Ser, Thr256Phe, as described in U.S. Pat. No. 6,277,375 by Ward. Alternatively, to increase the biological half-life, the antibody can be altered within the $C_{H1}$ or CL region to contain a salvage receptor binding epitope taken from two loops of a $C_{H2}$ domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, see U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are modified to thereby alter the ability of the antibody to fix complement. This approach is described further in WO 94/29351 by Bodmer et al.

In yet another example, the Fc region is modified to increase the ability of the antibody to mediate antibody-dependent cellular cytotoxicity (ADCC) and/or to increase the affinity of the antibody for an Fcγ receptor by modifying one or more amino acids; see for example WO 00/42072 by Presta. Moreover, the binding sites on human IgG1 for FcγR1, FcγRII, FcγRIII and FcRn have been mapped and variants with improved binding have been described (see Shields et al, J. Biol. Chem. 276:6591-6604, 2001).

Specific embodiments of the present invention provide an antibody molecule as defined in accordance with the present invention which includes, as part of its immunoglobulin structure, SEQ ID NO:42. FIG. 6 illustrates a comparison of the sequence of IgG2 m4 (as described in U.S. Patent Publication No. US20070148167(A1)), which includes the amino acid sequence set forth in SEQ ID NO:42, with the amino acid sequence of IgG1, IgG2, and IgG4.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such an approach is described in further detail in U.S. Pat. Nos. 5,714,350 and 6,350,861 by Co et al.

Additionally or alternatively, an antibody can be made that has an altered type of glycosylation, such as a non-fucosylated or a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation.

Another modification of the antibodies herein that is contemplated by the invention is pegylation. An antibody can be pegylated to, for example, increase the biological (e.g., serum) half-life of the antibody, or an antigen binding portion thereof. To pegylate an antibody, the antibody typically is reacted with polyethylene glycol (PEG), such as a reactive ester or aldehyde derivative of PEG, under conditions in which one or more PEG groups become attached to the antibody or antibody fragment. Methods for pegylating proteins are known in the art and can be applied to the antibodies of the invention. See, for example, EP 0 154 316 by Nishimura et al and EP 0 401 384 by Ishikawa et al.

Methods of Modifying Antibodies.

As discussed above, the anti-IL-13Rα1 antibodies having $V_H$ and $V_L$ sequences disclosed herein can be used to create new anti-IL-13Rα1 antibodies by modifying the $V_H$ and/or $V_L$ sequences, or the constant region(s) attached thereto. Thus, in another aspect of the invention, the structural features of an anti-hIL-13Rα1 antibody of the invention, e.g., 4B5, 8B11 or 15F4, are used to create structurally related anti-hIL-13Rα1 antibodies that retain functional properties of the antibodies of the invention, such as binding to human IL-13Rα1 through domain 3 of the extracellular region of the receptor, and also inhibiting one or more functional properties of hIL-13Rα1. For example, one or more CDR regions of 4B5, 8B11 or 15F4, or mutations thereof, can be combined recombinantly with known framework regions and/or other CDRs to create additional, recombinantly-engineered, anti-IL-13Rα1 antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein. Standard molecular biology techniques can be used to prepare and express the altered antibody sequence.

The functional properties of the altered antibodies can be assessed using standard assays available in the art and/or described herein, such as those set forth in the Examples. Anti-IL-13Rα1 antibodies that retain the desired characteristics as set out herein are selected.

In certain embodiments of the methods of engineering antibodies of the invention, mutations can be introduced randomly or selectively along all or part of an anti-IL-13Rα1 antibody coding sequence and the resulting modified anti-IL-13Rα1 antibodies can be screened for binding activity and/or other functional properties as described herein. Mutational methods have been described in the art. For example, WO 02/092780 by Short describes methods for creating and screening antibody mutations using saturation mutagenesis, synthetic ligation assembly, or a combination thereof. Alternatively, WO 03/074679 by Lazar et al describes methods of using computational screening methods to optimize physiochemical properties of antibodies.

Generation of Monoclonal Antibodies of the Invention.

Monoclonal antibodies of the present invention can be produced by a variety of techniques, including conventional monoclonal antibody methodology e.g., the standard somatic cell hybridization technique of Kohler & Milstein, *Nature* 256:495, 1975. Although somatic cell hybridization procedures are typically preferred, in principle, other techniques for producing monoclonal antibody can be employed e.g., viral or oncogenic transformation of B lymphocytes.

The animal system typically preferred for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric, humanized or primatized antibodies of the present invention can be prepared based on the sequence of a murine monoclonal antibody prepared using standard molecular biology and generally in accordance with the description herein. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al). To create a humanized antibody, the murine CDR regions can be inserted into a human framework using methods known in the art (see e.g., U.S. Pat. No. 5,225,539 to Winter, and U.S. Pat. Nos. 5,530, 101; 5,585,089; 5,693,762 and 6,180,370 to Queen et al). Similarly, to create a primatized antibody the murine CDR regions can be inserted into a primate framework using methods known in the art (see, e.g., WO 93/02108 and WO 99/55369).

Alternatively, a humanized antibody may be created by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al, *Mol. Immunol.* 28:489-498, 1991 and Pedersen et al, *J. Mol. Biol.* 235:959-973, 1994). Therefore, it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system (see also Mark et al, *Handbook of Experimental Pharmacology* vol. 113: The pharmacology of monoclonal Antibodies, Springer-Verlag, pp 105-134, 1994, and U.S. Pat. No. 6,797, 492). This procedure of humanization is referred to as "veneering" because only the surface of the antibody is altered, the supporting residues remain undisturbed.

Further, WO 2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g., germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO 2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

In a specific embodiment, the antibodies of the present invention are human monoclonal antibodies. Such human monoclonal antibodies directed against IL-13Rα1 can be generated using transgenic or transchromosomic mice carrying parts of the human immune system rather than the mouse system. These transgenic and transchromosomic mice include mice referred to herein as HUMAB® mice and KM mice, respectively, and are collectively referred to herein as "human Ig mice."

The HUMAB® mouse (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see, e.g., Lonberg, et al, *Nature* 368(6474):856-859, 1994). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg et al, 1994, supra; reviewed in Lonberg, *Handbook of Experimental Pharmacology* 113:49-101, 1994; Lonberg and Huszar, *Intern. Rev. Immunol.* 13:65-93, 1995, and Harding and Lonberg, *Ann. N.Y. Acad. Sci.* 764: 536-546, 1995). The preparation and use of HUMAB® mice, and the genomic modifications carried by such mice, is further described in Taylor et al, *Nucleic Acids Research* 20:6287-6295, 1992; Chen et al, *International Immunology* 5:647-656, 1993; Tuaillon et al, *Proc. Natl. Acad. Sci. USA* 90:3720-3724, 1993; Choi et al, *Nature Genetics* 4:117-123, 1993; Chen et al, *EMBO J.* 12:821-830, 1993; Tuaillon et al, *J. Immunol.* 152:2912-2920, 1994; Taylor et al, *International Immunology* 6:579-591, 1994; and Fishwild et al, *Nature Biotechnology* 14:845-851, 1996. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al; WO 92/03918, WO 93/12227, WO 94/25585, WO 97/13852, WO 98/24884 and WO 99/45962, all to Lonberg and Kay; and WO 01/14424 to Korman et al.

In another embodiment, human antibodies of the subject invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in WO 02/43478 to Ishida et al.

Still further, alternative transgenic animal systems expressing human immunoglobulin genes are available in the art and can be used to raise anti-IL-13Rα1 antibodies of the invention. For example, an alternative transgenic system referred to as the XENOMOUSE® (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-IL-13Rα1 antibodies of the invention. For example, mice carrying both a human heavy chain transchromosome and a human light chain tranchromosome, referred to as "TC mice" can be used; such mice are described in Tomizuka et al, *Proc. Natl. Acad. Sci. USA* 97:722-727, 2000. Furthermore, cows carrying human heavy and light chain transchromosomes have been described in the art (Kuroiwa et al, *Nature Biotechnology* 20:889-894, 2002) and can be used to raise anti-IL-13Rα1 antibodies of the invention.

Human monoclonal antibodies of the invention can also be prepared using phage display methods for screening libraries of human immunoglobulin genes. Such phage display methods for isolating human antibodies are established in the art. See, for example, U.S. Pat. Nos. 5,223,409; 5,403,484; and 5,571,698 to Ladner et al; U.S. Pat. Nos. 5,427,908 and 5,580,717 to Dower et al; U.S. Pat. Nos. 5,969,108 and 6,172,197 to McCafferty et al; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Characterization of Antibody Binding to Antigen.

Antibodies of the invention can be tested for binding to IL-13Rα1, and for binding through domain 3 of the extracellular region of the receptor, by, for example, standard ELISA. Similarly, an ELISA assay can also be used to screen for hybridomas that show positive reactivity with IL-13Rα1.

To determine if the selected anti-hIL-13Rα1 monoclonal antibodies compete with antibodies 4B5, 8B11 or 15F4, each antibody can be biotinylated using standard procedures. Competition studies using unlabeled monoclonal antibodies and biotinylated monoclonal antibodies can be performed using IL-13Rα1 coated-ELISA plates as described in the Examples. Biotinylated mAb binding can be detected with a strep-avidin-alkaline phosphatase probe. BIACORE™-based experiments may also be used to determine competition between antibodies for binding to hIL-13Rα1.

Similarly, ELISA-based assays can be used to determine whether a substitution mutation in a peptide including domain 3 of hIL-13Rα1 of the residues Val-Phe-Tyr-Val-Gln (SEQ ID NO:44) that correspond to positions 248-252 of SEQ ID NO:1 with the residues Ile-Leu-Glu-Val-Glu (SEQ ID NO:45) leads to a loss of binding between an anti-IL-13Rα1 antibody and the resultant mutant hIL-13Rα1 peptide compared to the binding between said antibody and the hIL-13Rα1 peptide without said substitutions. The same approach may be used to determine whether substitution of other segments of SEQ ID NO:1 affect anti-IL-13 Rα1 antibody binding.

ELISA-based assays may also be used to determine whether a substitution mutation in a peptide including domain 3 of hIL-13Rα1 of any one of: the phenylalanine residue that corresponds to position 249 of SEQ ID NO:1 with an alanine residue; the tyrosine residue that corresponds to position 250 of SEQ ID NO:1 with an alanine residue; or the glutamine residue that corresponds to position 252 of SEQ ID NO:1 with an alanine residue; leads to a loss of binding between said antibody and the resultant mutant hIL-13Rα1 peptide compared to the binding between said antibody and the hIL-13Rα1 peptide without said substitutions.

hIL-13Rα1 peptides suitable for use in such assays will be readily determined by those skilled in the art and include fragments of full-length hIL-13Rα1, for example the extracellular region of the receptor or domain 3 of the extracellular region of the receptor which may be fused to other peptides, for example for display on phage.

To determine the isotype of purified antibodies, isotype ELISAs can be performed using reagents specific for antibodies of a particular isotype.

Immunoconjugates.

In another aspect, the present invention features an anti-IL-13Rα1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates and methods of forming them are well-known in the art.

For further discussion of types of cytotoxins, linkers and methods for conjugating therapeutic agents to antibodies, see also Saito et al, *Adv. Drug Deliv. Rev.* 55:199-215, 2003; Trail et al, *Cancer Immunol. Immunother.* 52:328-337, 2003; Payne, *Cancer Cell* 3:207-212, 2003; Allen, *Nat. Rev. Cancer* 2:750-763, 2002; Pastan and Kreitman, *Curr. Opin. Investig. Drugs* 3:1089-1091, 2002; Senter and Springer, *Adv. Drug Deliv. Rev.* 53:247-264, 2001. Bispecific Molecules.

In another aspect, the present invention features bispecific molecules containing an anti-IL-13Rα1 antibody of the invention. An antibody of the invention can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein.

Nucleic Acid Molecules Encoding Antibodies of the Invention.

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well-known in the art. See, Ausubel et al, *Current Protocols in Molecular Biology*, Greene Publishing and Wiley Interscience, New York, 1987. A nucleic acid of the invention can be, for example, DNA or RNA and may or may not contain intronic sequences. In a specific embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further herein), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Specific nucleic acids molecules of the invention are those encoding the $V_H$ and/or $V_L$ sequences of the 4B5, 8B11 or 15F4 monoclonal antibodies. DNA sequences encoding the $V_H$ sequences of 4B5, 8B11 or 15F4 are shown in SEQ ID NOs:21, and 29, respectively. A DNA sequence encoding the $V_L$ sequence of 15F4 is shown in SEQ ID NO:33.

Other nucleic acids molecules of the invention are those encoding the CDRs of the $V_H$ and $V_L$ sequences of the 4B5, 8B11 or 15F4 monoclonal antibodies.

Also included in the present invention are nucleic acids with nucleotide sequences which are at least about 90% identical and more preferably at least about 95% identical to the nucleotide sequences described herein, and which nucleotide sequences encode antibodies of the present invention. Sequence comparison methods to determine identity are known to those skilled in the art and include those discussed herein.

Reference to "at lest about 90% identical" includes at least about 90, 91, 92, 93, 94, 95, 96, 97, 98, 99 or 100% identical.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. The heavy chain constant region can be an IgG1, IgG2, IgG3, IgG4, IgA, IgE, IgM or IgD constant region, and in specific embodiments is an IgG1 or IgG4 constant region or derivative thereof. For a Fab fragment heavy chain gene, the $V_H$-encoding DNA can be operatively linked to another DNA molecule encoding only the heavy chain $C_{H1}$ constant region.

The invention further provides nucleic acids that hybridize to the complement(s) of disclosed nucleic acids (e.g., nucleic acids with a nucleotide sequence as depicted in FIG. 2, 3, 4 or 5) under particular hybridization conditions and that encode antibody molecules which bind hIL-13Rα1 through domain 3 of the extracellular region of the receptor chain and which inhibit IL-13 signaling (i.e., antibodies of the present invention). Methods for hybridizing nucleic acids are well-known in the art, see, e.g., Ausubel, *Current Protocols in Molecular Biology*, John Wiley & Sons, N.Y., 6.3.1-6.3.6, 1989. As defined herein, a moderately stringent hybridization condition uses a prewashing solution containing 5× sodium chloride/sodium citrate (SSC), 0.5% w/v SDS, 1.0 mM EDTA (pH 8.0), hybridization buffer of about 50% v/v formamide, 6×SSC, and a hybridization temperature of 55° C. (or other similar hybridization solutions, such as one containing about 50% v/v formamide, with a hybridization temperature of 42° C.), and washing conditions of 60° C., in 0.5×SSC, 0.1% w/v SDS. A stringent hybridization condition is, for example, 6×SSC at 45° C., followed by one or more washes in 0.1× SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by Sambrook et al, *Molecular Cloning: A Laboratory Manual*, Cold Spring Harbor Laboratory Press, Cold Spring Harbor, N.Y., chapters 9 and 11, 1989 and Ausubel et al (eds), *Current Protocols in Molecular Biology*, John Wiley & Sons, Inc., sections 2.10 and 6.3-6.4, 1995), and can be readily determined by those having ordinary skill in the art based on, for example, the length and/or base composition of the DNA.

Accordingly, in another aspect, the present invention provides an anti-hIL-13Rα1 antibody including a light chain variable domain with an amino acid sequence that is encoded by a nucleotide sequence that hybridizes under moderately stringent conditions to the complement of a nucleotide sequence of SEQ ID NO:33, and/or a heavy chain variable domain with an amino acid sequence that is encoded by a nucleotide sequence that hybridizes under moderately stringent conditions to the complement of a nucleotide sequence selected from the group consisting of SEQ ID NOs:21, 25 and 29. In one embodiment, said light chain variable domain includes an amino acid sequence that is encoded by a nucleotide sequence that hybridizes under stringent conditions to the complement of a nucleotide sequence of SEQ ID NO:33, and/or said heavy chain variable domain with an amino acid sequence that is encoded by a nucleotide sequence that hybridizes under stringent conditions to the complement of a nucleotide sequence selected from the group consisting of SEQ ID NOs:21, 25 and 29.

Specific embodiments of the present invention encompass nucleic acid encoding antibody molecules that possess manipulations in the Fc region which result in reduced binding to FcγR receptors or C1q on the part of the antibody. One specific embodiment of the present invention is an isolated nucleic acid having the sequence set forth in SEQ ID NO:43. Production of Monoclonal Antibodies of the Invention.

In another aspect, the present invention provides vectors including nucleic acid encoding an antibody of the present invention. Vectors in accordance with the present invention include, but are not limited to, plasmids and other constructs (e.g., phage or phagemid) suitable for the expression of the desired peptide at the appropriate level for the intended purpose.

In another aspect, the present invention provides host cell(s) harboring nucleic acids encoding an antibody of the present invention. Typically, the host cell will harbor an expression vector as described herein.

Antibodies of the invention can be produced in a host cell using, for example, a combination of recombinant DNA techniques and gene transfection methods as is well-known in the art (e.g., Morrison *Science* 229:1202, 1985).

For example, to express the antibodies, or antibody fragments thereof, DNA encoding partial or full-length light and heavy chains, can be obtained by standard molecular biology techniques (e.g., PCR amplification or cDNA cloning using a hybridoma that expresses the antibody of interest) and the DNA can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (e.g., ligation of complementary restriction sites on the antibody gene fragment and vector, or blunt-end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, *Gene Expression Technology. Methods in Enzymology* 185, Academic Press, San Diego, Calif., 1990. It will be appreciated by those skilled in the art that the design of the expression vector, including the selection of regulatory sequences, may depend on such factors as the choice of the host cell to be transformed, the level of expression of protein desired, etc. Specific regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or beta-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al). For example, typically the selectable marker gene confers resistance to drugs, such as G418, hygromycin or methotrexate, on a host cell into which the vector has been introduced. Specific selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells, and mammalian host cells, is typically preferred because such eukaryotic cells, and in particular mammalian cells, are more likely than prokaryotic cells to assemble and secrete a properly folded and immunologically active antibody.

Specific mammalian host cells for expressing the recombinant antibodies of the invention include Chinese Hamster Ovary (CHO) cells (including DHFR-CHO cells, described in Urlaub and Chasin, *Proc. Natl. Acad. Sci. USA* 77:4216-4220, 1980, used with a DHFR selectable marker, e.g., as described in Kaufman and Sharp, *Mol. Biol.* 159:601-621, 1982), NSO myeloma cells, COS cells and SP2 cells. In particular, for use with NSO myeloma cells, another specific expression system is the GS gene expression system disclosed in WO 87/04462, WO 89/01036 and EP 338,841. When recombinant expression vectors encoding antibody genes are introduced into host cells, the antibodies are produced by culturing the host cells for a period of time sufficient to allow for expression of the antibody in the host cells or secretion of the antibody into the culture medium in which the host cells are grown. Antibodies can be recovered from the cells and/or culture medium using standard protein purification methods.

Accordingly, in another aspect the invention provides a method of producing an antibody of the invention by culturing host cells harboring nucleic acid encoding an antibody of the invention. Said method may further involves purifying the antibody.

Identification of Antibodies which Bind Via Domain 3.

In another aspect, the invention provides methods of identifying antibodies capable of binding to hIL-13Rα1 through domain 3 of the extracellular region of the receptor.

In one aspect, the method involves testing antibodies for binding to peptides including either domain 1, domain 2 or domain 3 of the extracellular region of hIL-13Rα1. Antibodies which bind the peptide include domain 3 but that show little or no binding to domains 1 or 2 of the extracellular region of the receptor may be selected.

In another aspect the method involves testing antibodies which bind the extracellular region of the receptor for binding to domains 1 and 2 of the receptor. Antibodies that do not bind to domains 1 and 2 may be selected as potentially binding to domain 3.

Binding, or lack thereof, to peptides including the various domains can be readily determined by standard methods; see, e.g., Example 3.

Peptides including one or two domains of the extracellular region of hIL-13Rα1 and lacking the other domain or domains of the extracellular region of hIL-13Rα1 (i.e., truncated forms of the extracellular region of hIL-13Rα1) are useful in such methods. For example, a peptide including domain 3, but lacking domains 1 and 2, may be useful in the methods, as may be a peptide including both domains 1 and 2, but lacking domain 3.

The truncated forms of the extracellular region of hIL-13Rα1 may be fused to other sequences to assist the performance of the method, for example to assist purification, immobilization, detection or display. Display of the peptides including the relevant domains on phage is also a useful approach for use in these methods; see, e.g., Example 3.

The extracellular region of hIL-13Rα1 corresponds to amino acids 1 to 317 of SEQ ID NO:1. In accordance with the present invention, domain 1 of extracellular region of hIL-13Rα1 corresponds to amino acids 1 to 100 of SEQ ID NO:1, domain 2 corresponds to amino acids 101 to 200 of SEQ ID NO:1, and domain 3 corresponds to amino acids 201 to 317 of SEQ ID NO:1 (SEQ ID NO:37). It will be appreciated by those skilled in the art that some discretion exists with respect to the precise amino acid residues included at the ends of the domains.

Accordingly, the invention provides a peptide comprising including: (a) domain 1 of the extracellular region of hIL-13Rα1; (b) domain 2 of the extracellular region of hIL-13Rα1; (c) domain 3 of the extracellular region of hIL-13Rα1; or (d) domains 2 and 3 of the extracellular region of hIL-13Rα1; wherein in each case said peptide does not contain other domains of the extracellular region of hIL-13Rα1.

In a particular embodiment, the invention provides a peptide including: (a) amino acids 1 to 100 of SEQ ID NO:1; (b) amino acids 101 to 200 of SEQ ID NO:1; (c) amino acids 201 to 317 of SEQ ID NO:1; or (d) amino acids 1 to 200 of SEQ ID NO:1; wherein in each case the peptide does not contain other domains of the extracellular region of hIL-13Rα1.

In another aspect the invention provides nucleic acids encoding such truncated forms of the extracellular region of hIL-13Rα1. Accordingly, in another aspect, the invention provides nucleic acids encoding a peptide including: (a) domain 1 of the extracellular region of hIL-13Rα1; (b) domain 2 of the extracellular region of hIL-13Rα1; (c) domain 3 of the extracellular region of hIL-13Rα1; or (d) domains 2 and 3 of the extracellular region of hIL-13Rα1; wherein in each case said peptide does not contain other domains of the extracellular region of hIL-13Rα1.

In a particular embodiment, the invention provides nucleic acids encoding a peptide including: (a) amino acids 1 to 100 of SEQ ID NO:1; (b) amino acids 101 to 200 of SEQ ID NO:1; (c) amino acids 201 to 317 of SEQ ID NO:1; or (d) amino acids 1 to 200 of SEQ ID NO:1; wherein in each case the peptide does not contain other domains of the extracellular region of hIL-13Rα1.

In another aspect, the present invention provides vectors including said nucleic acid encoding truncated forms of the extracellular region of hIL-13Rα1. Vectors in accordance with the present invention include, but are not limited to, plasmids and other constructs (e.g., phage or phagemid) suitable for the expression of the desired peptide at the appropriate level for the intended purpose; see, e.g., Sambrook & Russell, Molecular Cloning: A Laboratory Manual: 3rd Edition, Cold Spring Harbor Laboratory Press. For most cloning purposes, DNA vectors may be used. Typical vectors include plasmids, modified viruses, bacteriophage, cosmids, yeast artificial chromosomes, and other forms of episomal or integrated DNA. It is well within the purview of the skilled artisan to determine an appropriate vector for a particular gene transfer, generation of a recombinant peptide, or other use. In specific embodiments, in addition to a recombinant gene, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, other sequences as appropriate and the potential for high copy number. Examples of expression vectors for peptide production are well known in the art. If desired, nucleic acid encoding a peptide of interest may be integrated into the host chromosome using techniques well-known in the art. Nucleic acid may also be expressed on plasmids maintained episomally or incorporated into an artificial chromosome. Any technique available to the skilled artisan may be employed to introduce the nucleic acid into the host cell. Methods of subcloning nucleic acid molecules of interest into expression vectors, transforming or transfecting host cells with such vectors, and methods of making substantially pure protein comprising the steps of introducing the respective expression vector into a host cell, and cultivating the host cell under appropriate conditions are well-known. The peptide so produced may be harvested from the host cells in conventional ways. Techniques suitable for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage).

In another aspect, the present invention provides isolated cell(s) harboring nucleic acids encoding the disclosed receptor truncates as described. A variety of different cell lines can be used for recombinant production of such peptides, including but not limited to those from prokaryotic organisms (e.g., *E. coli, Bacillus*, and *Streptomyces*) and from eukaryotic (e.g., yeast, insect, and mammalian). Plant cells, including transgenic plants, and animal cells, including transgenic animals (other than humans), comprising the nucleic acid disclosed herein are also contemplated as part of the present invention.

Compositions and Pharmaceutical Compositions.

In another aspect, the present invention provides a composition, e.g., a pharmaceutical composition, containing one or a combination of monoclonal antibodies of the present invention, formulated together with at least one additional component. Such compositions may include one or a combination of (e.g., two or more different) antibodies, or immunoconjugates or bispecific molecules of the invention. For example, a pharmaceutical composition of the invention can include a combination of antibodies (or immunoconjugates or bispecifics) that bind to different epitopes on the target antigen or that have complementary activities.

Thus, pharmaceutical compositions according to the present invention, and for use in accordance with the present invention, may include, in addition to the active ingredient, pharmaceutically acceptable carriers, diluents and/or excipients. The precise nature of the carrier or other material will depend on the route of administration, which may be oral, or by injection, e.g., intravenous.

Pharmaceutically acceptable carriers, diluents and/or excipients include any and all solvents, dispersion media, coatings, antibacterial and antifungal agents, agents used for adjusting tonicity, buffers, chelating agents, and absorption delaying agents and the like. The use of such media and agents for pharmaceutical active substances is well-known in the art. Except insofar as any conventional media or agent is incompatible with the active ingredient, use thereof in the therapeutic compositions is contemplated. Supplementary active ingredients can also be incorporated into the compositions.

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin. The compositions may also include buffers and chelating agents.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

The amount of active compound in such therapeutically useful compositions is such that a suitable dosage will be obtained.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

For administration of the antibody, the dosage ranges from about 0.01 to 100 mg/kg, and more usually 0.05 to 25 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime may entail administration once per week, once every two weeks, once every three weeks, once every four weeks, or once a month.

In some methods, two or more monoclonal antibodies with different binding specificities are administered simultaneously, in which case the dosage of each antibody administered falls within the ranges indicated.

Alternatively, antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition of the present invention can be administered via one or more routes of administration using one or more of a variety of methods known in the art. As will be appreciated by the skilled artisan, the route and/or mode of administration will vary depending upon the desired results. Specific routes of administration for antibodies of the present invention include intravenous, intramuscular, intradermal, intraperitoneal, subcutaneous or other parenteral routes of administration, for example by infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Marcel Dekker, Inc., New York, 1978.

Therapeutic compositions can be administered with medical devices known in the art. For example, in a specific embodiment, a therapeutic composition of the invention can be administered with a needleless hypodermic injection device, such as the devices disclosed in U.S. Pat. No. 5,399, 163; 5,383,851; 5,312,335; 5,064,413; 4,941,880; 4,790,824; or 4,596,556.

Uses and Methods of the Invention.

Antibodies of the present invention may be used in methods of inhibiting IL-13Rα1-mediated signaling by contacting a cell expressing IL-13Rα1 with an antibody of the present invention under conditions that allow said antibody to bind to IL-13Rα1. Specific embodiments of the present invention include such methods wherein the cell is a human cell.

Antibodies of the present invention may be used in methods of diagnosis or treatment in human or animal subjects.

For example, these molecules can be administered to a subject to treat or prevent a variety of IL-13 related disorders and diseases. The term "subject", as used herein, is intended to include humans and, where the antibody has appropriate cross-reactivity, non-human animals. Non-human animals may include non-human primates. The methods are particularly suitable for treating human patients having an IL-13-related disorder or disease. When antibodies to IL-13Rα1 are administered together with another agent, the two can be administered in either order or simultaneously.

Accordingly, in one aspect, the invention provides a method of treating an IL-13-related disease or disorder in a subject in need of treatment by administering to the subject an effective amount of an antibody of the present invention, or a composition including such an antibody. A disease or disorder is referred to as being "IL-13-related" if the signs or symptoms of such a disease or disorder are mediated by the expression, activity or mutation of IL-13, including instances when the expression or activity of IL-13 is elevated or reduced compared to a normal or healthy subject. Examples of diseases or disorders which are IL-13-related are disclosed herein.

The terms "treating" and "treatment", as used herein, refer to therapeutic treatment and may include prophylactic or preventative measures. For example, treatment may result in a reduction in severity and/or the frequency of symptoms of an IL-13-associated disease or disorder, the elimination of symptoms and/or underlying cause of an IL-13-associated disease or disorder, or the prevention of the occurrence of symptoms and/or their underlying cause. Hence, the treatment may not result in a "cure", but rather an amelioration of symptoms. Treatment includes the inhibition of IL-13Rα1-mediated signaling in a subject exhibiting an IL-13-related disease or disorder by administering to the subject an effective amount of an antibody of the present invention, or a composition including such an antibody.

The term "effective amount", as used herein, means a sufficient amount of an agent which provides the desired therapeutic or physiological effect or outcome, or inhibiting the activity of IL-13Rα1. Undesirable effects, e.g., side effects, may sometimes manifest along with the desired therapeutic effect; hence, a practitioner balances the potential benefits against the potential risks in determining what is an appropriate "effective amount". The exact amount of agent required may vary from subject to subject, depending on factors such as the species, age and general condition of the subject, mode of administration and the like. Thus, it may not be possible to specify an exact "effective amount". However, an appropriate effective amount in any individual case may be readily determined by one of ordinary skill in the art based on such factors as the subject's size, the severity of the subject's symptoms, and the particular composition or route of administration selected.

Also contemplated are methods of using an antibody of the present invention in the manufacture of a medicament for treatment of IL-13 related disorders and diseases.

In another aspect, the invention provides methods for detecting the presence of IL-13Rα1 (e.g., human IL-13Rα1) in a sample, or measuring the amount of IL-13Rα1, by contacting the sample, and a control sample, with an antibody of the invention under conditions that allow for formation of a complex between the antibody and IL-13Rα1. The formation of a complex is then detected, wherein a difference in complex formation between the sample compared to the control sample is indicative of the presence of IL-13Rα1 in the sample.

Also within the scope of the invention is a kit including a composition (e.g., antibody, immunoconjugate and bispecific molecule) of the invention and instructions for use. The kit can further contain at least one additional reagent, or one or more additional antibodies of the invention (e.g., an antibody having a complementary activity which binds to an epitope on the target antigen distinct from the first antibody). Kits typically include a label indicating the intended use of the contents of the kit. The term "label" includes any writing, or recorded material supplied on or with the kit, or which otherwise accompanies the kit.

Examples of IL-13-related disorders and diseases in which the antibodies of the invention may be used include, but are not limited to, asthma, COPD, atopic dermatitis, allergic rhinitis, esophagal eosinophilia, Hodgkin's lymphoma, inflammatory bowel disease, psoriasis, psoriatic arthritis or fibrosis. In a specific embodiment, the IL-13-related disorder or disease is asthma. Further information concerning IL-13-related disorders and diseases is provided herein.

Asthma is a chronic lung disease, caused by inflammation of the lower airways and is characterized by recurrent breathing problems. Airways of patients are sensitive and swollen or inflamed to some degree all the time, even when there are no symptoms. Inflammation results in narrowing of the airways and reduces the flow of air in and out of the lungs, making breathing difficult and leading to wheezing, chest tightness and coughing. Asthma is triggered by super-sensitivity towards allergens (e.g., dust mites, pollens, molds), irritants (e.g., smoke, fumes, strong odors), respiratory infections, exercise and dry weather. The triggers irritate the airways and the lining of the airways swell to become even more inflamed, mucus then clogs up the airways and the muscles around the airways tighten up until breathing becomes difficult and stressful and asthma symptoms appear.

There is strong evidence from animal models and patients that asthmatic inflammation and other pathologies are driven by dysregulated Th2 responses to aeroallergens and other stimuli (Busse et al, *Am. J. Resp. Crit. Care Med.* 1995 152 (1):388-393). In particular, IL-13 is believed to be the major effecter cytokine driving a variety of cellular responses in the lung, including airway hyperreactivity, eosinophilia, goblet cell metaplasia and mucus hyper-secretion.

The gene encoding IL-13 is located on chromosome 5q31. This region also contains genes encoding IL-3, IL-4, IL-5, IL-9 and GM-CSF, and has been linked with asthma. Genetic variants of IL-13 that are associated with asthma and atopy have been found both in the promoter and coding regions (Vercelli, *Curr. Opin. Allergy Clin. Immunol.* 2(5):389-393, 2002). Functional study data are available for the coding variant, Gln130 IL-13 (referred to herein as Q130 IL-13). The +2044 G to A single nucleotide polymorphism (SNP) found in the fourth exon, results in a substitution of an arginine with a glutamine at position 130 (Q130 IL-13). This variant has been found to be associated with asthma, increased IgE levels and atopic dermatitis in Japanese and European populations. Q130 IL-13 is believed to have enhanced stability compared with wild-type IL-13. It also has slightly lower affinity for the IL-13Rα2 decoy receptor and consistent with these observations, higher median serum IL-13 levels are found in patients homozygous for the Q130 IL-13 variant compared with non-homozygous patients. These results indicate that Q130 IL-13 could influence the local and systemic concentrations of IL-13 (Kazuhiko et al, *J. Allergy Clin. Immunol.* 109(6):980-987, 2002).

Elevated IL-13 levels have been measured in both atopic and non-atopic asthmatics. In one study, average serum IL-13 levels of 50 pg/ml were measured in asthmatic patients compared to 8 pg/ml in normal control patients (Lee et al, *J. Asthma* 38(8):665-671, 2001). Increased IL-13 levels have also been measured in plasma, bronchio-alveola lavage fluid, lung biopsy samples and sputum (Berry et al, *J Allergy Clin. Immunol* 114(5):1106-1109, 2004; Kroegel et al, *Eur Respir. J.* 9(5):899-904, 1996; Huang et al, *J. Immunol.* 155 (5):2688-2694, 1995; Humbert et al, *J. Allergy Clin. Immunol.* 99(5): 657-665, 1997).

A number of studies have defined a critical effecter role for IL-13 in driving pathology in both acute and chronic mouse models of allergic asthma. The high affinity IL-13 receptor (IL-13Rα2) or anti-IL-13 polyclonal antibodies have been used to neutralize mouse IL-13 bioactivity in these models. Blockade of IL-13 at the time of allergen challenge completely inhibited OVA-induced airway hyper-responsiveness, eosinophilia and goblet cell metaplasia. In contrast, administration of antibody to IL-4 after sensitization and during the allergen challenge phase only partially reduced the asthma phenotype. Thus, although exogenous IL-4 and IL-13 are both capable of inducing an asthma-like phenotype, the effecter activity for IL-13 appears to be superior to that for IL-4. These data suggest a primary role for IL-4 in immune induction (particularly for Th2 cell development and recruitment to airways, and IgE production), whereas IL-13 is believed to be principally engaged in various effecter outcomes, including airway hyper-responsiveness, mucus over-production and cellular inflammation (Wills-Karp et al, *Science* 282:2258-2261, 1998; Grunig et al, *Science* 282:2261-2263, 1998; Taube et al, *J. Immunol.* 169:6482-6489, 2002; Blease et al, *J. Immunol* 166(8):5219-5224, 2001).

In complementary experiments, lung IL-13 levels have been raised by over-expression in a transgenic mouse or by instillation of IL-13 protein into the trachea of wild-type mice. In both settings, asthma-like characteristics were induced; non-specific airway hyper-responsiveness to cholinergic stimulation, pulmonary eosinophilia, epithelial cell hyperplasia, mucus cell metaplasis, sub-epithelial fibrosis, airways obstruction and Charcot-Leyden-like crystals. In addition, IL-13 was found to be a potent stimulator of matrix metalloproteinases and cathepsin proteases in the lung, resulting in emphysematous changes and mucus metaplasia. Therefore IL-13 may be an important effecter molecule both in asthma and COPD disease phenotypes (Zhu et al, *J. Clin. Invest.* 103(6):779-788, 1999; Zheng et al, *J. Clin. Invest.* 106(9):1081-1093, 2000).

These data indicate that IL-13 activity is both necessary and sufficient to produce several of the major clinical and pathological features of allergic asthma in well-validated animal models.

COPD is a generic term covering several clinical syndromes including emphysema and chronic bronchitis. Symptoms are similar to asthma and COPD can be treated with the same drugs. COPD is characterized by a chronic, progressive and largely irreversible airflow obstruction. The contribution of the individual to the course of the disease is unknown, but smoking cigarettes is thought to cause 90% of the cases. Symptoms include coughing, chronic bronchitis, breathlessness and respiratory infections. Ultimately the disease will lead to severe disability and death. Chronic bronchitis is diagnosed in patients with a history of cough or sputum production on most days for at least 3 months over 2 years without any other explanation. Emphysema of the lung is characterized by an abnormal permanent enlargement of the air spaces and destruction of alveolar walls.

IL-13 has been suggested to play a role in the development of COPD. Human smokers who develop COPD have many inflammatory cell types (neutrophils, macrophages, eosinophils) in the lung parenchyma. IL-13 is a proinflammatory Th2 cytokine, therefore to model the progression of emphysema, Zheng et al, 1999, supra targeted IL-13 over-expression to the airway epithelium in IL-13 transgenic mice. These animals developed airway and lung parenchymal inflammation and emphysema. They also developed mucus metaplasia reminiscent of chronic bronchitis.

The IL-13 promoter polymorphism (−1055 C to T) that is associated with allergic asthma has also been reported to have an increased frequency in COPD patients compared to healthy controls. This implies a functional role for the IL-promoter polymorphism in the enhanced risk to develop COPD (Kraan et al, *Genes and Immunity* 3:436-439, 2002). In addition, an increased number of IL-13 and IL-4 positive cells were observed in smokers with chronic bronchitis compared to asymptomatic smokers (Miotto et al, *Eur. Resp. J.* 22:602-608, 2003). However, a recent study to assess the level of IL-13 expression in the lungs of severe emphysema patients did not find an association between IL-13 levels and disease (Boutten et al, *Thorax* 59:850-854, 2004).

IL-13 has also been implicated in atopic disorders such as atopic rhinitis and atopic dermatitis. Allergic rhinitis is the most common atopic disease in the United States and is estimated to affect up to 25% of adults and more than 40% of children. There is a close relationship between allergic rhinitis and asthma. Both conditions share common immunopathology and pathophysiology; they have similar immunologic processes in which eosinophils and Th2 lymphocytes in nasal and bronchial tissue play a role. Excessive production of Th2 cytokines, particularly IL-4 and IL-5, is thought to be fundamental in the pathogenesis of allergic disease. IL-13 shares several characteristics and effecter functions with IL-4 and this, combined with the functional overlap in IL-4 and IL-13 receptor usage, intracellular signaling components, and genetic organization provides compelling (albeit indirect) evidence for a role of IL-13 in promoting or maintaining human immediate hypersensitivity in vivo. This has been corroborated by Li et al. (Li et al, *J Immunol* 161:7007, 1998) who demonstrated that atopic subjects with seasonal allergic rhinitis exhibited significantly stronger IL-13 responses in response to antigen-dependent but not polyclonal activation.

Atopic dermatitis is a common, chronic, relapsing, highly pruritic inflammatory skin disease. The lesional skin of atopic dermatitis patients is histologically characterized by an inflammatory T-cell infiltrate, which during acute phases is associated with a predominance of IL-4, IL-5 and IL-13 expression (Simon et al, *J Allergy Clin Immunol* 114:887, 2004; Hamid et al, *J Allergy Clin Immunol* 98:225, 1996). In addition, Tazawa et al, *Arch Derm Res* 296:459, 2004, have demonstrated that IL-13 mRNA (but not IL-4) is significantly upregulated in subacute and chronic skin lesions of atopic dermatitis patients. The frequency of IL-13 expressing circulating CD4+ and CD8+ T cells is also significantly increased in these patients (Aleksza et al, *British J Dermatol* 147; 1135, 2002). This increased IL-13 activity is thought to result in raised levels of serum IgE, thereby contributing to the pathogenesis of atopic dermatitis. Furthermore, increased production of IL-13 by neonatal CD4+ T cells is a useful marker for identifying newborns at high risk for subsequent development of allergic diseases, especially atopic dermatitis (Ohshima et al, *Pediatr Res* 51:195, 2002). Additional evidence for the importance of IL-13 in the etiology of atopic dermatitis was provided by Simon et al, 2004 supra; topical treatment with tacrolimus ointment (an immunosuppressive drug that inhibits intracellular signaling pathways for cytokine production) resulted in significant clinical and histological improvement of the atopic skin lesions accompanied by significant reductions in local expression of Th2 cytokines, including IL-13. Furthermore, IL-13Rα1 has been shown to be overexpressed on the suprabasal keratinocytes in the skin of atopic dermatitis patients, and IL-13 was able to upregulate IL-13Rα1 mRNA in vitro (Wongpiyabovorn et al, *J Dermatol Science* 33:31, 2003).

These data collectively indicate that IL-13 targeted interventions may provide an effective approach for treatment of human allergic disease.

The accumulation of eosinophils in the esophagus is a common medical problem in patients with diverse diseases, including gastro-esophageal reflux disease, eosinophilic esophagitis, eosinophilic gastroenteritis, and parasitic infections. Esophageal eosinophilia is associated with allergic responses, and repeated challenging of mice with aeroallergens established a link between allergic airway inflammation and esophagal eosinophilia. Th2 cells are thought to induce eosinophil-associated inflammation through the secretion of an array of cytokines including IL-4 and IL-13 that activate inflammatory and effector pathways both directly and indirectly. IL-13 appears to be particularly important because it is produced in high quantities by Th2-cells and regulates multiple features of allergic disease (e.g., IgE production, mucus over-production, eosinophil recruitment and survival, and airway hyperreactivity. Eosinophils can generate functionally active IL-13 after exposure to GM-CSF and/or IL-5 under in vitro, ex vivo, and in vivo conditions in eosinophilic inflammatory responses (Schmid-Grendelmeier, *J Immunology*, 169:1021-1027, 2002). IL-13 delivered to the lung of wild-type, STAT-6, eotaxin-1 or IL-5-deficient mice by intratracheal administration, established that pulmonary inflammation, triggered by IL-13, is associated with the development of esophagal eosinophilia (Mishra et al, *Gastroenterol;* 125: 1419, 2003). Taken together, these data provide evidence for a role of IL-13 in esophagal eosinophilia.

Another important area of interest is in targeting IL-13 or IL-13 receptors to inhibit growth of certain types of tumors. Type 1 T-cell mediated host defenses are believed to mediate optimal tumor rejection in vivo, and deviation to a Th2-type response may contribute to blocking tumor rejection and/or promotion of tumor recurrence (Kobayashi et al, *J. Immunol.* 160:5869, 1998). Several animal studies using transplantable tumor cell lines support this notion by demonstrating that STAT6, IL-4, and IL-13 (produced in part by NKT cells) were capable of inhibiting tumor rejection (Terabe et al, *Nat. Immunol.* 1:515, 2000; Kacha et al, *J. Immunol.* 165:6024-28, 2000; Ostrand-Rosenberg et al, *J. Immunol.* 165:6015, 2000). The potent anti-tumor activity in the absence of STAT6 was thought to be due to enhancement of tumor-specific IFNγ production and CTL activity. In addition, a loss of NKT cells has been shown to reduce IL-13 production with a concomitant rise in tumor recurrence, indicating that IL-13, produced in part by NKT cells is important for immunosurveillance (Terabe et al, 2000 supra). As such, these findings suggest that IL-13 inhibitors may be effective as cancer immunotherapeutics by interfering with the negative regulatory role IL-13 plays in down-regulating immune responses to tumor cells.

In addition to boosting Th-type-1-associated anti-tumor defenses, IL-13 inhibitors may also be able to block tumor cell growth more directly. For example, in B-cell chronic lymphocytic leukemia (B-CLL) and Hodgkin's disease, IL-13 either blocks apoptosis or promotes tumor cell proliferation (Chaouchi et al, *Blood* 87:1022, 1996; Kapp et al, *J. Exp Med.* 189:1939, 1999). B-CLL is a clinically heterogeneous disease originating from B lymphocytes that involves apoptotic defect in the leukemic cells. IL-13 is not thought to act as a direct growth factor but protects tumor cells from in vitro spontaneous apoptosis (Chaouchi et al, 1996 supra; Lai et al, *J. Immunol* 162:78, 1999) and may contribute to B-CLL by preventing neoplastic cell death.

Hodgkin's disease is a type of lymphoma that primarily affects young adults and accounts for about 7,500 cases a year in the United States. The cancer is characterized by the presence of large multi-nucleated Hodgkin/Reed-Sternberg cells (H/RS). In a large majority of cases, the malignant cell population arises from B cells. Several Hodgkin's disease derived cell lines, as well as lymph node tissue taken from Hodgkin's lymphoma patients, overexpress IL-13 and/or IL-13 receptors (Kapp et al, 1999 supra; Billard et al, *Eur Cytokine Netw* 8:19, 1997; Skinnider et al, *Blood* 97:250, 2001; Oshima et al, *Cell Immunol* 211:37, 2001). Neutralizing anti-IL-13 mAbs or IL-13 antagonists have been shown to inhibit H/RS cell proliferation in a dose-dependent manner (Kapp et al, 1999 supra; Oshima et al, 2001 supra). Similarly, delivery of soluble IL-13Rα2 decoy receptor to NOD/SCID mice with an implanted Hodgkin's disease-derived cell line delayed tumor onset and growth, and enhanced survival, demonstrating that IL-13 neutralization can suppress Hodgkin's lymphoma growth in vitro and in vivo (Trieu et al, *Cancer Research* 64:3271, 2004). Collectively, these studies indicate that IL-13 stimulates the proliferation of H/RS cells in an autocrine fashion (Kapp et al, 1999 supra; Ohshima et al, *Histopathology* 38:368, 2001).

Neutralization of IL-13 may therefore represent an attractive and effective treatment for Hodgkin's disease and other B cell-associated cancers by inhibiting tumor cell growth while at the same time enhancing anti-tumor defenses.

There is a possible role for IL-13 in the pathogenesis of inflammatory I bowel disease (IBD). Inflammatory bowel disease includes a number of diseases clinically classified as ulcerative colitis, Crohn's disease and indeterminate colitis. Its main manifestation is chronic intestinal inflammation due to an exaggerated immune response with an imbalance in the activation of Th1 and Th2 lymphocytes in the intestinal mucosa. This has been demonstrated in animal models of Crohn's disease (Bamias et al, *Gastroenterol* 128:657, 2005)

and ulcerative colitis (Heller et al, *Immunity* 17:629, 2002). Neutralization of IL-13 by IL-13Rα2-Fc administration prevented colitis in a murine Th2 model of human ulcerative colitis (Heller et al, 2002 supra). Furthermore, IL-13 production rapidly supersedes that of IL-4 in this model, and IL-13 production can be induced by stimulation of NKT cells, suggesting that tissue damage may result from toxic activity of IL-13 on the epithelium cells. There are some human data to support these findings: the frequency of IL-13 positive rectal biopsy specimens from patients with ulcerative colitis was significantly higher than of inflammatory and non inflammatory control subjects, and a higher rate IL-4 and IL-13 expression was observed in acute than non-acute ulcerative colitis (Inoue et al, *Am J Gastroenterol* 94:2441, 1999). In addition, Akido et al characterized the immune activity in the muscularis externa from intestinal segments of Crohn's disease patients and found that IL-4 and IL-13 mediate hypercontractility of the intestinal smooth muscle cells via a STAT6 pathway. The authors concluded that this pathway may contribute to the hypercontractility of intestinal muscles in Crohn's disease (Akiho et al, *Am J Physiol Gastrointest Liver Physiol* 288:619, 2005). Thus, an IL-13 antagonist may provide an approach to stop or slow the progression of IBDs.

Psoriasis is a chronic skin disease characterized by hyperproliferation of keratinocytes and an immunologic cellular infiltrate, including activated T cells, producing various cytokines that can influence the phenotype of epidermal keratinocytes. CDw60 is a carbohydrate-bearing molecule that is upregulated on the surface of psoriatic basal and suprabasal keratinocytes of psoriatic skin. IL-4 and IL-13 secreted from T cells derived from psoriatic lesions have been shown to strongly upregulate the expression of CDw60 on keratinocytes (Skov et al, *Am J Pathol* 15:675, 1997), whereas interferon-gamma blocked IL-4/IL-13-mediated induction of CDw60 on cultured keratinocytes (Huang et al, *J Invest Dermatol* 116:305, 2001). Thus, CDw60 expression on psoriatic epidermal keratinocytes is thought to be induced at least in part by IL-13 secreted by activated T cells within the lesion. In addition, IL-13Rα1 and IL-4Rα are differently expressed in skin biopsies from patients with and without psoriasis (Cancino-Diaz et al, *J Invest Dermatol* 119:1114, 2002; Wongpiyabovorn et al, 2003 supra), and in vitro experiments demonstrated that IL-13 (but not IL-4) could upregulate the expression of IL-13Rα1 (Wongpiyabovorn et al, 2003 supra). Since IL-13 has an effect on a variety of cell types, these studies suggest that the IL-13 receptor may play a part in the early inflammatory process of psoriasis.

Psoriatic arthritis is characterized by synovitis which is mediated by both pro-inflammatory and anti-inflammatory cytokines. The role of IL-13 in various forms of arthritis has been receiving increased interest. Spadaro et al, *Ann Rheum Dis* 61:174, 2002 have observed significantly higher levels of IL-13 in synovial fluid of patients with psoriatic arthritis and rheumatoid arthritis than in patients with osteoarthritis. In addition, synovial fluid levels of IL-13 were significantly higher than those in serum in patients with psoriatic arthritis, and the IL-13 synovial fluid/serum ratio was markedly higher in the psoriatic arthritis group than in the rheumatoid arthritis group, suggesting a possible role for the locally produced IL-13 in synovial tissues of patients with psoriatic arthritis.

Acute graft-versus-host disease is a serious cause of morbidity and mortality following stem cell transplantation and is directly related to the degree of human leukocyte antigen (HLA) incompatibility between donor and recipient. Jordan et al first identified IL-13 as a typical Th2 cytokine that is abundantly produced during unrelated, unmatched MLRs (mixed lymphocyte reaction; an in vitro assay for fine-tuning donor selection after initial HLA typing) (Jordan et al, *J Immunol Methods* 260:1, 2002). The same group subsequently showed that IL-13 production by donor T cells is predictive of acute graft-versus-host-disease (aGVHD) following unrelated donor stem cell transplantation (Jordan et al., *Blood* 2004; 103:717). All patients with severe, grade III aGVHD following stem cell transplantation had donors who produced very high pre-transplantation IL 13 responses, demonstrating a significant link between IL-13 levels and aGVHD and raising the possibility that IL-13 may be directly responsible for some of the aGVHD associated pathology. Consequently, a therapy based on specific blocking of IL-13 may be useful for the treatment of post-stem cell transplantation aGVHD.

Diabetic nephropathy is one of the major causes of end stage renal disease in the Western world. Although the incidence of nephropathy owing to type 1 diabetes is declining, diabetes mellitus type 2 is now the most common single cause of renal insufficiency in the USA, Japan and Europe. Furthermore, this group of patients has a very poor prognosis on maintenance dialysis owing to extremely high mortality caused by cardiovascular events. It is now increasingly clear that hemodynamic, metabolic and structural changes are interwoven, and various enzymes, transcription factors and growth factors have been identified that play a role in the pathogenesis of this disease. Particularly, TGF-β is important in the development of renal hypertrophy and accumulation of extracellular matrix components, and is considered the pivotal cytokine in mediating collagen formation in the kidney (Cooper, *Diabetologia* 44:1957, 2001; Wolf, *Eur J Olin Invest* 34 (12):785, 2004). In experimental and human diabetic nephropathy TGF-1 bioactivity is increased and administration of TGF-β1 antibodies to a diabetic mouse led to improvement in renal function and reduced extra-cellular matrix accumulation. IL-13 was recently shown; in a transgenic mouse model of lung fibrosis to mediate its effects at least in part by regulating the production and activation of TGF-β1 and collagen deposition (Lee et al, *J. Exp. Med.* 194:809, 2001; Zhu et al, 1999 supra), thereby establishing a direct functional link between IL-13 and TGF-β. Consequently a similar role for IL-13 in regulating TGF-β1 activity in the diabetic kidney can be envisioned and IL 13 targeted interventions could potentially have a role in the management of diabetic nephropathy.

Pulmonary fibrosis is a condition of inappropriate and harmful scarring of the lungs, leading to disability and often death. The term encompasses a variety of different conditions with distinct etiologies, pathologies and responses to treatment. In some cases the cause of the fibrosis is identified. Causes include: inhaled profibrotic material such as asbestos or silicon, or hard metal dust; inhaled organic material to which the patient has an idiosyncratic immunological response leading to fibrosis (e.g., farmer's lung); drugs, such as nitrofurantoin, amiodarone and methotrexate; and an association with a systemic inflammatory disease, such as Systemic Sclerosis or Rheumatoid Arthritis.

However, in many instances no cause or underlying condition is identified. Many such patients are diagnosed with Idiopathic Pulmonary Fibrosis (IPF). This is a relatively rare condition (prevalence 20/100,000). The diagnosis is based on the absence of an identified cause combined with certain radiological and pathological features, particularly honeycombing on the CT or lung biopsy. The disease is usually seen in older patients (>50) and often follows a relentless course of progressive lung impairment leading to death, with the median survival quoted as 2-5 years. Moreover, the patients have the most unpleasant experience of breathlessness progressing over months or years. This initially restricts physical activity, but in the terminal phase, which may last several months, the patient is breathless even at rest and is furthermore oxygen dependent.

At present there is no satisfactory treatment for this disease. Current treatment generally takes the form of corticosteroids and immunosuppressives such as azathioprine. However, corticosteroids may be ineffective in many of patients and their side effects may make the situation worse. There are many potential treatments under investigation including interferon gamma, which has shown a trend to improved survival in a recent large study, and perfenidone.

There is evidence that IL-13 and cytokines associated with the Th2 phenotype are involved in the process of fibrosis in tissue repair (Wynn, Nat. Rev. Immunol. 4:583-594, 2004; Jakubzick et al, Am. J. Pathol. 164(6):1989-2001, 2004; Jakubzick et al, Immunol. Res. 30(3):339-349, 2004; Jakubzick et al, J. Clin. Pathol. 57:477-486, 2004). IL-13 and IL-4 have been implicated in a variety of fibrotic conditions. Hepatic fibrosis induced by Schistosoma appears to be IL-13 dependent and there is limited evidence that IL-13 is involved in the pathogenesis of scleroderma (Hasegawa et al, J. Rheumatol. 24:328-332, 1997; Riccieri et al, Clin. Rheumatol. 22:102-106, 2003).

In terms of pulmonary fibrosis, in vitro studies have shown that IL-13 promotes a fibrogenic phenotype. Animal studies have shown elevated levels of IL-13 expression in artificially induced models of fibrosis, and that fibrosis can be reduced by elimination of IL-13.

IL-13 promotes a profibrotic phenotype. At a cellular level, there are several mechanisms by which IL-13 may promote fibrosis. The signal pathways and importance of these various mechanisms are not well defined.

There is evidence that IL-13 acts on the fibroblast both to promote the production of collagen, and to inhibit its breakdown, thus favoring a fibrotic phenotype. Skin fibroblasts possess IL-13 receptors and exposure of cultured skin fibroblasts to IL-13 leads to upregulation of collagen generation (Oriente et al, J. Pharmacol. Exp. Ther. 292:988-994, 2000). IL-4 also has a similar, but more transitory effect. A human lung fibroblast cell line (ICIG7) expresses the type II IL-4 receptor (Jinnin et al, J. Biol. Chem 279:41783-41791, 2004). Exposure of these cells to IL-13 promotes secretion of a variety of inflammatory and profibrotic mediators: GM-CSF, G-CSF, VCAM beta1 integrin (Doucet et al, Int. Immunol. 10(10):1421-1433, 1998).

IL-13 inhibits IL-1a-induced matrix metalloproteinases 1 and 3 protein production by skin fibroblasts which would tend to reduce breakdown of EC matrix (Oriente et al, 2000 supra). IL-13 acts synergistically with TGF-β on human fibroblasts obtained by biopsy of asthma airways to promote expression of tissue inhibitor of metalloproteinase 1 (TIMP-1). Breakdown of extracellular matrix is effected by matrix metalloproteinases, which are inhibited by TIMP-1. This action of IL-13 would thus tend to reduce matrix degradation (Zhou et al, Am. J. Physiol. Cell Physiol. 288:C435-C442, 2005).

Over-expression of IL-13 in transgenic mice leads to subepithelial fibrosis, epithelial cell hypertrophy, goblet cell hyperplasia, crystal deposition (acidic mammalian chitinase), airway hyper-responsiveness, interstitial fibrosis, type 2 cell hypertrophy and surfactant accumulation (Zhu et al, 1999 supra).

Different strains of mice have different susceptibilities to bleomycin induced pulmonary fibrosis. C57B1/6J mice, which are susceptible, exhibit rapid up regulation of IL-13, IL-13Rα and IL-4 (as well as TGFβ, TNFRα and IL-1 receptors) in response to bleomycin. BALB/c mice, which are not susceptible, do not show upregulation of IL-13.

Belperio et al, Am. J. Respir. Cell Mol. Biol. 27:419-427, 2002, studied the expression and role of IL-13, IL-4 and the CC chemokine C10 in a mouse bleomycin fibrosis model. Lung tissue levels of both IL-13 and IL-4 increased in response to bleomycin. Prior neutralization of IL-13 using polyclonal anti IL-13 antibodies significantly reduced lung fibrosis in response to bleomycin as assessed by lung hydroxyproline levels. Despite the increased expression of IL-4 in the same model, neutralization of IL-4 had no effect on lung fibrosis.

In another model of acute lung fibrosis induced by FITC in the BALB/c mouse, absence of IL-13 (in knockouts), but not IL-4, protected against lung fibrosis. There is no added protection of knockout of IL-4 in IL-13 knockouts (Kolodsick et al, J. Immunol. 172:4068-4076, 2004). The protective effect of IL-13 absence is not due to a difference in cell recruitment into the lung in all knockouts and BALB/c total cell numbers recruited are similar, so the initial inflammatory component seems to be the unaffected. Eosinophil recruitment is lower in IL-4 and IL-13 knockouts compared with BALE/c, but since IL-4$^{-/-}$ were not protected against fibrosis this cannot explain the difference in fibrosis. Perhaps surprisingly, there was no difference in the levels of cytokines between IL 13$^{+/+}$ and $^{-/-}$ including for IL-10, MCP-1, gamma interferon, TGF-β1. In addition, the same number of fibroblasts were isolated from lungs of the different animals post FITC, but in the IL-13$^{-/-}$ mice the production of collagen is reduced. This indicates the loss of IL-13 is not simply preventing the inflammatory response, but rather is having a more specific anti-fibrotic role. It has been suggested that IL-13 might exert its fibrotic effect via TGF-β1 (Lee et al, 2001 supra). However, in this FITC model, expression of TGF-β1 was not reduced in IL-13 knock-out mice.

Interleukin-4 may be expected to exert a similar effect as IL-13 as both act via the same receptor. IL-4 is significantly upregulated in the lungs of mice with bleomycin induced lung fibrosis (Gharaee-Kermani et al, Cytokine 2001 15:138-147). However, comparing bleomycin-induced lung fibrosis in C57BL6/J mice which overexpress IL-4, IL-4 knockouts and wild-type, Izbicki et al, Am. J. Physiol. Lung Cell Mol. Physiol 283(5):L1110-L1116, 2002, did not find evidence that IL-4 was involved in lung fibrosis. Fibrosis was not reduced in IL-4 knockouts, and IL-4 over-expressing mice had increased levels of fibrosis.

BAL cytokine levels of IL-13 are significantly elevated in patients with a variety of forms of pulmonary fibrosis, though with considerable variability. Expression of IL-13 is significantly upregulated in alveolar macrophages obtained from patients with lung fibrosis.

The strongest clinical evidence comes from research at the University of Michigan. Jakubzick and colleagues have studied gene expression of IL-13 and IL-4 and their receptors in surgical lung biopsies from patients with pulmonary fibrosis. IL-13 gene expression is markedly greater in specimens from IPF-affected lung than lung from normals or other lung fibrotic conditions. Fibroblasts cultured from patients with IPF/UIP show heightened expression of the IL-13 and IL-4 receptor, compared with tissue and fibroblasts obtained biopsies from patients with normal lungs or other forms of lung fibrosis. In particular, the fibroblastic foci, which are presumably the epicentre of disease activity, stain particularly strongly for these receptors (Jakubzick et al, J. Immunol 171:2684-2693, 2003; Jakubzick et al, Am. J. Pathol. 162: 1475-1486, 2003; Jakubzick et al, 2004 supra; Jakubzick et al., 2004 supra; Jakubzick et al, 2004 supra).

There is good in vitro evidence that Th2 cytokines in general and IL-13 in particular promote a profibrotic phenotype. In at least two animal models it has been shown that chemically-induced fibrosis can be reduced by elimination of IL-13 (either in gene knock-out or by anti-IL-13 antibodies). Some evidence indicates that IL-13 is more important at promoting pulmonary fibrosis than IL-4. Clinical evidence for the role of IL-13 in pulmonary fibrosis suggests that IL-13 and its receptors are unregulated in the lungs of patients with IPF.

A growing body of data suggests an important role for IL-13 antagonist based therapies for the treatment of a variety of fibrotic conditions, including schistosomiasis-induced hepatic fibrosis, and various forms of pulmonary fibrosis (e.g., IPF, scleroderma).

Experiments in which IL-4 and IL-13 were inhibited independently identified IL-13 as the dominant effecter cytokine of fibrosis in several models (Chiaramonte et al, *J. Clin. Invest.* 104:777-785, 1999; Blease et al, 2001 supra; Kumar et al, *Clin. Exp. Allergy* 32:1104, 2002). In schistosomiasis, although the egg-induced inflammatory response was unaffected by IL-13 blockade, collagen deposition decreased by more than 85% in chronically infected animals (Chiaramonte et al, 1999 supra; Chiaramonte et al, *Hepatology* 34:273, 2001) despite continued and undiminished production of IL-4.

Gene Therapy.

The anti-hIL-13Rα1 antibodies of the invention may also be administered to a subject in a gene therapy approach. In a gene therapy approach, the cells of a subject are transformed with nucleic acids which encode the antibodies of the invention. Subjects harboring the nucleic acids will then produce the antibody molecules endogenously. Previously, Alvarez, et al, *Clinical Cancer Research* 6:3081-3087, 2000, introduced single-chain anti-ErbB2 antibodies to subjects using a gene therapy approach. The methods disclosed by Alvarez, et al, may be easily adapted for the introduction of nucleic acids encoding an anti-hIL-13Rα1 antibody of the invention to a subject.

Although nucleic acids encoding any polypeptide or antibody molecule of the invention may be introduced to a subject, in specific embodiments, the antibody molecule is a human, single-chain antibody.

The nucleic acids may be introduced to the cells of a subject by any means known in the art. In specific embodiments, the nucleic acids are introduced as part of a viral vector. Examples of specific viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, AVIGEN, Inc. (Alameda, Calif.; AAV vectors), Cell Genesys (Foster City, Calif.; retroviral, adenoviral, AAV vectors, and lentiviral vectors), CLONTECH (retroviral and baculoviral vectors), Genovo, Inc. (Sharon Hill, Pa.; adenoviral and AAV vectors), GENVEC (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). In specific embodiments, the viral vectors are replication defective, that is, they are unable to replicate autonomously, and thus are not infectious, in the target cell. Preferably, the replication defective virus may be a minimal virus, i.e., it retains only the sequences of its genome which are necessary for encapsidating the genome to produce viral particles. Defective viruses, which entirely or almost entirely lack viral genes, may be used as well. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno et al, *Cancer Gen. Ther.* 6:147-154, 1999; Kaplitt et al, *J. Neurosci. Meth.* 71:125-132, 1997 and Kaplitt et al, *J. Neuro Onc.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992 are desirable in some instances. Various replication defective adenovirus and minimum adenovirus vectors have been described (WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al, *Gene Ther.* 8:1343-1346, 2001, Larson et al, *Adv. Exp. Med. Bio.* 489:45-57, 2001; WO 91/18088 and WO 93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.*, 62:1120, 1988; EP 453242 and EP178220. The retroviruses are integrating viruses which infect dividing cells.

Lentiviral vectors can be used as agents for the direct delivery and sustained expression of nucleic acids encoding an antibody molecule of the invention in several tissue types, including brain, retina, muscle, liver and blood. The vectors can efficiently transduce dividing and nondividing cells in these tissues, and maintain long-term expression of the antibody molecule. For a review, see Zufferey et al, *J. Virol.* 72:9873-80, 1998 and Kafri et al, *Curr. Opin. Mol. Ther.* 3:316-326, 2001. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than $10^6$ IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus et al, *Microbiol. Rev.*, 58:491-562, 1994; Bredenbeek et al, *J. Virol.*, 67:6439-6446, 1993; Ijima et al,

*Int. J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for gene therapy has been described. (Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in WO 95/18863 and WO 96/17823, and in U.S. Pat. No. 5,459,127.

It is also possible to introduce the vector in vivo as a naked DNA plasmid. Naked DNA vectors for gene therapy can be introduced into the desired host cells by methods known in the art, e.g., electroporation, microinjection, cell fusion, DEAE-dextran, calcium phosphate precipitation, use of a gene gun, or use of a DNA vector transporter (see, e.g., Wilson, et al, *J. Biol. Chem.* 267:963-967, 1992; Williams et al, *Proc. Natl. Acad. Sci. USA* 88:2726-2730, 1991). Receptor-mediated DNA delivery approaches can also be used (Wu et al, *J. Biol. Chem.* 263:14621-14624, 1988). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, *Bioelectrochemistry* 53:1-10, 2001; WO 99/01157, WO 99/01158 and WO 99/01175).

Pharmaceutical compositions suitable for such gene therapy approaches and including nucleic acids encoding an anti-hIL-13Rα1 antibody of the invention are within the scope of the present invention.

The present invention is further illustrated by the following examples which should not be construed as further limiting.

Example 1

Production and Purification of a Recombinant Protein Based on the Human IL-13Rα1 Extracellular Region A pEFBOS-S-FLAG® expression vector incorporating a cDNA encoding most of the extracellular region (ECR) of human IL-13Rα1 (i.e., amino acids number 3 to 317 of SEQ ID NO:1) with an IL-3 signal sequence and FLAG®-tag fusion was transfected into CHO cells for stable expression using standard procedures. N-terminal FLAG®-tagged fusion protein including most of the extracellular region of human IL-13Rα1 (referred to as "hIL-13Rα1.ECR") (SEQ ID NO:28) was purified from culture media conditioned by the CHO cell clone. The purified protein was concentrated and subsequently desalted into phosphate-buffered saline (PBS), 0.02% v/v TWEEN™ 20, followed by filter sterilization. Typical recovery was 0.4 mg protein per liter of conditioned media. Protein was stored at −80° C. until required.

Example 2

Generation of Hybridoma Cell Lines Producing Human Anti-Human IL-13Rα1 Monoclonal Antibodies Immunization of Transgenic Mice.

Male and female transgenic mice from the HCo7, HCo12 and HCo7×HCo12 strains (HUMAB™ mice, Medarex, USA) were immunized with hIL-13Rα1.ECR of Example 1. For the first immunization, 20-50 µg of hIL-13Rα1.ECR was emulsified in Complete Freund's Adjuvant (CFA) and administered via the intraperitoneal (i.p.) route. For a minimum of two and a maximum of three subsequent i.p. immunizations, 20-50 µg of hIL-13Rα1.ECR was emulsified in Incomplete Freund's Adjuvant (IFA). Following the second or third immunization with hIL-13Rα1.ECR in IFA, serum was sampled (retro-orbital plexus) and assayed for human antibodies against the hIL-13Rα1.ECR by ELISA (see below). High-responder mice (serum titers generally >1:3200) were selected for hybridoma generation. In some cases, animals not used for hybridoma generation at this point received further i.p. immunizations with 20-50 µg of hIL-13Rα1.ECR in PBS. Serum from these animals was again assayed for human antibodies against the hIL-13Rα1.ECR by ELISA and high-responder mice were used for hybridoma generation. Mice selected for hybridoma generation were boosted intravenously with 20-50 µg of hIL-13Rα1.ECR 3-4 days prior to spleen cell fusion.

Antigen-Specific ELISA.

Mouse serum or hybridoma culture supernatant fluid (SNF) was assessed for mAbs able to bind to plate bound hIL-13Rα1.ECR using a standard ELISA format which included coating flat bottom 96-well MAXISORP™ plates (NUNC, Invitro Technologies, #439-454) with 50 µl of a solution containing 2.5 µg/ml hIL-13Rα1.ECR diluted in PBS, overnight at 4° C. After washing two times with PBS, plates were blocked with 2% w/v skim milk in PBS (blocking buffer, 200 µl/well) for 1 hour at 37° C. and subsequently washed two times with PBS containing 0.1% v/v TWEEN™ 20 (wash buffer). Fifty µl of test hybridoma SNF or mouse serum were added per well and plates were incubated at room temperature for 1 hour. Plates were washed three times. Bound human mAbs were detected using an anti-human IgG HRP-conjugated secondary reagent diluted 1:1000 in PBS containing 1% w/v skim milk powder and 0.1% v/v TWEEN™ 20 (50 µl/well, 1 hour at room temperature). The plates were washed three times, developed with TMB substrate, and read at OD 450 nm Hybridoma Generation.

Selected high-responder mice were sacrificed and the spleen and relevant lymph nodes were collected. The fusion of spleen and lymph node cells with the fusion partner SP2/0 and subsequent HAT (hypoxanthine/aminopterin/thymidine) (GIBCO, #21060-017) selection of hybridomas was performed according to standard procedures (*Antibodies: A Laboratory Manual*: Harlow and Lane. Cold Spring Harbor Laboratory Press). Briefly, medium for culturing cells was prepared after the fusion had been completed. The medium was hybridoma serum-free medium (HSFM) (GIBCO-BRL, #12045-084) with 5% Ultra low IgG FBS (FBS) (GIBCO-BRL, #16250-078), 2 mM GLUTAMAX™-1 (GIBCO-BRL, #35050-061), 50 U/50 µg/ml Penicillin/Streptomycin (GIBCO-BRL, #15070-063) and 1×HAT. All media was warmed to 37° C. SP2/O cells were harvested and a viable cell count was performed. Useful cells were healthy, actively dividing and in log-phase. In this regard, viability was >95%. SP2/O cells were cultured in HSFM/5% Ultra low IgG FBS prior to fusion, and split 1:2 or 1:3 on the day before the fusion.

On the day of fusion, the animal was sacrificed and the spleen (and lymph nodes if required) were immediately removed and placed into sterile medium (Dulbecco's modification of Eagles media (GIBCO-BRL, #11995-073) or DME) on ice.

A single cell suspension was prepared from the spleen, and washed twice (1800 rpm for 7 minutes) in DME, wherein the second wash was warm. The SP2/O cells were subsequently washed three times (1500 rpm, 7 minutes) with warm DME to remove all traces of serum.

SP2/O cells ($10^8$) for one mouse spleen were used in 2 separate fusions. SP2/O cells and spleen cells were pooled together in the same tube and centrifuged at 2100 rpm (400 g) for 5 minutes. All DME was removed, leaving only a combined cell pellet.

The cells were placed in a 37° C. heat block and 1 ml of warm PEG was added drop-wise to the cell pellet over 1 minute whilst stirring the pellet gently with the pipette. The pellet was stirred gently for another minute and 1 mL of warm DME was added drop-wise over 1 minute with stirring. Another 1 mL of DME was added over 1 minute followed by 20 ml DME over 5 minutes, with stirring. The cells were centrifuged for 5 minutes at 1500 rpm and the supernatant was removed. The cells were gently resuspended in culture medium and plated at 0.2 ml per well in HAT medium. Plates were fed by removing approximately 0.1 ml from each well and replacing with fresh HAT medium every 3 or 4 days.

Growth of hybridomas was examined at days 7-10, with screening at 10-14 days after the fusion. To screen for antibody production, ~100 µl supernatant was removed from each well for assay. Positives were transferred to 1 ml or 2 ml wells then gradually expanded to 6-well plates. Hybridomas were not clonal at this stage. After 14 days in HAT medium, hybridomas were cultured in HT (GIBCO-BRL, #11067-030) (HSFM, 5% Ultralow IgGFBS, 10 ng/ml rhIL-6 (R&D Systems, #206-IL-050) and HT) for approximately 2 more weeks then without HT.

Culture of Hybridomas. Hybridomas testing positive at primary and follow-up confirmation ELISA screens were cloned by limit dilution. Limit dilution wells containing single colonies were screened by ELISA and a positive well selected for expansion and further rounds of limit dilution cloning until 100% of wells test positive.

For production of supernatant fluid (SNF) for antibody purification hybridomas were expanded into either T175 $cm^2$ flasks (FALCON, #3028) or roller bottles (900 $cm^2$) (CORNING, #430849). Media used for generation of hybridoma SNFs was HSFM supplemented with 5% Ultralow IgG FBS, 2 mM glutamine and 50 U/50 µg/ml penicillin/streptomycin. Hybridomas were allowed to grow to confluence and media harvested by centrifugation approximately 5-10 days later when >90% of cells were dead. All conditioned media was filtered using a STERICUP™ filter apparatus (MILLIPORE, #SCGPU11RE) (0.45 µm) prior to mAb purification.

Production of Purified mAbs.

Monoclonal antibodies were purified from SNF using a standard Protein A affinity chromatography-based strategy.

Example 3

Identification of Anti-Human IL-13Rα1 Monoclonal Antibodies that Bind to Domain 3 of Human IL-13Rα1

The extracellular region of IL-13Rα1 is predicted to be composed of 3 fibronectin type III globular domains, each approximately 100 amino acids in length (Arima et al, supra). The amino terminal fibronectin type III domain (referred to here as domain 1 or D1) is followed by two other fibronectin type III domains (referred to here as domain 2 and domain 3, or D2 and D3 respectively) which comprise a cytokine receptor homology module (Wells and de Vos, 1996 supra). To predict the sequence boundaries of each of these fibronectin type III domains, the mature sequences of the extracellular regions of hIL-13Rα1 and hIL-4Rα were aligned. The approximately 200 residue extracellular region of hIL-4Rα is composed of a cytokine receptor homology module, corresponding to D2 and D3 of IL-13Rα1, but does not contain any upstream domain corresponding to D1. Accordingly, the first residue of mature hIL-4Rα was taken to define the boundary between D1 and D2 on the aligned hIL-13Rα1 sequence. The boundary between the two fibronectin type III domains in IL-4Rα, as deduced from the crystal structure (Hage et. al, 1999 supra), was then used to define the boundary between D2 and D3 in the aligned IL-13Rα1 sequence. Accordingly, D1 of ECR of hIL-13Rα1 corresponds to amino acids 1 to 100 of SEQ ID NO:1, D2 to amino acids 101 to 200, and D3 to amino acids 201 to 317.

Constructs were prepared encoding (i) the entire extracellular region of IL-13Rα1 (i.e., D1-D3), (ii) D2-D3, (iii) D1, (iv) D2 and (v) D3; in each case the relevant fragment of the extracellular region was fused via the C-terminus to a fragment of the gene 3 protein (amino acids 249-406) generally in accordance with the procedure described by Lowman et al, *Biochem*, 30:10832-8, 1991. These different fragments of extracellular region of hIL-13Rα1 were then displayed on the surface of M13 bacteriophage and assayed for their ability to bind mAbs.

Phage preparations displaying each of these 5 constructs were assayed by ELISA for binding to mAbs immobilized on 96-well plates. Briefly, mAbs were passively adsorbed onto 96-well MAXISORP™ plates (NUNC) following overnight incubation of 100 µL/well of 10 µg/mL anti-IL-13Rα1 mAb in PBS. Coating solutions were discarded, plates were blocked by incubation with skim milk powder solution for 1 hour at room temperature (5% w/v in PBS; blocking buffer), and then washed with PBS containing 0.1% v/v TWEEN™ 20 (wash buffer). *E. coli* supernatants, containing phage displayed IL-13Rα1 fragment, were diluted with blocking buffer (0.25 volumes), and added to mAb-coated wells (100 µL). Following incubation at room temperature for 2 hours, plates were washed 3 times, and bound phage labeled with anti-M13 IgG HRP-conjugated polyclonal antibody (AMERSHAM Biosciences), and detected by addition of TMB substrate (KPL Inc.). TMB color development was quenched by addition of 2 M aqueous sulfuric acid, and absorbance at 450 nm was measured.

Results. From the pool of antibodies providing positive ELISA results, mAbs displaying strong binding to D3-containing phage preparations (i.e., (i), (ii) and (v) above) were selected. Murine antibody 1D9 reported in WO 03/080675 and deposited at ECACC under deposit reference: 03032101 only bound to D2 containing phage preparations as did some other antibodies from the pool obtained from the use of the transgenic mice, including an antibody identified as 8B4.

Selected mAbs displaying strong binding to D3 included antibodies identified as 4B5, 4E2, 7D12, 8B11 and 15F4. Hybridomas expressing antibodies are referred to by the same names as the antibodies, or where a deposit has been made with the ATCC by the relevant deposit designation. Deposited hybridomas are listed in Table 3.

TABLE 3

| mAb | ATCC Deposit Designation for hybridoma |
|---|---|
| 4B5 | PTA-6931 |
| 8B11 | PTA-6936 |
| 15F4 | PTA-6935 |

Example 4

Analysis of the Affinity of Anti-Human IL-13Rα1 Monoclonal Antibodies for Human IL-13Rα1

BIACORE™-Based Studies.

Human IL-13Rα1.ECR (40 µg/ml in 20 mM Sodium Acetate, pH 4.2) of Example 1 was immobilized to a sensorchip (CM5, Biosensor, Sweden) using standard NHS/EDC chemistry according to the manufacturer's instructions at a set immobilization value, for example, 1000RU. Ethanolamine (1.0 M), pH 8.0 was used to quench residual active esters post hIL-13Rα1.ECR immobilization.

Analysis of binding of test mAbs (concentration range of 1.4 nM to 150 nM, two-fold dilutions) to the immobilized hIL-13Rα1.ECR was performed in duplicate. Sensorgrams generated were fitted to a bivalent ligand binding model to simultaneously derive association ($k_a$) and dissociation ($k_d$) rates and used to determine binding affinity ($K_D$, Biaevaluation software, BIACORE™, Sweden).

Results.

Examples of the binding affinities of anti-IL-13Rα1 human mAbs are presented in Table 4.

TABLE 4

| mAb | Affinity ($K_D$) |
|---|---|
| 4B5 | ~485 pM (n = 2) |
| 8B11 | ~288 pM (n = 2) |
| 15F4 | ~2.17 nM (n = 2) |

Example 5

Analysis of the Binding of Anti-Human IL-13Rα1 Monoclonal Antibodies to Cynomolgus Macaque and Mouse IL-13Rα1

A cDNA encoding the cynomolgus macaque IL-13Rα1 (cyIL-13Rα1) was cloned by PCR using mRNA extracted from cynomolgus spleen and bone marrow. The mature sequence was highly conserved between cynomolgus and human IL-13Rα1 with an amino acid identity of about 97% (see GENBANK accession No. AAP78901).

For production of purified cynomolgus IL-13Rα1.ECR protein, a cDNA encoding cynomolgus IL-13Rα1.ECR (amino acids 9 to 325 of GENBANK accession No. AAP78901 or amino acids 1 to 317 of SEQ ID NO:2) was cloned into the pEFBOS-S-FLAG® vector for expression as an N-terminal FLAG®-tagged fusion protein essentially as described above for the hIL-13Rα1.ECR.

Mouse IL-13Rα1.ECR (amino acids 27 to 344 of GENBANK accession No. 009030 or amino acids 1 to 318 of SEQ ID NO:3) was also expressed and purified as an N-terminal FLAG®-tagged fusion (mIL-13Rα1.ECR) essentially as described above.

The potential cross-reactivity of the selected mAbs raised against hIL-13Rα1.ECR with mouse and cynomolgus IL-13Rα1.ECR was assessed using a BIACORE™-based approach. Purified mouse, human and cynomolgus IL-13Rα1.ECR were immobilized individually to three channels of a sensorchip (CM5, BIACORE™, Sweden) using standard immobilization chemistry. Monoclonal antibodies (concentration range of 312.5 nM down to 125 pM) were assessed for binding to the receptors simultaneously at a flow rate of 15 µl/minute. Analysis of the affinity of mAbs was performed as described in Example 4 above.

Results.

Somewhat surprisingly, given the extent of sequence identity between the human and cynomolgus receptor, a number of mAbs exhibited significant differential binding (Table 5). For example, the mAb 8B11 showed very little, if any, binding to the cynomolgus receptor. In contrast, other mAbs such as mouse mAb, 1D9, bound equally well to both the human and cynomolgus receptors, while mAb 8B4 appeared to show some preference for the cynomolgus receptor. mAbs 4B5, 8B11 and 15F4 showed negligible binding to mouse receptor.

TABLE 5

| | Affinity ($K_D$) nM | |
|---|---|---|
| mAb | Cynomolgus IL13Rα.ECR | Human IL13Rα.ECR |
| 8B11 | 850 | ~0.288 |
| 8B4 | 0.59 | 4.6 |
| 1D9 | 0.247 | 0.207 |

Example 6

Analysis of the Ability of Anti-Human IL-13Rα1 Monoclonal Antibodies to Inhibit IL-13- and IL-4-Mediated Cellular Responses Normal Human Dermal Fibroblast (NHDF) Eotaxin Assay.

NHDF cells have been demonstrated to produce eotaxin in response to IL-13 and mAbs directed against the IL-13Rα1 may inhibit this response.

NHDF cells (Cambrex, #CC-2509) are cultured in FGM media (Cambrex, #CC3132) supplemented with the recommended additives according to the manufacturers instructions (complete media). Cells were passaged 1:3 or 1:5 once a week and monitored for responsiveness to IL-13 prior to use. To assess antagonist activity of hIL-13Rα1 specific mAbs, cells were resuspended to $2 \times 10^6$/ml in complete media containing 20 ng/ml PMA (SIGMA, #P8139) and 20 µg/ml polymyxin (SIGMA, #P4932) and plated in 96-well flat bottom plates (COSTAR, #3595) at $1 \times 10^5$ cell/well. Antibody titrations were added to the cells and incubated for 30 minutes, at 37° C. with 5% $CO_2$ in humidified air. Recombinant IL-13 (human or non-human primate) was then added to plates at a final concentration of 30 ng/ml and incubated overnight at 37° C. with 5% $CO_2$ in humidified air. For IL-4-induced assays, recombinant IL-4 (PHARMINGEN) was added to plates at a final concentration of 0.5 ng/ml in place of IL-13. Supernatants were then removed and assayed for eotaxin content by ELISA.

Eotaxin ELISA Protocol.

IMMULON®-4 plates (DYNATECH, #3855) were coated with 4 µg/ml mouse anti-human eotaxin antibody (R&D Systems, MAB320) in PBS (INVITROGEN, #14190-144), overnight at 4° C. Plates were blocked (200 µl/well, TBS supplemented with 1% BSA and 0.05% TWEEN™ 20) for 1 hour at room temperature and washed three times (wash buffer, TBS plus 0.05% TWEEN™ 20). Test SNF's from the NHDF cells were added (50 µl/well), plates were incubated for 2 hours at room temperature and subsequently washed three times. Biotinylated anti-human eotaxin antibody (R&D Systems, BAF320) at 200 ng/ml in blocking buffer was added, 60 ml/well, and plates were incubated for 1 hour at room temperature. Plates were washed three times and streptavidin-Europium (#1244-360, Wallac), 100 ng/ml in europium buffer, was added (100 µl/well). The plates were incubated for 20 minutes at room temperature and washed three times. Enhancement solution (#12244-105, Wallac), 150 µl/well, was added and the plates were incubated 1 hour at room temperature. Analysis was conducted via time-delayed fluorescence using a VICTOR (PERKIN ELMER) plate reader. Recombinant human eotaxin (R&D Systems, #320-EO) was used to establish a standard curve. Results of this analysis indicated that the $EC_{50}$ value of monoclonal antibody 8B11 was 21 µg/ml against IL-13 and 2.9 µg/ml against IL-4.

NHDF IL-13/IL-4-Induced STAT6 Phosphorylation Assay.

The phosphorylation of STAT6 (pSTAT6) is an essential element of IL-13/IL-4 signal transduction and occurs within minutes of receptor dimerization. IL-13Rα1-specific mAbs may block the phosphorylation of STAT6 in response to IL-13 and/or IL-4.

Thus, $2\times10^6$ NHDF cells in 50 µl of RPMI media (#22400-071, INVITROGEN) were plated into 96-well V-bottom polypropylene PCR plates (#1442-9596, USA scientific), and anti-IL-13R mAbs were added to the required concentration in 25 µl. Plates were incubated for 30 minutes at 4° C. Recombinant hIL-13 (100 ng/ml) or hIL-4 (PHARMINGEN) (0.5 ng/ml) was added in 25 µl and plates were warmed to 37° C. in a PCR machine for 20 minutes. After 20 minutes, an equal volume of 2× lysis buffer (100 mM HEPES, 200 mM NaCl, 2% v/v Triton™ X100, 100 mM NaF, 10 mM DTT, protease inhibitors) was added and pSTAT6 was measured by ELISA.

STAT6 ELISA Protocol.

IMMULON®-4 plates (#3855, DYNATECH) were coated with anti-human phospho STAT6 (621995, BD Transduction Labs) at 10 µg/ml in PBS (#14290-144, INVITROGEN) (50 µl/well) overnight at 4° C. Plates were blocked (200 µl/well, TBS supplemented with 1% BSA and 0.05% TWEEN™ 20) for 1 hour at room temperature and washed three times (wash buffer, TBS plus 0.05% v/v TWEEN™ 20). Test lysates were added at 50 µl/well, plates were incubated for 2 hours at room temperature and washed three times. Biotin anti-STAT6 (621141, BD Transduction Labs, conjugated to biotin 20:1 molar ratio) was added at 2 µg/ml in blocking buffer (60 µl/well) and plates were incubated for 1 hour at room temperature. Plates were washed three times, streptavidin-Europium (#1244-360, Wallac) at 100 ng/ml in europium buffer was added (100 µl/well), and plates were incubate for 20 minutes at room temperature. Plates were washed three times, enhancement solution (#12244-105, Wallac) was added (150 µl/well), and plates were incubated 1 hour at room temperature. Analysis was carried out via time-delayed fluorescence using a VICTOR (PERKIN ELMER) plate reader.

Results of this analysis indicated that the $EC_{50}$ value of monoclonal antibody 8B11 was 7.9 µg/ml against IL-13 and 5.3 µg/ml against IL-4.

Example 7

Competitive Binding of mAbs to hIL-13Rα1

ELISA-Based Strategy.

For ELISA-based competition analysis, the binding of biotinylated test mAb (sub-saturating concentration, biotinylated using standard procedures) to plate bound hIL-13Rα1.ECR, in the presence of a titrating unlabelled second mAb, was assessed as follows. Flat bottom 96-well MAX-ISORP™ plates (NUNC) were coated with 50 µl of a solution containing 2.5 µg/ml hIL-13Rα1.ECR diluted in PBS, overnight at 4° C. After washing two times in PBS, plates were blocked with 2% w/v Skim milk in PBS (blocking buffer, 200 µl/well) for 1 hour at 37° C., then washed a further two times in PBS, 0.1% v/v TWEEN™ 20 (wash buffer). Fifty µl, containing both biotinylated test mAb at a predetermined sub-saturating concentration and titrating unlabelled competitor mAb, were added per well and plates were incubated at room temperature for 1 hour. Plates were washed three times. Bound biotinylated mAbs were detected using a streptavidin-HRP-conjugated secondary reagent diluted 1:1000 in PBS, 1% w/v skim milk, 0.1% v/v TWEEN™ 20 (50 µl), 1 hour at room temperature. Plates were washed three times, developed with TMB substrate, and OD read at 450 nm.

Results.

The binding of biotinylated 4E2 was competed by unlabelled 4E2 as well as 4B5, 8B11 and 15F4, but not by 8B4. mAbs 8B4, and the mouse mAb 1D9, competed with each other Example 8

Mapping of Epitopes

Fine Mapping of Epitopes: Analysis of mAb Binding to Phage Displayed Chimeric Human/Mouse IL-13Rα1 Proteins.

Homolog-scanning mutagenesis (Cunningham B C et al, Science, 10; 243(4896):1330-6 (1989)) was used to further define the epitopes on hIL-13Rα1 for binding to different mAbs. As noted above, the mAbs were known not to bind to murine IL-13Rα1. Individual segments of sequences (5 to 9 amino acid residues long) derived from D3 of the murine IL-13Rα1 extracellular region (FIG. 1) were systematically substituted throughout the human IL-13Rα1 extracellular region sequence to produce a set of 11 chimeric receptors; i.e., each chimeric receptor included the human receptor extracellular region sequence with one segment of 5 to 9 amino acid residues replaced by the corresponding segment of the mouse extracellular region sequence; e.g., HM1 is the human IL-13Rα1 extracellular region with the underlined segment of the murine IL-13Rα1 identified as HM1 in FIG. 1 replacing the corresponding segment of the human IL-13Rα1 extracellular region. Each mAb was then analyzed against the panel of chimeric receptor proteins to determine which mutant receptors exhibited reduced binding.

Preparation of Panel of Human/Mouse IL-13Rα1 Proteins and ELISA Assay.

The panel of 11 chimeric IL-13Rα1 proteins were displayed on M13 bacteriophage as fusions to the gene 3 coat protein and were assayed for binding to anti-human IL-13Rα1 mAbs. Chimeric receptor proteins were also assayed for binding to the reference mAb 8B4, which binds to D2 of the IL-13Rα1 extracellular region, and the binding of which was therefore not affected by the mutations.

Phage preparations displaying chimeric IL13Rα1 proteins were assayed by ELISA for binding to immobilized mAbs. Briefly, mAbs were passively adsorbed onto 96-well MAXISORP™ plates (NUNC) following overnight incubation of 100 μL/well of 2.5 μg/mL mAb diluted in PBS buffer. Coating solutions were discarded, plates were blocked by incubation with blocking buffer for 1 hour at room temperature, then washed once with wash buffer. Phage samples serially diluted with 1% w/v skim milk powder in PBS (diluting buffer) were then transferred into mAb-coated plates (100 μL/well). Following incubation at room temperature for 2 hours, plates were washed 3 times, and bound phage labeled with anti-M13 IgG HRP-conjugated polyclonal antibody, and detected by addition of TMB substrate. TMB color development was quenched by addition of 2 M aqueous sulfuric acid, and absorbance at 450 nm was measured.

Data Analysis.

For each of HM1-HM11, the dilution of phage stock which resulted in half-maximal ELISA signal for binding to a given test mAb ($EC_{50}$) was divided by $EC_{50\text{-}REF}$; the dilution of phage stock resulting in half-maximal binding to the reference mAb 8B4. For each mAb tested, $EC_{50}/EC_{50\text{-}REF}$ values did not differ by more than 10-fold across chimeric receptor constructs, except where mutations appeared to significantly decrease receptor binding to mAb. A significant decrease was typically more than a 10-fold reduction in binding between an antibody and a particular chimeric receptor compared with binding between the antibody and other chimeric receptors where the mutations had little or no effect and antibody binding was essentially equivalent to that observed for wild type receptor.

Results.

Chimeric proteins which exhibited a significant decrease in mAb binding affinity are listed in Table 6. Most chimeric receptor proteins retained high affinity binding to the mAbs tested. Reduced binding was observed for mAbs to chimeric receptors HM5 and HM6. General trends revealed by this data indicate one or more of human IL-13Rα1 residues Val248, Phe249, Tyr250, Gln252, Ala254, Glu257, Pro259 are important for binding by some antibodies to domain 3. No reduction in binding was observed for reference mAb 8B4 or murine mAb 1D9.

TABLE 6

| mAb | Chimeric IL-13Rα1 |
|---|---|
| 4B5 | HM5, HM6 |
| 4E2 | HM5, HM6 |
| 7D12 | HM5, HM6 |
| 8B11 | HM5, HM6 |
| 15F4 | HM5, HM6 |

Fine Mapping of Epitopes: Analysis of mAb Binding to Phage Displayed Point Mutants of Human IL-13Rα1.

To define specific IL-13Rα1 residues contributing to mAb binding, single amino acid substitutions were made to the sequence of human IL-13Rα1 extracellular region. Point mutations were made in regions where the human receptor sequence differed from that of HM5 and HM6. Accordingly, the following 7 point mutants of hIL-13Rα1 extracellular region were prepared by site-directed mutagenesis: i) Val248Ala; ii) Phe249Ala; iii) Tyr250Ala; iv) Gln252Ala; v) Ala254Asp; vi) Glu257Ala; vii) Pro259Ala. The mutant IL-13Rα1 peptides were displayed on phage and assayed by ELISA for binding to test mAbs immobilized on 96-well plates, according to the same procedure as described above for human-mouse chimeric proteins. Reference mAb 8B4 was also assessed. Binding data obtained by ELISA was analyzed in the same manner as for human-mouse chimeric proteins.

Results.

Point mutations which exhibited a significant decrease in mAb binding are shown in Table 7.

TABLE 7

| mAb | Mutant IL-13Rα1 |
|---|---|
| 4B5 | Phe249Ala; Tyr250Ala; Gln252Ala |
| 4E2 | Phe249Ala; Tyr250Ala; Gln252Ala |
| 7D12 | Tyr250Ala; Gln252Ala; Ala254Asp |
| 8B11 | Phe249Ala; Tyr250Ala; Gln252Ala |
| 15F4 | Phe249Ala; Tyr250Ala; Gln252Ala; Ala254Asp |

Example 9

Cloning and Sequencing of the Murine Antibody Variable Regions

Messenger RNA was prepared from hybridoma cells producing the mAb and reverse-transcribed using an oligo-dT primer to produce cDNA. Partially degenerate PCR primers based on the amino-terminal amino acid sequence and the antibody isotype were used to amplify the mature heavy and light variable domains and incorporate restriction enzyme sites for cloning. The subsequent clones and PCR products were sequenced to reveal the amino acid sequence for the variable regions of 4B5, 8B11 and 15F4. Where N-terminal sequence corresponded to primer sequence but differed from germline, the sequence was amended to germline. For mAb 4B5, a pseudogene was identified for the light chain and further sequencing is required.

The nucleotide and amino acid sequences of the heavy chain variable region of 4B5 are shown in FIG. 2 and in SEQ ID NOs:21 and 4, respectively.

The nucleotide and amino acid sequences of the heavy chain variable region of 8B11 are shown in FIG. 3 and in SEQ ID NOs:25 and 8, respectively.

The nucleotide and amino acid sequences of the heavy chain variable region of 15F4 are shown in FIG. 4 and in SEQ ID NOs:29 and 12, respectively. The nucleotide and amino acid sequences of the light chain variable region of 15F4 are shown in FIG. 5 and in SEQ ID NOs:33 and 16, respectively.

Comparison of the 4B5 heavy chain immunoglobulin sequence to the known human germline immunoglobulin heavy chain sequences demonstrated that this antibody heavy chain utilizes a $V_H$ 3-30.3 segment from human germline $V_H$.

Comparison of the 8B11 heavy chain immunoglobulin sequence to the known human germline immunoglobulin heavy chain sequences demonstrated that this antibody heavy chain utilizes a $V_H$ segment from human germline $V_H$ 3-30.3.

Comparison of the 15F4 heavy chain immunoglobulin sequence to the known human germline immunoglobulin heavy chain sequences demonstrated that these antibody heavy chains utilizes a $V_H$ segment from human germline $V_H$ 3-33.

Comparison of the 15F4 light chain immunoglobulin sequence to the known human germline immunoglobulin light chain sequences demonstrated that these antibody light chains utilizes a $V_L$ segment from human germline $V_L$ VKIII A27.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

---

SEQUENCE LISTING

<160> NUMBER OF SEQ ID NOS: 46

<210> SEQ ID NO 1
<211> LENGTH: 401
<212> TYPE: PRT
<213> ORGANISM: Homo sapiens

<400> SEQUENCE: 1

```
Ala Pro Thr Glu Thr Gln Pro Pro Val Thr Asn Leu Ser Val Ser Val
1               5                   10                  15

Glu Asn Leu Cys Thr Val Ile Trp Thr Trp Asn Pro Pro Glu Gly Ala
            20                  25                  30

Ser Ser Asn Cys Ser Leu Trp Tyr Phe Ser His Phe Gly Asp Lys Gln
        35                  40                  45

Asp Lys Lys Ile Ala Pro Glu Thr Arg Arg Ser Ile Glu Val Pro Leu
    50                  55                  60

Asn Glu Arg Ile Cys Leu Gln Val Gly Ser Gln Cys Ser Thr Asn Glu
65                  70                  75                  80

Ser Glu Lys Pro Ser Ile Leu Val Glu Lys Cys Ile Ser Pro Pro Glu
                85                  90                  95

Gly Asp Pro Glu Ser Ala Val Thr Glu Leu Gln Cys Ile Trp His Asn
            100                 105                 110

Leu Ser Tyr Met Lys Cys Ser Trp Leu Pro Gly Arg Asn Thr Ser Pro
        115                 120                 125

Asp Thr Asn Tyr Thr Leu Tyr Tyr Trp His Arg Ser Leu Glu Lys Ile
    130                 135                 140

His Gln Cys Glu Asn Ile Phe Arg Glu Gly Gln Tyr Phe Gly Cys Ser
145                 150                 155                 160

Phe Asp Leu Thr Lys Val Lys Asp Ser Ser Phe Glu Gln His Ser Val
                165                 170                 175

Gln Ile Met Val Lys Asp Asn Ala Gly Lys Ile Lys Pro Ser Phe Asn
            180                 185                 190

Ile Val Pro Leu Thr Ser Arg Val Lys Pro Asp Pro His Ile Lys
        195                 200                 205

Asn Leu Ser Phe His Asn Asp Asp Leu Tyr Val Gln Trp Glu Asn Pro
    210                 215                 220

Gln Asn Phe Ile Ser Arg Cys Leu Phe Tyr Glu Val Glu Val Asn Asn
225                 230                 235                 240

Ser Gln Thr Glu Thr His Asn Val Phe Tyr Val Gln Glu Ala Lys Cys
                245                 250                 255

Glu Asn Pro Glu Phe Glu Arg Asn Val Glu Asn Thr Ser Cys Phe Met
            260                 265                 270

Val Pro Gly Val Leu Pro Asp Thr Leu Asn Thr Val Arg Ile Arg Val
        275                 280                 285

Lys Thr Asn Lys Leu Cys Tyr Glu Asp Asp Lys Leu Trp Ser Asn Trp
    290                 295                 300

Ser Gln Glu Met Ser Ile Gly Lys Lys Arg Asn Ser Thr Leu Tyr Ile
305                 310                 315                 320
```

Thr Met Leu Leu Ile Val Pro Val Ile Val Ala Gly Ala Ile Val
            325                 330                 335

Leu Leu Leu Tyr Leu Lys Arg Leu Lys Ile Ile Phe Pro Pro Ile
            340                 345                 350

Pro Asp Pro Gly Lys Ile Phe Lys Glu Met Phe Gly Asp Gln Asn Asp
            355                 360                 365

Asp Thr Leu His Trp Lys Lys Tyr Asp Ile Tyr Glu Lys Gln Thr Lys
    370                 375                 380

Glu Glu Thr Asp Ser Val Val Leu Ile Glu Asn Leu Lys Lys Ala Ser
385                 390                 395                 400

Gln

<210> SEQ ID NO 2
<211> LENGTH: 401
<212> TYPE: PRT
<213> ORGANISM: Macaca fascicularis

<400> SEQUENCE: 2

Ala Pro Thr Glu Thr Gln Pro Pro Val Thr Asn Leu Ser Val Ser Val
1               5                   10                  15

Glu Asn Leu Cys Thr Val Ile Trp Thr Trp Asn Pro Pro Glu Gly Ala
            20                  25                  30

Ser Pro Asn Cys Ser Leu Trp Tyr Phe Ser His Phe Gly Asp Lys Gln
            35                  40                  45

Asp Lys Lys Leu Ala Pro Glu Thr Arg Arg Ser Lys Glu Val Pro Leu
    50                  55                  60

Asn Glu Lys Ile Cys Leu Gln Val Gly Ser Gln Cys Ser Thr Asn Glu
65              70                  75                  80

Ser Glu Lys Pro Ser Ile Leu Val Glu Lys Cys Ile Ser Pro Pro Glu
            85                  90                  95

Gly Asp Pro Glu Ser Ala Val Thr Glu Leu Gln Cys Ile Trp His Asn
            100                 105                 110

Leu Ser Tyr Met Gln Cys Ser Trp Leu Pro Gly Arg Asn Thr Ser Pro
            115                 120                 125

Asp Thr Asn Tyr Thr Leu Tyr Tyr Trp His Arg Ser Leu Glu Lys Ile
    130                 135                 140

Arg Gln Cys Glu Glu Ile Tyr Lys Glu Gly Gln Tyr Phe Gly Cys Ser
145                 150                 155                 160

Phe Asp Leu Thr Lys Val Lys Asp Ser Ser Phe Glu Gln His Ser Val
            165                 170                 175

Gln Ile Met Val Lys Asp Tyr Ala Gly Lys Ile Lys Pro Ser Phe Asn
            180                 185                 190

Ile Val Pro Leu Thr Ser Arg Val Lys Pro Asp Pro Pro His Ile Lys
    195                 200                 205

Asn Leu Ser Phe His Asn Gly Asp Leu His Val Gln Trp Glu Asn Pro
    210                 215                 220

Gln Asn Phe Ile Ser Arg Cys Leu Phe Tyr Glu Val Glu Val Asn Asn
225                 230                 235                 240

Ser Gln Thr Glu Thr His Asn Val Phe Ser Val Gln Glu Ala Lys Cys
            245                 250                 255

Gln Asn Pro Glu Phe Glu Arg Asn Val Glu Asn Thr Ser Cys Phe Met
            260                 265                 270

Val Pro Gly Val Leu Pro Asp Thr Leu Asn Thr Val Arg Ile Arg Val
            275                 280                 285

-continued

```
Lys Thr Asn Lys Leu Cys Tyr Glu Asp Asp Lys Leu Trp Ser Asn Trp
            290                 295                 300

Ser Gln Glu Met Ser Ile Gly Lys Lys Arg Asn Ser Thr Leu Tyr Ile
305                 310                 315                 320

Thr Met Leu Leu Ile Val Pro Val Ile Val Ala Gly Ala Ile Ile Val
                325                 330                 335

Leu Leu Leu Tyr Leu Lys Arg Leu Lys Ile Ile Ile Phe Pro Pro Ile
                340                 345                 350

Pro Asp Pro Gly Lys Ile Phe Lys Glu Met Phe Gly Asp Gln Asn Asp
            355                 360                 365

Asp Thr Leu His Trp Lys Lys Tyr Asp Ile Tyr Glu Lys Gln Thr Lys
            370                 375                 380

Glu Glu Thr Asp Ser Val Val Leu Ile Glu Asn Leu Lys Lys Ala Ser
385                 390                 395                 400

Gln

<210> SEQ ID NO 3
<211> LENGTH: 398
<212> TYPE: PRT
<213> ORGANISM: Mus musculus

<400> SEQUENCE: 3

Thr Glu Val Gln Pro Pro Val Thr Asn Leu Ser Val Ser Val Glu Asn
1               5                   10                  15

Leu Cys Thr Ile Ile Trp Thr Trp Ser Pro Pro Glu Gly Ala Ser Pro
                20                  25                  30

Asn Cys Thr Leu Arg Tyr Phe Ser His Phe Asp Asp Gln Gln Asp Lys
            35                  40                  45

Lys Ile Ala Pro Glu Thr His Arg Lys Glu Glu Leu Pro Leu Asp Glu
50                  55                  60

Lys Ile Cys Leu Gln Val Gly Ser Gln Cys Ser Ala Asn Glu Ser Glu
65                  70                  75                  80

Lys Pro Ser Pro Leu Val Lys Lys Cys Ile Ser Pro Pro Glu Gly Asp
                85                  90                  95

Pro Glu Ser Ala Val Thr Glu Leu Lys Cys Ile Trp His Asn Leu Ser
            100                 105                 110

Tyr Met Lys Cys Ser Trp Leu Pro Gly Arg Asn Thr Ser Pro Asp Thr
            115                 120                 125

His Tyr Thr Leu Tyr Tyr Trp Tyr Ser Ser Leu Glu Lys Ser Arg Gln
130                 135                 140

Cys Glu Asn Ile Tyr Arg Glu Gly Gln His Ile Ala Cys Ser Phe Lys
145                 150                 155                 160

Leu Thr Lys Val Glu Pro Ser Phe Glu His Gln Asn Val Gln Ile Met
                165                 170                 175

Val Lys Asp Asn Ala Gly Lys Ile Arg Pro Ser Cys Lys Ile Val Ser
            180                 185                 190

Leu Thr Ser Tyr Val Lys Pro Asp Pro Pro His Ile Lys His Leu Leu
            195                 200                 205

Leu Lys Asn Gly Ala Leu Leu Val Gln Trp Lys Asn Pro Gln Asn Phe
210                 215                 220

Arg Ser Arg Cys Leu Thr Tyr Glu Val Glu Val Asn Asn Thr Gln Thr
225                 230                 235                 240

Asp Arg His Asn Ile Leu Glu Val Glu Glu Asp Lys Cys Gln Asn Ser
                245                 250                 255

Glu Ser Asp Arg Asn Met Glu Gly Thr Ser Cys Phe Gln Leu Pro Gly
```

```
                    260                 265                 270
Val Leu Ala Asp Ala Val Tyr Thr Val Arg Val Arg Val Lys Thr Asn
                275                 280                 285

Lys Leu Cys Phe Asp Asp Asn Lys Leu Trp Ser Asp Trp Ser Glu Ala
            290                 295                 300

Gln Ser Ile Gly Lys Glu Gln Asn Ser Thr Phe Tyr Thr Thr Met Leu
305                 310                 315                 320

Leu Thr Ile Pro Val Phe Val Ala Val Ala Val Ile Ile Leu Leu Phe
                325                 330                 335

Tyr Leu Lys Arg Leu Lys Ile Ile Ile Phe Pro Pro Ile Pro Asp Pro
            340                 345                 350

Gly Lys Ile Phe Lys Glu Met Phe Gly Asp Gln Asn Asp Asp Thr Leu
            355                 360                 365

His Trp Lys Lys Tyr Asp Ile Tyr Glu Lys Gln Ser Lys Glu Glu Thr
            370                 375                 380

Asp Ser Val Val Leu Ile Glu Asn Leu Lys Lys Ala Ala Pro
385                 390                 395

<210> SEQ ID NO 4
<211> LENGTH: 121
<212> TYPE: PRT
<213> ORGANISM: Artificial sequence
<220> FEATURE:
<223> OTHER INFORMATION: Synthetic 4B5 VH

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Lys Gly Leu Glu Trp Leu
        35                  40                  45

Thr Ile Ile Ser Asp Asp Gly Ser Asp Lys Tyr Tyr Ala Asp Ser Leu
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Val Glu Asp Thr Ala Leu Tyr Tyr Cys
                85                  90                  95

Ala Arg Glu Gly Gly His Tyr Tyr Asn Gly Met Asp Val Trp Gly
            100                 105                 110

Gln Gly Thr Thr Val Thr Val Ser Ser
        115                 120

<210> SEQ ID NO 5
<211> LENGTH: 10
<212> TYPE: PRT
<213> ORGANISM: Artificial sequence
<220> FEATURE:
<223> OTHER INFORMATION: Synthetic 4B5 VH CDR1

<400> SEQUENCE: 5

Gly Phe Ile Phe Ser Ser Tyr Ala Met His
1               5                   10

<210> SEQ ID NO 6
<211> LENGTH: 17
<212> TYPE: PRT
<213> ORGANISM: Artificial sequence
<220> FEATURE:
<223> OTHER INFORMATION: Synthetic 4B5 VH CDR2
```

-continued

<400> SEQUENCE: 6

Ile Ile Ser Asp Asp Gly Ser Asp Lys Tyr Tyr Ala Asp Ser Leu Lys
1               5                   10                  15

Gly

<210> SEQ ID NO 7
<211> LENGTH: 12
<212> TYPE: PRT
<213> ORGANISM: Artificial sequence
<220> FEATURE:
<223> OTHER INFORMATION: Synthetic 4B5 VH CDR3

<400> SEQUENCE: 7

Glu Gly Gly His Tyr Tyr Tyr Asn Gly Met Asp Val
1               5                   10

<210> SEQ ID NO 8
<211> LENGTH: 121
<212> TYPE: PRT
<213> ORGANISM: Artificial sequence
<220> FEATURE:
<223> OTHER INFORMATION: Synthetic 8B11 VH

<400> SEQUENCE: 8

Gln Ile Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Thr Ile Ile Ser Asp Asp Gly Ser Asn Lys Tyr Tyr Ala Ala Ser Val
        50                  55                  60

Gln Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Tyr Tyr Tyr Asn Gly Met Asp Val Trp Gly
            100                 105                 110

Gln Gly Thr Thr Val Thr Val Ser Ser
        115                 120

<210> SEQ ID NO 9
<211> LENGTH: 10
<212> TYPE: PRT
<213> ORGANISM: Artificial sequence
<220> FEATURE:
<223> OTHER INFORMATION: Synthetic 8B11 VH CDR1

<400> SEQUENCE: 9

Gly Phe Thr Phe Ser Ser Tyr Ala Met His
1               5                   10

<210> SEQ ID NO 10
<211> LENGTH: 17
<212> TYPE: PRT
<213> ORGANISM: Artificial sequence
<220> FEATURE:
<223> OTHER INFORMATION: Synthetic 8B11 VH CDR2

<400> SEQUENCE: 10

Ile Ile Ser Asp Asp Gly Ser Asn Lys Tyr Tyr Ala Ala Ser Val Gln
1               5                   10                  15

Gly

<210> SEQ ID NO 11
<211> LENGTH: 12
<212> TYPE: PRT
<213> ORGANISM: Artificial sequence
<220> FEATURE:
<223> OTHER INFORMATION: Synthetic 8B11 VH CDR3

<400> SEQUENCE: 11

Glu Gly Gly Tyr Tyr Tyr Tyr Asn Gly Met Asp Val
1               5                   10

<210> SEQ ID NO 12
<211> LENGTH: 121
<212> TYPE: PRT
<213> ORGANISM: Artificial sequence
<220> FEATURE:
<223> OTHER INFORMATION: Synthetic 15F4 VH

<400> SEQUENCE: 12

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Asp Asp Gly Ser Asn Lys Tyr Tyr Glu Val Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Ser Asn Asn Trp Tyr Val Gly Val Phe Asp Ile Trp Gly
            100                 105                 110

Gln Gly Thr Met Val Thr Val Ser Ser
        115                 120

<210> SEQ ID NO 13
<211> LENGTH: 10
<212> TYPE: PRT
<213> ORGANISM: Artificial sequence
<220> FEATURE:
<223> OTHER INFORMATION: Synthetic 15F4 VH CDR1

<400> SEQUENCE: 13

Gly Phe Thr Phe Ser Ser Tyr Gly Met His
1               5                   10

<210> SEQ ID NO 14
<211> LENGTH: 17
<212> TYPE: PRT
<213> ORGANISM: Artificial sequence
<220> FEATURE:
<223> OTHER INFORMATION: Synthetic 15F4 VH CDR2

<400> SEQUENCE: 14

Val Ile Trp Asp Asp Gly Ser Asn Lys Tyr Tyr Glu Val Ser Val Lys
1               5                   10                  15

Gly

<210> SEQ ID NO 15

```
<211> LENGTH: 12
<212> TYPE: PRT
<213> ORGANISM: Artificial sequence
<220> FEATURE:
<223> OTHER INFORMATION: Synthetic 15F4 VH CDR3

<400> SEQUENCE: 15

Asp Ser Asn Asn Trp Tyr Val Gly Val Phe Asp Ile
1               5                   10

<210> SEQ ID NO 16
<211> LENGTH: 108
<212> TYPE: PRT
<213> ORGANISM: Artificial sequence
<220> FEATURE:
<223> OTHER INFORMATION: Synthetic 15F4 VL

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 17
<211> LENGTH: 12
<212> TYPE: PRT
<213> ORGANISM: Artificial sequence
<220> FEATURE:
<223> OTHER INFORMATION: Synthetic 15F4 VL CDR1

<400> SEQUENCE: 17

Arg Ala Ser Gln Ser Val Ser Ser Thr Tyr Leu Ala
1               5                   10

<210> SEQ ID NO 18
<211> LENGTH: 7
<212> TYPE: PRT
<213> ORGANISM: Artificial sequence
<220> FEATURE:
<223> OTHER INFORMATION: Synthetic 15F4 VL CDR2

<400> SEQUENCE: 18

Gly Ala Ser Ser Arg Ala Thr
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic 15F4 VL CDR3

<400> SEQUENCE: 19

Gln Gln Tyr Gly Ser Ser Pro Phe Thr
1               5
```

<210> SEQ ID NO 20
<211> LENGTH: 324
<212> TYPE: PRT
<213> ORGANISM: Artificial sequence
<220> FEATURE:
<223> OTHER INFORMATION: Synthetic N-terminal FLAG-tagged
      hIL-13Ralpha1.ECR

<400> SEQUENCE: 20

Asp Tyr Lys Asp Asp Asp Glu Ser Arg Thr Glu Thr Gln Pro Pro Val
1               5                   10                  15

Thr Asn Leu Ser Val Ser Val Glu Asn Leu Cys Thr Val Ile Trp Thr
            20                  25                  30

Trp Asn Pro Pro Glu Gly Ala Ser Ser Asn Cys Ser Leu Trp Tyr Phe
        35                  40                  45

Ser His Phe Gly Asp Lys Gln Asp Lys Lys Ile Ala Pro Glu Thr Arg
    50                  55                  60

Arg Ser Ile Glu Val Pro Leu Asn Glu Arg Ile Cys Leu Gln Val Gly
65                  70                  75                  80

Ser Gln Cys Ser Thr Asn Glu Ser Glu Lys Pro Ser Ile Leu Val Glu
                85                  90                  95

Lys Cys Ile Ser Pro Pro Glu Gly Asp Pro Glu Ser Ala Val Thr Glu
            100                 105                 110

Leu Gln Cys Ile Trp His Asn Leu Ser Tyr Met Lys Cys Ser Trp Leu
        115                 120                 125

Pro Gly Arg Asn Thr Ser Pro Asp Thr Asn Tyr Thr Leu Tyr Tyr Trp
    130                 135                 140

His Arg Ser Leu Glu Lys Ile His Gln Cys Glu Asn Ile Phe Arg Glu
145                 150                 155                 160

Gly Gln Tyr Phe Gly Cys Ser Phe Asp Leu Thr Lys Val Lys Asp Ser
                165                 170                 175

Ser Phe Glu Gln His Ser Val Gln Ile Met Val Lys Asp Asn Ala Gly
            180                 185                 190

Lys Ile Lys Pro Ser Phe Asn Ile Val Pro Leu Thr Ser Arg Val Lys
        195                 200                 205

Pro Asp Pro Pro His Ile Lys Asn Leu Ser Phe His Asn Asp Asp Leu
    210                 215                 220

Tyr Val Gln Trp Glu Asn Pro Gln Asn Phe Ile Ser Arg Cys Leu Phe
225                 230                 235                 240

Tyr Glu Val Glu Val Asn Asn Ser Gln Thr Glu Thr His Asn Val Phe
                245                 250                 255

Tyr Val Gln Glu Ala Lys Cys Glu Asn Pro Glu Phe Glu Arg Asn Val
            260                 265                 270

Glu Asn Thr Ser Cys Phe Met Val Pro Gly Val Leu Pro Asp Thr Leu
        275                 280                 285

Asn Thr Val Arg Ile Arg Val Lys Thr Asn Lys Leu Cys Tyr Glu Asp
    290                 295                 300

Asp Lys Leu Trp Ser Asn Trp Ser Gln Glu Met Ser Ile Gly Lys Lys
305                 310                 315                 320

Arg Asn Ser Thr

<210> SEQ ID NO 21
<211> LENGTH: 363
<212> TYPE: DNA
<213> ORGANISM: Artificial sequence
<220> FEATURE:

<223> OTHER INFORMATION: Synthetic 4B5 VH

<400> SEQUENCE: 21

```
caggttcagc tggtggagtc tgggggaggc gtggtccagc ctggaggtc cctgagactc    60
tcctgtgcag cctctggatt catcttcagt agctatgcta tgcactgggt ccgccaggct   120
ccaggcaagg ggctggagtg gttgacaatt atatcagatg atggaagcga taaatactac   180
gcagactcct tgaagggccg attcaccatc tccagagaca attccaagaa gacgctgtat   240
ctgcaaatga acagcctgag agttgaggac acggctctat attactgtgc gagagagggg   300
ggacactact attataacgg tatggacgtt ggggccaagg gaccacggtc accgtctcct   360
cag                                                                363
```

<210> SEQ ID NO 22
<211> LENGTH: 30
<212> TYPE: DNA
<213> ORGANISM: Artificial sequence
<220> FEATURE:
<223> OTHER INFORMATION: Synthetic 4B5 VH CDR1

<400> SEQUENCE: 22

```
ggattcatct tcagtagcta tgctatgcac                                    30
```

<210> SEQ ID NO 23
<211> LENGTH: 51
<212> TYPE: DNA
<213> ORGANISM: Artificial sequence
<220> FEATURE:
<223> OTHER INFORMATION: Synthetic 4B5 VH CDR2

<400> SEQUENCE: 23

```
attatatcag atgatggaag cgataaatac tacgcagact ccttgaaggg c            51
```

<210> SEQ ID NO 24
<211> LENGTH: 36
<212> TYPE: DNA
<213> ORGANISM: Artificial sequence
<220> FEATURE:
<223> OTHER INFORMATION: Synthetic 4B5 VH CDR3

<400> SEQUENCE: 24

```
gagggggac actactatta taacggtatg gacgtt                              36
```

<210> SEQ ID NO 25
<211> LENGTH: 363
<212> TYPE: DNA
<213> ORGANISM: Artificial sequence
<220> FEATURE:
<223> OTHER INFORMATION: Synthetic 8B11 VH

<400> SEQUENCE: 25

```
caaatacagc tggtggagtc tgggggaggc gtggtccagc ctggaggtc cctgagactc    60
tcctgtgcag cctctggatt caccttcagt agctatgcta tgcactgggt ccgccaggct   120
ccaggcaagg ggctggagtg ggtgacaatt atatcagatg atggaagcaa taaatactac   180
gcagcctccg tgcagggccg attcaccatc tccagagaca attccaagaa gacgctgtat   240
ctgcaaatga acagcctgag agctgaggac acggctgtgt attactgtgc gagagagggg   300
ggatactact attataacgg tatggacgtc tggggccaag gaccacggt caccgtctcc   360
tca                                                                363
```

<210> SEQ ID NO 26

```
<211> LENGTH: 30
<212> TYPE: DNA
<213> ORGANISM: Artificial sequence
<220> FEATURE:
<223> OTHER INFORMATION: Synthetic 8B11 VH CDR1

<400> SEQUENCE: 26
ggattcacct tcagtagcta tgctatgcac                                            30

<210> SEQ ID NO 27
<211> LENGTH: 51
<212> TYPE: DNA
<213> ORGANISM: Artificial sequence
<220> FEATURE:
<223> OTHER INFORMATION: Synthetic 8B11 VH CDR2

<400> SEQUENCE: 27
attatatcag atgatggaag caataaatac tacgcagcct ccgtgcaggg c                    51

<210> SEQ ID NO 28
<211> LENGTH: 36
<212> TYPE: DNA
<213> ORGANISM: Artificial sequence
<220> FEATURE:
<223> OTHER INFORMATION: Synthetic 8B11 VH CDR3

<400> SEQUENCE: 28
gaggggggat actactatta taacggtatg gacgtc                                     36

<210> SEQ ID NO 29
<211> LENGTH: 363
<212> TYPE: DNA
<213> ORGANISM: Artificial sequence
<220> FEATURE:
<223> OTHER INFORMATION: Synthetic 15F4 VH

<400> SEQUENCE: 29
caggtgcagc tggtggagtc tgggggaggc gtggtccagc ctggaggtc cctgagactc            60 tcctgtgcag cgtctggatt caccttcagc agttatggca tgcactgggt ccgccaggct          120
ccaggcaagg ggctggagtg ggtggcagtt atatgggatg atggaagtaa taatactat           180 gaagtctccg tgaagggccg attcaccatc tccagagaca attccaagaa cacgctgtat          240
cttcaaatga acagcctgag agttgaggac acggctgtgt attactgtgc gagagatagc          300
aacaactggt acgtcggtgt ttttgatatc tggggccaag ggacaatggt caccgtctct          360
tca                                                                        363

<210> SEQ ID NO 30
<211> LENGTH: 30
<212> TYPE: DNA
<213> ORGANISM: Artificial sequence
<220> FEATURE:
<223> OTHER INFORMATION: Synthetic 15F4 VH CDR1

<400> SEQUENCE: 30
ggattcacct tcagcagtta tggcatgcac                                            30

<210> SEQ ID NO 31
<211> LENGTH: 51
<212> TYPE: DNA
<213> ORGANISM: Artificial sequence
<220> FEATURE:
<223> OTHER INFORMATION: Synthetic 15F4 VH CDR2

<400> SEQUENCE: 31
```

```
gttatatggg atgatggaag taataaatac tatgaagtct ccgtgaaggg c           51
```

<210> SEQ ID NO 32
<211> LENGTH: 36
<212> TYPE: DNA
<213> ORGANISM: Artificial sequence
<220> FEATURE:
<223> OTHER INFORMATION: Synthetic 15F4 VH CDR3

<400> SEQUENCE: 32

```
gatagcaaca actggtacgt cggtgttttt gatatc                           36
```

<210> SEQ ID NO 33
<211> LENGTH: 324
<212> TYPE: DNA
<213> ORGANISM: Artificial sequence
<220> FEATURE:
<223> OTHER INFORMATION: Synthetic 15F4 VL

<400> SEQUENCE: 33

```
gaaattgtgt tgacgcagtc tccaggcacc ctgtctttgt ctccagggga aagagccacc   60
ctctcctgca gggccagtca gagtgttagc agcacctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccatt cactttcggc  300
cctgggacca agtggatat caaa                                          324
```

<210> SEQ ID NO 34
<211> LENGTH: 36
<212> TYPE: DNA
<213> ORGANISM: Artificial sequence
<220> FEATURE:
<223> OTHER INFORMATION: Synthetic 15F4 VL CDR1

<400> SEQUENCE: 34

```
agggccagtc agagtgttag cagcacctac ttagcc                           36
```

<210> SEQ ID NO 35
<211> LENGTH: 21
<212> TYPE: DNA
<213> ORGANISM: Artificial sequence
<220> FEATURE:
<223> OTHER INFORMATION: Synthetic 15F4 VL CDR2

<400> SEQUENCE: 35

```
ggtgcatcca gcagggccac t                                           21
```

<210> SEQ ID NO 36
<211> LENGTH: 27
<212> TYPE: DNA
<213> ORGANISM: Artificial sequence
<220> FEATURE:
<223> OTHER INFORMATION: Synthetic 15F4 VL CDR3

<400> SEQUENCE: 36

```
cagcagtatg gtagctcacc attcact                                     27
```

<210> SEQ ID NO 37
<211> LENGTH: 117
<212> TYPE: PRT
<213> ORGANISM: Homo sapiens

<400> SEQUENCE: 37

```
Lys Pro Asp Pro Pro His Ile Lys Asn Leu Ser Phe His Asn Asp Asp
1               5                   10                  15

Leu Tyr Val Gln Trp Glu Asn Pro Gln Asn Phe Ile Ser Arg Cys Leu
            20                  25                  30

Phe Tyr Glu Val Glu Val Asn Asn Ser Gln Thr Glu Thr His Asn Val
        35                  40                  45

Phe Tyr Val Gln Glu Ala Lys Cys Glu Asn Pro Glu Phe Glu Arg Asn
    50                  55                  60

Val Glu Asn Thr Ser Cys Phe Met Val Pro Gly Val Leu Pro Asp Thr
65                  70                  75                  80

Leu Asn Thr Val Arg Ile Arg Val Lys Thr Asn Lys Leu Cys Tyr Glu
                85                  90                  95

Asp Asp Lys Leu Trp Ser Asn Trp Ser Gln Glu Met Ser Ile Gly Lys
            100                 105                 110

Lys Arg Asn Ser Thr
        115

<210> SEQ ID NO 38
<211> LENGTH: 336
<212> TYPE: PRT
<213> ORGANISM: Artificial sequence
<220> FEATURE:
<223> OTHER INFORMATION: Synthetic Fc domain of IgG1

<400> SEQUENCE: 38

Leu Val Thr Val Ser Ser Ala Ser Thr Lys Gly Pro Ser Val Phe Pro
1               5                   10                  15

Leu Ala Pro Ser Ser Lys Ser Thr Ser Gly Gly Thr Ala Ala Leu Gly
            20                  25                  30

Cys Leu Val Lys Asp Tyr Phe Pro Glu Pro Val Thr Val Ser Trp Asn
        35                  40                  45

Ser Gly Ala Leu Thr Ser Gly Val His Thr Phe Pro Ala Val Leu Gln
    50                  55                  60

Ser Ser Gly Leu Tyr Ser Leu Ser Ser Val Val Thr Val Pro Ser Ser
65                  70                  75                  80

Ser Leu Gly Thr Gln Thr Tyr Ile Cys Asn Val Asn His Lys Pro Ser
                85                  90                  95

Asn Thr Lys Val Asp Lys Lys Ala Glu Pro Lys Ser Cys Asp Lys Thr
            100                 105                 110

His Thr Cys Pro Pro Cys Pro Ala Pro Glu Leu Leu Gly Gly Pro Ser
        115                 120                 125

Val Phe Leu Phe Pro Pro Lys Pro Lys Asp Thr Leu Met Ile Ser Arg
    130                 135                 140

Thr Pro Glu Val Thr Cys Val Val Val Asp Val Ser His Glu Asp Pro
145                 150                 155                 160

Glu Val Lys Phe Asn Trp Tyr Val Asp Gly Val Glu Val His Asn Ala
                165                 170                 175

Lys Thr Lys Pro Arg Glu Glu Gln Tyr Asn Ser Thr Tyr Arg Val Val
            180                 185                 190

Ser Val Leu Thr Val Leu His Gln Asp Trp Leu Asn Gly Lys Glu Tyr
        195                 200                 205

Lys Cys Lys Val Ser Asn Lys Ala Leu Pro Ala Pro Ile Glu Lys Thr
    210                 215                 220

Ile Ser Lys Ala Lys Gly Gln Pro Arg Glu Pro Gln Val Tyr Thr Leu
225                 230                 235                 240

Pro Pro Ser Arg Asp Glu Leu Thr Lys Asn Gln Val Ser Leu Thr Cys
```

```
            245                 250                 255
Leu Val Lys Gly Phe Tyr Pro Ser Asp Ile Ala Val Glu Trp Glu Ser
            260                 265                 270
Asn Gly Gln Pro Glu Asn Asn Tyr Lys Thr Thr Pro Pro Val Leu Asp
            275                 280                 285
Ser Asp Gly Ser Phe Phe Leu Tyr Ser Lys Leu Thr Val Asp Lys Ser
            290                 295                 300
Arg Trp Gln Gln Gly Asn Val Phe Ser Cys Ser Val Met His Glu Ala
305                 310                 315                 320
Leu His Asn His Tyr Thr Gln Lys Ser Leu Ser Leu Ser Pro Gly Lys
            325                 330                 335

<210> SEQ ID NO 39
<211> LENGTH: 332
<212> TYPE: PRT
<213> ORGANISM: Artificial sequence
<220> FEATURE:
<223> OTHER INFORMATION: Synthetic Fc domain of IgG2

<400> SEQUENCE: 39

Leu Val Thr Val Ser Ser Ala Ser Thr Lys Gly Pro Ser Val Phe Pro
1               5                   10                  15
Leu Ala Pro Cys Ser Arg Ser Thr Ser Glu Ser Thr Ala Ala Leu Gly
            20                  25                  30
Cys Leu Val Lys Asp Tyr Phe Pro Glu Pro Val Thr Val Ser Trp Asn
            35                  40                  45
Ser Gly Ala Leu Thr Ser Gly Val His Thr Phe Pro Ala Val Leu Gln
        50                  55                  60
Ser Ser Gly Leu Tyr Ser Leu Ser Ser Val Val Thr Val Thr Ser Ser
65                  70                  75                  80
Asn Phe Gly Thr Gln Thr Tyr Thr Cys Asn Val Asp His Lys Pro Ser
                85                  90                  95
Asn Thr Lys Val Asp Lys Thr Val Glu Arg Lys Cys Cys Val Glu Cys
            100                 105                 110
Pro Pro Cys Pro Ala Pro Pro Val Ala Gly Pro Ser Val Phe Leu Phe
            115                 120                 125
Pro Pro Lys Pro Lys Asp Thr Leu Met Ile Ser Arg Thr Pro Glu Val
            130                 135                 140
Thr Cys Val Val Val Asp Val Ser His Glu Asp Pro Glu Val Gln Phe
145                 150                 155                 160
Asn Trp Tyr Val Asp Gly Val Glu Val His Asn Ala Lys Thr Lys Pro
                165                 170                 175
Arg Glu Glu Gln Phe Asn Ser Thr Phe Arg Val Val Ser Val Leu Thr
            180                 185                 190
Val Val His Gln Asp Trp Leu Asn Gly Lys Glu Tyr Lys Cys Lys Val
            195                 200                 205
Ser Asn Lys Gly Leu Pro Ala Pro Ile Glu Lys Thr Ile Ser Lys Thr
        210                 215                 220
Lys Gly Gln Pro Arg Glu Pro Gln Val Tyr Thr Leu Pro Pro Ser Arg
225                 230                 235                 240
Glu Glu Met Thr Lys Asn Gln Val Ser Leu Thr Cys Leu Val Lys Gly
                245                 250                 255
Phe Tyr Pro Ser Asp Ile Ala Val Glu Trp Glu Ser Asn Gly Gln Pro
            260                 265                 270
Glu Asn Asn Tyr Lys Thr Thr Pro Pro Met Leu Asp Ser Asp Gly Ser
            275                 280                 285
```

```
Phe Phe Leu Tyr Ser Lys Leu Thr Val Asp Lys Ser Arg Trp Gln Gln
    290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly Lys
                325                 330

<210> SEQ ID NO 40
<211> LENGTH: 333
<212> TYPE: PRT
<213> ORGANISM: Artificial sequence
<220> FEATURE:
<223> OTHER INFORMATION: Synthetic Fc domain of IgG4

<400> SEQUENCE: 40

Leu Val Thr Val Ser Ser Ala Ser Thr Lys Gly Pro Ser Val Phe Pro
1               5                   10                  15
Leu Ala Pro Cys Ser Arg Ser Thr Ser Glu Ser Thr Ala Ala Leu Gly
                20                  25                  30
Cys Leu Val Lys Asp Tyr Phe Pro Glu Pro Val Thr Val Ser Trp Asn
                35                  40                  45
Ser Gly Ala Leu Thr Ser Gly Val His Thr Phe Pro Ala Val Leu Gln
    50                  55                  60
Ser Ser Gly Leu Tyr Ser Leu Ser Ser Val Val Thr Val Pro Ser Ser
65                  70                  75                  80
Ser Leu Gly Thr Lys Thr Tyr Thr Cys Asn Val Asp His Lys Pro Ser
                85                  90                  95
Asn Thr Lys Val Asp Lys Arg Val Glu Ser Lys Tyr Gly Pro Pro Cys
                100                 105                 110
Pro Ser Cys Pro Ala Pro Glu Phe Leu Gly Gly Pro Ser Val Phe Leu
            115                 120                 125
Phe Pro Pro Lys Pro Lys Asp Thr Leu Met Ile Ser Arg Thr Pro Glu
    130                 135                 140
Val Thr Cys Val Val Val Asp Val Ser Gln Glu Asp Pro Glu Val Gln
145                 150                 155                 160
Phe Asn Trp Tyr Val Asp Gly Val Glu Val His Asn Ala Lys Thr Lys
                165                 170                 175
Pro Arg Glu Glu Gln Phe Asn Ser Thr Tyr Arg Val Val Ser Val Leu
            180                 185                 190
Thr Val Leu His Gln Asp Trp Leu Asn Gly Lys Glu Tyr Lys Cys Lys
        195                 200                 205
Val Ser Asn Lys Gly Leu Pro Ser Ser Ile Glu Lys Thr Ile Ser Lys
    210                 215                 220
Ala Lys Gly Gln Pro Arg Glu Pro Gln Val Tyr Thr Leu Pro Pro Ser
225                 230                 235                 240
Gln Glu Glu Met Thr Lys Asn Gln Val Ser Leu Thr Cys Leu Val Lys
                245                 250                 255
Gly Phe Tyr Pro Ser Asp Ile Ala Val Glu Trp Glu Ser Asn Gly Gln
            260                 265                 270
Pro Glu Asn Asn Tyr Lys Thr Thr Pro Pro Val Leu Asp Ser Asp Gly
        275                 280                 285
Ser Phe Phe Leu Tyr Ser Arg Leu Thr Val Asp Lys Ser Arg Trp Gln
    290                 295                 300
Glu Gly Asn Val Phe Ser Cys Ser Val Met His Glu Ala Leu His Asn
305                 310                 315                 320
```

```
His Tyr Thr Gln Lys Ser Leu Ser Leu Ser Leu Gly Lys
                325                 330

<210> SEQ ID NO 41
<211> LENGTH: 332
<212> TYPE: PRT
<213> ORGANISM: Artificial sequence
<220> FEATURE:
<223> OTHER INFORMATION: Synthetic Fc domain of IgG2M4

<400> SEQUENCE: 41

Leu Val Thr Val Ser Ser Ala Ser Thr Lys Gly Pro Ser Val Phe Pro
1               5                   10                  15

Leu Ala Pro Cys Ser Arg Ser Thr Ser Glu Ser Thr Ala Ala Leu Gly
            20                  25                  30

Cys Leu Val Lys Asp Tyr Phe Pro Glu Pro Val Thr Val Ser Trp Asn
        35                  40                  45

Ser Gly Ala Leu Thr Ser Gly Val His Thr Phe Pro Ala Val Leu Gln
    50                  55                  60

Ser Ser Gly Leu Tyr Ser Leu Ser Ser Val Val Thr Val Thr Ser Ser
65                  70                  75                  80

Asn Phe Gly Thr Gln Thr Tyr Thr Cys Asn Val Asp His Lys Pro Ser
                85                  90                  95

Asn Thr Lys Val Asp Lys Thr Val Glu Arg Lys Cys Cys Val Glu Cys
            100                 105                 110

Pro Pro Cys Pro Ala Pro Pro Val Ala Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser Gln Glu Asp Pro Glu Val Gln Phe
145                 150                 155                 160

Asn Trp Tyr Val Asp Gly Val Glu Val His Asn Ala Lys Thr Lys Pro
                165                 170                 175

Arg Glu Glu Gln Phe Asn Ser Thr Phe Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Gly Leu Pro Ser Ser Ile Glu Lys Thr Ile Ser Lys Thr
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Met Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 42
<211> LENGTH: 326
<212> TYPE: PRT
```

-continued

<213> ORGANISM: Artificial sequence
<220> FEATURE:
<223> OTHER INFORMATION: Synthetic construct containing Fc domain of
      IgG2M4

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 43
<211> LENGTH: 978
<212> TYPE: DNA
<213> ORGANISM: Artificial sequence
<220> FEATURE:
<223> OTHER INFORMATION: Synthetic construct containing Fc domain of
      IgG2M4

<400> SEQUENCE: 43

```
gcctccacca agggcccatc cgtcttcccc ctggcgccct gctccaggag cacctccgag        60
agcacagccg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgacctcca gcaactttgg cacgcagacc       240
tacacctgca acgtagatca caagcccagc aacaccaagg tggacaagac agttgagcgg       300
aaatgctgcg tggagtgccc accatgccca gcacctccag tggccggacc atcagtcttc       360
ctgttccccc caaaacccaa ggacactctc atgatctccc ggacccctga ggtcacgtgc       420
gtggtggtgg acgtgagcca ggaagacccc gaggtccagt tcaactggta cgtggatggc       480
gtggaggtgc ataatgccaa gacaaagccg cgggaggagc agttcaacag cacgttccgt       540
gtggtcagcg tcctcaccgt cctgcaccag gactggctga acggcaagga gtacaagtgc       600
aaggtctcca acaaaggcct cccgtcctcc atcgagaaaa ccatctccaa aaccaaaggg       660
cagccccgag agccacaggt gtacaccctg cccccatccc gggaggagat gaccaagaac       720
caggtcagcc tgacctgcct ggtcaaaggc ttctacccca gcgacatcgc cgtggagtgg       780
gagagcaatg ggcagccgga gaacaactac aagaccacgc ctcccatgct ggactccgac       840
ggctccttct tcctctacag caagctaacc gtggacaaga gcaggtggca gcagggGgaat       900 gtcttctcat gctccgtgat gcatgaggct ctgcacaacc actacacaca gaagagcctc       960
tccctgtctc ctggtaaa                                                    978

<210> SEQ ID NO 44
<211> LENGTH: 5
<212> TYPE: PRT
<213> ORGANISM: Artificial sequence
<220> FEATURE:
<223> OTHER INFORMATION: Synthetic peptide

<400> SEQUENCE: 44

Val Phe Tyr Val Gln
1               5

<210> SEQ ID NO 45
<211> LENGTH: 5
<212> TYPE: PRT
<213> ORGANISM: Artificial sequence
<220> FEATURE:
<223> OTHER INFORMATION: Synthetic peptide

<400> SEQUENCE: 45

Ile Leu Glu Val Glu
1               5

<210> SEQ ID NO 46
<211> LENGTH: 314
<212> TYPE: PRT
<213> ORGANISM: Mus musculus

<400> SEQUENCE: 46

Thr Glu Val Gln Pro Pro Val Thr Asn Leu Ser Val Ser Val Glu Asn
1               5                   10                  15

Leu Cys Thr Ile Ile Trp Thr Trp Ser Pro Pro Glu Gly Ala Ser Pro
                20                  25                  30

Asn Cys Thr Leu Arg Tyr Phe Ser His Phe Asp Asp Gln Gln Asp Lys
            35                  40                  45

Lys Ile Ala Pro Glu Thr His Arg Lys Glu Glu Leu Pro Leu Asp Glu
        50                  55                  60
```

```
Lys Ile Cys Leu Gln Val Gly Ser Gln Cys Ser Ala Asn Glu Ser Glu
 65                  70                  75                  80

Lys Pro Ser Pro Leu Val Lys Lys Cys Ile Ser Pro Pro Glu Gly Asp
                 85                  90                  95

Pro Glu Ser Ala Val Thr Glu Leu Lys Cys Ile Trp His Asn Leu Ser
            100                 105                 110

Tyr Met Lys Cys Ser Trp Leu Pro Gly Arg Asn Thr Ser Pro Asp Thr
        115                 120                 125

His Tyr Thr Leu Tyr Tyr Trp Tyr Ser Ser Leu Glu Lys Ser Arg Gln
    130                 135                 140

Cys Glu Asn Ile Tyr Arg Glu Gly Gln His Ile Ala Cys Ser Phe Lys
145                 150                 155                 160

Leu Thr Lys Val Glu Pro Ser Phe Glu His Gln Asn Val Gln Ile Met
                165                 170                 175

Val Lys Asp Asn Ala Gly Lys Ile Arg Pro Ser Cys Lys Ile Val Ser
            180                 185                 190

Leu Thr Ser Tyr Val Lys Pro Asp Pro Pro His Ile Lys His Leu Leu
        195                 200                 205

Leu Lys Asn Gly Ala Leu Leu Val Gln Trp Lys Asn Pro Gln Asn Phe
    210                 215                 220

Arg Ser Arg Cys Leu Thr Tyr Glu Val Glu Val Asn Asn Thr Gln Thr
225                 230                 235                 240

Asp Arg His Asn Ile Leu Glu Val Glu Glu Asp Lys Cys Gln Asn Ser
            245                 250                 255

Glu Ser Asp Arg Asn Met Glu Gly Thr Ser Cys Phe Gln Leu Pro Gly
        260                 265                 270

Val Leu Ala Asp Ala Val Tyr Thr Val Arg Val Arg Val Lys Thr Asn
        275                 280                 285

Lys Leu Cys Phe Asp Asp Asn Lys Leu Trp Ser Asp Trp Ser Glu Ala
    290                 295                 300

Gln Ser Ile Gly Lys Glu Gln Asn Ser Thr
305                 310
```

What is claimed is:

1. An isolated antibody which:
   (i) binds to human interleukin-13 receptor alpha 1 through one or more of amino acid residues 248-252 (Val-Phe-Tyr-Val-Gln) (SEQ ID NO: 44) of said receptor,
   (ii) inhibits interleukin-13 signaling, and
   (iii) does not cross-react with cynomolgus monkey interleukin-13 receptor alpha 1.

2. The isolated antibody of claim 1, wherein said antibody comprises a heavy chain variable region having an amino acid sequence selected from the group consisting of SEQ ID NO: 4 and SEQ ID NO:8.

3. The isolated antibody of claim 1, wherein said antibody is a human antibody.

4. The isolated antibody of claim 1, wherein said antibody is a humanized, deimmunized, primatitized or chimeric antibody.

5. A composition comprising the isolated antibody of claim 1 and a pharmaceutically acceptable carrier.

6. An isolated nucleic acid molecule encoding the isolated antibody of claim 1.

7. A vector comprising the isolated nucleic acid molecule of claim 6.

8. A host cell comprising the vector of claim 7.

9. A method of treating an interleukin 13-related disorder or disease comprising administering to a subject in need of treatment an effective amount of the composition of claim 5 thereby treating the interleukin 13-related disorder or disease in the subject, wherein the interleukin 13-related disorder or disease is asthma, allergic rhinitis, or ulcerative colitis.

* * * * *